US009738711B2

(12) United States Patent
Comb et al.

(10) Patent No.: US 9,738,711 B2
(45) Date of Patent: *Aug. 22, 2017

(54) PRODUCTION OF MOTIF-SPECIFIC AND CONTEXT-INDEPENDENT ANTIBODIES USING PEPTIDE LIBRARIES AS ANTIGENS

(71) Applicant: Cell Signaling Technology, Inc., Danvers, MA (US)

(72) Inventors: Michael J. Comb, Manchester, MA (US); Yi Tan, Lynnfield, MA (US); Peter Hornbeck, Magnolia, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/573,635

(22) Filed: Dec. 17, 2014

(65) Prior Publication Data
US 2015/0259405 A1 Sep. 17, 2015

Related U.S. Application Data

(63) Continuation of application No. 11/484,485, filed on Jul. 11, 2006, now Pat. No. 9,085,609, which is a continuation-in-part of application No. 10/014,485, filed on Nov. 13, 2001, now Pat. No. 7,259,022, which is a continuation-in-part of application No. 09/535,364, filed on Mar. 24, 2000, now Pat. No. 6,982,318, which is a continuation-in-part of application No. 09/148,712, filed on Sep. 4, 1998, now Pat. No. 6,441,140.

(51) Int. Cl.
C07K 16/18 (2006.01)
C07K 16/00 (2006.01)

(52) U.S. Cl.
CPC .............. *C07K 16/18* (2013.01); *C07K 16/00* (2013.01); *C07K 2317/20* (2013.01)

(58) Field of Classification Search
CPC .......................................... C07K 16/00–16/468
See application file for complete search history.

(56) References Cited

U.S. PATENT DOCUMENTS

| 5,532,167 | A | 7/1996 | Cantley et al. | |
|---|---|---|---|---|
| 5,679,769 | A | 10/1997 | Danishefsky et al. | |
| 5,716,836 | A | 2/1998 | Suiko | |
| 5,759,787 | A | 6/1998 | Strulovici | |
| 6,001,580 | A | 12/1999 | Tani et al. | |
| 6,441,140 | B1 * | 8/2002 | Comb | C07K 16/44 435/7.1 |
| 6,489,136 | B1 | 12/2002 | Zervos | |
| 6,982,318 | B1 * | 1/2006 | Comb | C07K 16/44 530/387.1 |
| 7,198,896 | B2 * | 4/2007 | Rush | C07K 16/44 210/601 |
| 7,259,022 | B2 * | 8/2007 | Comb | C07K 16/44 436/547 |
| 7,300,753 | B2 * | 11/2007 | Rush | C07K 14/47 435/174 |
| 7,344,714 | B2 * | 3/2008 | Comb | C07K 16/44 424/139.1 |
| 9,085,609 | B2 * | 7/2015 | Comb | C07K 16/00 |
| 2002/0168684 | A1 | 11/2002 | Comb et al. | |
| 2015/0232540 | A1 | 8/2015 | Comb et al. | |

FOREIGN PATENT DOCUMENTS

| EP | 054492 | 6/1982 |
|---|---|---|
| EP | 0054492 | 6/1982 |
| WO | 98/29452 | 7/1998 |

OTHER PUBLICATIONS

Pearson and Kemp, Methods in Enzymology, 1991; 200:62-81.*
Alessi et al. "Mechanism of activation of protein kinase B by insulin and IGF-1," The EMBOJ, vol. 15, No. 23, pp. 6541-6551 (1996).
Alessi et al. "Molecular basis for the substrate specificity of protein kinase B; comparison with MAPKAP kinase-1 and p70 S6 kinase," FEBS Lett., vol. 399, No. 3, pp. 333-338 (1996).
Bangalore et al. "Antiserum raised against a synthetic phosphotyrosine-containing peptide selectively recognized p185neu/erbB-2 and the epidermal growth factor receptor," Proc. Natl. Acad. Sci. USA, vol. 89, pp. 11637-11641 (1992).
Brunet et al. "Akt Promotes Cell Survival by Phosphorylating and Inhibiting a Forkhead Transcription Factor," Cell, vol. 96, pp. 857-868 (1999).
Burbelo et al. "14-3-3 Proteins: Hot numbers in signal transduction," Curr. Biol., vol. 5, No. 2, pp. 95-96 (1995).
Cantley Cell Signaling Technology Inc.'s 2000-2001 Catalogue, p. 198.
Capra et al. "The Antibody Combining Site" Sci. Am., vol. 236, pp. 50-59 (1977).
Cardone et al. "Regulation of Cell Death Protease Caspase-9 by Phosphorylation," Science, vol. 282, No. 5392, pp. 1318-1321 (1998).

(Continued)

*Primary Examiner* — Jessica H Roark
(74) *Attorney, Agent, or Firm* — McDonnell Boehnen Hulbert & Berghoff LLP

(57) ABSTRACT

A method is provided for producing motif-specific, context-independent antibodies that recognize a plurality of peptides or proteins within a genome that contain the same post-translationally modified motif. The method includes the step of immunizing a host with a degenerate peptide library antigen featuring (i) a fixed target motif containing one or more invariant amino acids including at least one modified amino acid, and (ii) a plurality of degenerate amino acids flanking the motif. Motif-specific, context-independent antibodies produced by the disclosed method are also provided. The method encompasses motifs consisting of a single modified amino acid, as well as short motifs comprising multiple invariant amino acids including one or more modified amino acids, such as all or part of kinase consensus substrate motifs, protein-protein binding motifs, or other cell signaling motifs. Methods of using the antibodies, e.g. for genome-wide profiling, are also provided.

12 Claims, 25 Drawing Sheets

(56) References Cited

OTHER PUBLICATIONS

Czernik et al. "Production of phosphorylation state-specific antibodies." Methods Enzymol., vol. 201, pp. 264-283 (1991).
Czernik et al. Neuroprotocols. "Phosphorylation State-Specific antibodies: Preparation and Applications." vol. 6, pp. 56-61 (1995).
Dalby et al. "Identification of Regulatory Phosphoylation Sites in Mitogen-activated Protein Kinase (MAPK)-activated Protein Kinase-1 a/p90rsk That Are Inducible by MAPK," J Biol. Chern., vol. 273, No. 3, pp. 1496-1505 (1998).
Datta et al. "Akt phosphorylation of BAD couples survival signals to the cell-intrinsic death machinery," Cell, vol. 91, No. 2, pp. 231-241 (1997).
Franke et al. "PBK: downstream AKTion blocks apoptosis." Cell, vol. 88, No. 4, pp. 435-437 (1997).
Fukunaga et al. "MNK1, a new MAP kinase-activated protein kinase, isolated by a novel expression screening method for identifYing protein kinase substrates." The EMBOJ, vol. 16, No. 8, pp. 1921-1933 (1997).
Glenney et al. J Immun. Methods, "Monoclonal antibodies to phosphotyrosine", vol. 109, pp. 277-285 (1988).
Hamaguchi et al. "Phosphorylation of cellular proteins in Rous sarcoma virus-infected cells: analysis by use of antiphosphotyrosine antibodies," Molecular & Cellular Biology, vol. 8, No. 8, pp. 3035-3042 (1988).
Harlow et al. "Antibody-Antigen Interactions: Structure of the antibody-antigen complex," A Laboratory Manual, pp. 24-27, Cold Spring Harbor Laboratory Press (1999).
Harlow et al. Antibodies: A Laboratory Manual, Chapter 5, pp. 72-77, Cold Spring Harbor Laboratory Press (1988).
Hebbes et al. "A 'minimal epitope' anti-protein antibody that recognizes a single modified amino acid," Molecular Immunology, vol. 26, No. 9, pp. 865-873 (1989).
Heffetz et al. Method. Enzymol., "Generation and use of antibodies to phosphothreonine", vol. 201, pp. 44-53 (1991).
Huse et al. "Generation of a large combinatorial library of the immunoglobulin repertoire in phage lambda", Science, vol. 246, pp. 1275-1281 (1989).
Imhof et al. Curr. Biol., "Acetylation of general transcription factors by histone acetyltransferases", vol. 7, pp. 689-692 (1997).
Kamps "Generation and Use of Anti-Phosphotyrosine Antibodies for Immunoblotting," Methods in Enzymology, vol. 201, pp. 101-111 (1991).
Kemp et al. "Protein kinase recognition sequence motifs," Trends Biochem. Sci., vol. 15, No. 9, pp. 342-346 (1990).
Keranen et al. "Protein Kinase C is Regulated In Vivo by Three Functionally Distinct Phosphorylations," Curr. Biol., vol. 5, pp. 1394-1403 (1995).
Khachigian et al. "A crossreactive antipeptide monoclonal antibody with specificity for lysyl-lysine," Journal of Immunological Methods, vol. 140, No. 2, pp. 249-258 (1991).
Kolle et al. "Substrate and sequential site specificity of cytoplasmic histone acetyltransferases of maize and rat-liver," Febs. Lett., vol. 421, pp. 109-114 (1998).
Kuby Immunology, 3rd Ed. pp. 92-96, Freeman & Co. (1998).
Kushima et al. "Characterization ofHPC-1 antigen, an isoform of syntaxin-1, with the isoform-specific monoclonal antibody, 14D8," Journal of Molecular Neuroscience, vol. 8, No. 1, pp. 19-27 (1997).
Levine et al. "Antibodies and radioimmunoassays for phosphoserine, phosphothreonine and phosphotyrosine: Serologic specificities and levels of the phosphoamino acids in cytoplasmic fractions of rat tissues," Journal of Immunological Methods, vol. 124, No. 2, pp. 239-249 (1989).
Lichtenberg-Kraag et al. "Phosphorylation-dependent eptiopes of neurofilament antibodies on tau protein and relationship with Alzheimber tau," Proc. Natl. Acad. Sci. USA, vol. 89, pp. 5384-5388 (Jun. 1992).
Miceli et al. "Two-stage selection of sequences from a random phage display library delineates both core residues and permitted structural range within an epitope," J Immun. Methods, vol. 167, Nos. 1-2, 3, pp. 279-287 (1994).
Montminy "Transcriptional Regulation by Cyclic AMP," Annu. Rev. Biochem., vol. 66, pp. 807-822 (1997).
Muslin et al. Cell, "Interaction of 14-3-3 with signaling proteins is mediated by the recognition of phosphoserine", vol. 84, pp. 889-897 (1996).
Nishilawa et al. "Determination of the Specific Substrate Sequence Motifs of Protein Kinase C Isozymes," J Biol. Chem., vol. 272, No. 2, pp. 952-960.
Pap et al. "Role of Glycogen Synthase Kinase-3 in the Phosphatidylinositol3-Kinase/Akt Cell Survival Pathway," J Biol. Chern., vol. 273, No. 32, pp. 19929-19932 (1998).
Peng et al. Science, "Mitotic and G2 checkpoint control: regulation of 14-3-3 protein binding by phosphorylation of Cdc25C on serine-216", vol. 277, pp. 1501-1508 (1997).
Pinilla et al. "Elucidation of monoclonal antibody polyspeciticity using a synthetic combinatorial library", Peptide Research, vol. 8, pp. 250-257 (1995).
Poulter et al. "Locations and Immunoreactivities of Phosphorylation Sites on Bovine and Porcine Tau Proteins and a PHF-Tau Fragment," J Biol. Chem., vol. 268., No. 13, pp. 9636-9644 (1993).
Reichmann et al. "Reshaping human antibodies for therapy," Nature, vol. 332, pp. 323-327 (1988).
Rosenberg et al. "Characterization of a Distinct Binding Site for the Prokaryotic Chaperone, GroEL, on a Human Granulocyte Ribonuclease," J Biol. Chem., vol. 268, No. 6, pp. 4499-4503 (1993).
Ross et al. "Phosphotyrosine-containing proteins isolated by affinity chromatography with antibodies to synthetic hapten," Nature, vol. 294, pp. 654-656 (1981).
Songyang et al. "Use of an oriented peptide library to determine the optimal substrates of protein kinases," Curr. Bio., vol. 4, No. 11, pp. 973-982 (1994).
Songyang et al. "A structural basis for substrate specificities of protein Ser/Thr-kinases: Primary sequence preference of casein kinase I and II, NIMA, phosphorylase kinase, CaM kinase II, CDK5 and Erk1," Mol. Cell. Biol., vol. 16, pp. 6486-6493 (1996).
Struhl "Histone acetylation and transcriptional regulatory mechanisms," Genes & Dev., vol. 12, pp. 599-606 (1998).
Stukenberg et al. "Systematic identification of mitotic phosphoproteins," Curr. Bio., vol. 7, No. 5, pp. 338-348 (1997).
Suzuki et al. "Antibody specific for the Thr-286-autophosphorylated a subunit of Ca2+/ calmodulindependent protein kinase II," Proc. Natl. Acad. Sci. USA, vol. 89, pp. 109-113 (1992).
Verhoeven et al. "Reshaping human antibodies: Grafting an antilysozyme activity," Science, vol. 239, pp. 1534-1536 (1988).
Westendorf "Cloning of cDNAs for M-phase phosphoproteins recognized by the MPM2 monoclonal antibody and determination of the phosphorylated epitope," Proc. Natl. Acad. Sci. USA, vol. 91, pp. 714-718 (1994).
Yaffe et al. "The Structural Basis for 14-3-3: Phosphopeptide Binding Specificity," Cell, vol. 91, pp. 961-971 (1997).
Yaffe et al. "Sequence-specific and phosphorylation-dependent proline isomerization: a potential mitotic regulatory mechanism," Science, vol. 278, No. 5345, pp. 1957-1960 (1997).
Yaffe et al. "A motif-based profile scanning approach for genome-wide prediction of signaling pathways," Nature Biotech., vol. 19, pp. 348-353 (2001).
Zha et al. "Serine Phosphorylation of Death Agonist BAD in Response to Survival Factor Results in Binding to 14-3-3 Not BCL-X," Cell, vol. 87, No. 4, pp. 619-628 (1996).
Current Protocols in Immunology, Unit 9.3:Selection ofImmunogenic Peptides for Antisera Production 9.31-9.33 (1991).
Protein Phosphorylation: A Practical Approach, ed. Hardie, p. 267, IRL Press (1993).
Sigma 1998 Catalog, pp. 1305 and 1309.
Upstate Biotechnology 1998 Catalog, p. 17.
Upstate Biotechnology 2001 Catalog, p. 221.
Zymed Laboratories 1996-1997 General Catalog,p. 80.

(56) References Cited

OTHER PUBLICATIONS

Cell Signaling Technology Inc.'s 2000-2001 Catalogue, pp. 14 and 198.

Yamaguchi et al., "Substrate specificity of the human protein phosphatase 2Cdelta, Wip1", Biochem 2005; 44:5285-94.

Zhao et al., "The mechanism of dephosphorylation of extracellular signal-regulated kinase 2 by mitogen-activated protein kinase phosphatase 3", J Biol. Chem. 2001; 276:32382-91.

Katou et al., "Catalytic activation of the plant MAPK phosphatase NtMKP1 by its physiological substrate salicylic acid-induced protein kinase but not by calmodulins", J. Biol. Chem., 2005; 280:39569-81.

Donella-Deana et al., "Dephosphorylation of phosphopeptides by calcineurin (protein phosphatase 2B)", Eur. J. Biochem 1994; 219:109-17.

Boisvert et al., "A proteomic analysis of arginine-methylated protein complexes", Mol Cell Proteomics 2003; 2:1319-30.

Brahms et al., "The C-terminal RG dipeptide repeats of the spliceosomal Sm proteins D1 and D3 contain symmetrical dimethylarginines, which form a major B-cell epitope for anti-Sm autoantibodies", J. Biol. Chem. 2000; 275:17122-29.

Siebel et al., "The essential yeast RNA binding protein Np13p is methylated", Proc Nat'l Acad Sci. 1996; 93:13641-46.

AB412 Datasheet (Abcam monoclonal antibody 7E6), downloaded from Abcam website Sep. 18, 2013.

Komatsu et al., "Four different clones of mouse anti-acetyllysine monoclonal antibodies having different recognition properties share a common immunoglobulin framework structure", J Immunol Meth 2003; 272:161-75.

Hinson et al. "Immunochemical detection of drug-protein adducts in acetaminophen hepatotoxicity", Adv Exp Med Biol, 1996, vol. 387, pp. 47-55.

Pearson and Kemp "Protein kinase phosphorylation site sequences and consensus specificity motifs: tabulations", Methods in Enzymology, 1991, vol. 200, pp. 62-81.

Martinez-Martinez et al., "Blockade of NFAT activation by the second calcineurin binding site", J. Biol. Chem., Mar. 10, 2006; 281:6227-6235.

al-Obeidi et al. "Protein tyrosine kinases: Structure, substrate specificity, and drug discovery," Biopolymers, vol. 47, pp. 197-223 (1998).

\* cited by examiner

FIG. 1A

| PEPTIDE | SEQUENCE | ANTIBODY DILUTIONS | | | | | | | |
|---|---|---|---|---|---|---|---|---|---|
| | | 1.00E+03 | 5.00E+03 | 1.00E+04 | 5.00E+04 | 1.00E+05 | 5.00E+05 | 1.00E+06 |
| Thr* | x-x-x-x-x-Thr*-x-x-x-x-x-Cys | 1.92 | 1.32 | 0.54 | 0.34 | 0.07 | 0.04 | 0.02 |
| Ser-Thr | x-x-x-x-x-Ser/Thr-x-x-x-x-x-Cys | 0.11 | 0.05 | 0.01 | 0.00 | 0.01 | 0.00 | 0.00 |
| Threonine* mix | 18 phospho-Thr peptide | 1.84 | 1.13 | 0.40 | 0.28 | 0.10 | 0.07 | 0.05 |
| Serine* mix | 38 phospho-Ser peptide | 0.12 | 0.04 | 0.02 | 0.02 | 0.02 | 0.01 | 0.00 |
| Abi-Thr109-P | Ser-Lys-Asp-Gly-Ala-Thr-Met-Lys-Thr*-Phe-Cys-Gly-Thr-Pro (SEQ ID NO:1) | 1.18 | 0.95 | 0.34 | 0.13 | 0.03 | 0.01 | 0.03 |
| APP1-Thr668-P | Asp-Ala-Val-Thr-Pro-Lys-Lys-Arg-His-Leu-Ser-Lys-Cys (SEQ ID NO:2) | 0.14 | 0.03 | 0.01 | 0.01 | 0.01 | 0.01 | 0.00 |
| C8# | Asp-Thr-Gln-Ile-Lys-Arg-Asn-Thr*-Phe-Val-Gly-Thr-Pro-Phe-Cys (SEQ ID NO:3) | 1.71 | 1.13 | 0.39 | 0.22 | 0.03 | 0.02 | 0.02 |
| CaK-Thr167-P | His-Gln-Val-Thr-Arg-Thr*-Pro-Arg-Cys (SEQ ID NO:4) | 1.77 | 1.15 | 0.41 | 0.27 | 0.06 | 0.03 | 0.01 |
| CaMIV-Thr189-P | His-Gln-Val-Leu-Met-Lys-Thr*-Val-Cys-Gly (SEQ ID NO:5) | 1.79 | 1.38 | 0.85 | 0.40 | 0.09 | 0.05 | 0.01 |
| CDC2-Thr187-P | Ile-Pro-Leu-Arg-Val-Tyr-Thr*-His-Glu-Val-Val-Thr-Leu-Cys | 1.02 | 0.58 | 0.14 | 0.08 | 0.03 | 0.01 | 0.01 |
| CDK2-Thr139-P | Gly-Val-Pro-Val-Arg-Thr-Thr*-His-Glu-Val-Val-Thr-Leu-Cys (SEQ ID NO:7) | 1.86 | 1.79 | 0.51 | 0.44 | 0.08 | 0.04 | 0.02 |
| p70S6K-Thr368-P | Asn-Gly-Val-Pro-Leu-Gly-Phe-Thr*-Tyr-Val-Ala-Pro-Lys-Cys (SEQ ID NO:8) | 1.99 | 1.44 | 0.62 | 0.38 | 0.09 | 0.04 | 0.01 |
| PKCalpha-P | Lys-Glu-His-Ala-Met-Met-Gly-Val-Thr-Thr-Arg-Thr-Phe-Cys (SEQ ID NO:9) | 1.82 | 1.63 | 0.94 | 0.58 | 0.18 | 0.09 | 0.02 |
| ERK2-P | Asp-His-Thr-Gly-Phe-Leu-Thr*-Glu-Tyr-Val-Ala-Thr-Arg-Trp-Cys (SEQ ID NO:10) | 1.58 | 1.18 | 0.51 | 0.20 | 0.07 | 0.04 | 0.02 |
| Myc-Ser62/62-P | Glu-Leu-Leu-Pro-Thr-Pro-Pro-Leu-Ser-Pro-Ser-Arg-Arg-Ser-Cys (SEQ ID NO:11) | 0.11 | 0.06 | 0.03 | 0.02 | 0.02 | 0.02 | 0.02 |
| P38-2P | Leu-Ala-Arg-His-Thr-Asp-Asp-Glu-Met-Thr-Gly-Tyr-Val-Ala-Thr-Arg-Cys (SEQ ID NO:12) | 0.54 | 0.30 | 0.08 | 0.03 | 0.04 | 0.04 | 0.02 |
| JBK-2P | Ser-Phe-Met-Met-Thr-Pro-Tyr*-Val-Val-Thr-Arg-Tyr-Arg-Cys (SEQ ID NO:13) | 1.49 | 0.44 | 0.12 | 0.07 | 0.03 | 0.02 | 0.02 |

FIG. 1B

| PEPTIDE SEQUENCE | | phospho-Thr Reactivity |
|---|---|---|
| XXXXXXS*XXXXXX | | — |
| XXXXY*XXXX | | — |
| XXXXXPXS*/T*PXR/KXXX | (SEQ ID NO:14) | + + |
| XXXXRSXS*XPXXXX | (SEQ ID NO:15) | — |
| XXXXRSXSXPXXXX | (SEQ ID NO:16) | — |
| XXXXXPXS*/T*PXXXXX | (SEQ ID NO:17) | + + |
| XXXXXPXS/TPXXXXX | (SEQ ID NO:18) | — |
| XXXXXT*XXXXXX | | + + + |
| XXXXXXS/TXXXXXX | | — |
| 21 phospho-Thr peptides mixture | | + + + |
| 38 phospho-Ser peptides mixture | | — |
| 30 phospho-Tyr peptides mixture | | — |
| | | |
| NEB LIBRARY | | |
| X-X-X-X-D/E-X-X-S*-T*-X-X-X-X-X-C | (SEQ ID NO:19) | + + + |
| X-X-X-X-X-X-S*/T*-D/E-D/E-D/E-X-X-X | (SEQ ID NO:20) | + + |
| X-X-X-X-F-X-X-F-S*/T*-F/Y-X-X-X-X-C | (SEQ ID NO:21) | + + + |
| X-X-X-X-R/K-X-S*/T*-X-X-X-X-X-X-C | (SEQ ID NO:22) | + + + |
| X-X-X-R/K-X-X-S*/T*-X-X-X-X-X-X-C | (SEQ ID NO:23) | + + + |
| X-X-X-X-X-X-S*/T*-F/I/M-X-X-X-X-X-C | (SEQ ID NO:24) | + + + |
| X-X-X-X-X-X-S*/T*-F/I-X-X-X-X-X-C | (SEQ ID NO:25) | + + + |
| X-X-X-X-X-X-S*/T-P-X-X-X-X-X-X-C | (SEQ ID NO:26) | + + |
| X-X-X-X-X-T*-X-X-X-X-X-X-C | | + + + |
| X-X-X-X-X-P-X-S*/T*-P-X-X-X-X-X-C | (SEQ ID NO:27) | + + |
| X-X-X-X-X-X-S/T-X-X-X-X-X-X-C | (SEQ ID NO:28) | — |
| X-X-X-X-X-P-X-S*/T*-P-X-R/K-X-X-X-C | (SEQ ID NO:29) | + + |

| ANTIBODY REACTIVITY | | ELISA O.D. |
|---|---|---|
| + + + | very strong | > 2 |
| + + | strong | 1 - 2 |
| + | weak | 0.2 - 1 |
| − | very little | < 0.2 |

Figure 1c. Western analysis of cell extracts from RS 4;11 cells minus or plus okadaic acid treatment (lanes 1 and 2), nonphosphorylated and phosphorylated ERK protein (lanes 3 and 4), and nonphosphorylated and phosphorylated MKK3 protein (lanes 5 and 6) using phospho-threonine antibody.

FIG. 1D

| Fixed Amino Acid | -4 | -3 | -2 | -1 | S*/T* | +1 | +2 | +3 |
|---|---|---|---|---|---|---|---|---|
| Ala | +++ | +++ | +++ | +++ | | +++ | +++ | ++ |
| Cys | +++ | +++ | +++ | +++ | | +++ | +++ | ++ |
| Asp | +++ | +++ | +++ | +++ | | +++ | +++ | ++ |
| Glu | +++ | +++ | +++ | +++ | | +++ | +++ | ++ |
| Phe | +++ | +++ | +++ | +++ | | +++ | +++ | ++ |
| Gly | +++ | +++ | +++ | ++ | | +++ | +++ | ++ |
| His | +++ | +++ | +++ | +++ | | +++ | +++ | ++ |
| Ile | +++ | +++ | +++ | +++ | | +++ | +++ | ++ |
| Lys | +++ | +++ | +++ | +++ | | +++ | +++ | ++ |
| Leu | +++ | +++ | +++ | +++ | | +++ | +++ | ++ |
| Met | +++ | +++ | +++ | +++ | | +++ | +++ | ++ |
| Asn | +++ | ++ | +++ | +++ | | + | +++ | ++ |
| Pro | +++ | +++ | +++ | +++ | | − | +++ | ++ |
| Gln | +++ | +++ | +++ | +++ | | +++ | +++ | ++ |
| Arg | +++ | +++ | +++ | +++ | | +++ | +++ | ++ |
| Ser | +++ | +++ | +++ | + | | +++ | +++ | ++ |
| Thr | +++ | +++ | +++ | +++ | | +++ | +++ | ++ |
| Val | +++ | +++ | +++ | +++ | | +++ | +++ | ++ |
| Trp | ++ | ++ | ++ | ++ | | ++ | ++ | + |
| Tyr | ++ | ++ | ++ | ++ | | ++ | ++ | + |

Fixed AA position relative to phospho-Ser*/Thr*

−5−4−3−2−1 +1+2+3+4+5
XXXXX Ser*/Thr* XXXXX

FIG. 2A

| PEPTIDE | SEQUENCE | ANTIBODY DILUTIONS | | | | | |
|---|---|---|---|---|---|---|---|
| | | 1.00E+03 | 5.00E+03 | 1.00E+04 | 5.00E+04 | 1.00E+05 | 5.00E+05 | 1.00E+06 |
| PXSP-P | X-X-X-X-X-Pro-X-Ser*-Thr*-Pro-X-X-X-X-X-X-Cys (SEQ ID NO:27) | 1.82 | 1.97 | 1.74 | 1.40 | 0.70 | 0.35 | 0.08 |
| Threonine mix | 18 phospho-Thr peptide mix | 1.97 | 1.37 | 0.67 | 0.36 | 0.13 | 0.07 | 0.05 |
| Ser/Thr | X-X-X-X-X-X-Ser/Thr-X-X-X-X-X-X-Cys (SEQ ID NO:28) | 0.14 | 0.03 | 0.01 | 0.00 | 0.00 | 0.00 | 0.00 |
| RB Thr373-P | Val-Ile-Pro-Pro-His-Thr*-Pro-Val-Arg-Thr-Val-Met-Asn-Thr-Cys (SEQ ID NO:30) | 2.07 | 2.17 | 1.70 | 1.20 | 0.48 | 0.18 | 0.03 |
| MKK3-Thr-P | Ser-Val-Ala-Lys-Thr*-Met-Asp-Ala-Gly-Cys (SEQ ID NO:31) | 0.05 | 0.04 | 0.01 | 0.00 | 0.00 | 0.00 | 0.00 |
| PKCalpha-P | Lys-Glu-His-Met-Met-Asp-Gly-Val-Thr-Thr-Arg-Thr*-Phe-Cys (SEQ ID NO:9) | 0.05 | 0.02 | 0.01 | 0.00 | 0.01 | 0.00 | 0.00 |
| p70 S6K-Thr389 | Asn-Gln-Val-Phe-Leu-Gly-Phe-Thr*-Tyr-Val-Ala-Pro-Lys-Lys-Cys (SEQ ID NO:8) | 0.11 | 0.05 | 0.01 | 0.00 | 0.01 | 0.00 | 0.00 |
| cdk4-Thr172-P | Arg-Ile-Tyr-Ser-Tyr-Gln-Met-Ala-Leu-Thr*-Pro-Val-Val-Lys-Cys (SEQ ID NO:32) | 2.07 | 2.21 | 2.01 | 1.55 | 0.69 | 0.31 | 0.07 |

Figure 2b. Western analysis of cell extracts from RS 4;11 cells minus or plus okadaic acid (1 µM) treatment (lanes 1 and 2), nonphosphorylated and phosphorylated ATF-2 protein (lanes 3 and 4) using phospho-PXS*P antibody.

FIG. 3A

| PEPTIDE | SEQUENCE | ANTIBODY DILUTIONS | | | | | |
|---|---|---|---|---|---|---|---|
| | | 1.00E+03 | 5.00E+03 | 1.00E+04 | 5.00E+04 | 1.00E+05 | 5.00E+05 |
| 14-3-3 BM-P | X-X-X-X-Arg-Ser-X-Ser*-X-Pro-X-X-X-X-Cys (SEQ ID NO:133) | 2.41 | 2.15 | 1.49 | 1.15 | 0.44 | 0.25 |
| 14-3-3 BM | X-X-X-X-Arg-Ser-X-Ser-X-Pro-X-X-X-X-Cys (SEQ ID NO:134) | 0.07 | 0.03 | 0.02 | 0.03 | 0.02 | 0.03 |
| CDC25-Ser216-P | Gly-Leu-Tyr-Arg-Ser-Pro-Ser-Met-Pro-Glu-Asn-Leu-Asn-Arg-Cys (SEQ ID NO:35) | 2.35 | 2.08 | 1.49 | 1.05 | 0.33 | 0.18 |
| CDC25-Ser216 | Gly-Leu-Tyr-Arg-Ser-Pro-Ser-Met-Pro-Glu-Asn-Leu-Asn-Arg-Cys (SEQ ID NO:36) | 0.05 | 0.02 | 0.03 | 0.03 | 0.04 | 0.03 |
| Bad-Ser112-P | Thr-Arg-Ser-Arg-His-Ser-Ser-Tyr-Pro-Ala-Gly-Thr-Glu-Glu-Cys (SEQ ID NO:37) | 1.59 | 0.43 | 0.10 | 0.03 | 0.01 | 0.00 |
| Bad-Ser112 | Thr-Arg-Ser-Arg-His-Ser-Ser-Tyr-Pro-Ala-Gly-Thr-Glu-Glu-Cys (SEQ ID NO:38) | 0.00 | 0.00 | 0.00 | 0.00 | 0.00 | 0.00 |
| Bad-Ser136 | Phe-Arg-Gly-Arg-Ser-Arg-Ser-Ala-Pro-Pro-Asn-Leu-Trp-Ala-Cys (SEQ ID NO:39) | 0.03 | 0.00 | 0.00 | 0.00 | 0.00 | 0.00 |
| Bad-Ser136-P | Phe-Arg-Gly-Arg-Ser-Arg-Ser*-Ala-Pro-Pro-Asn-Leu-Trp-Ala-Cys (SEQ ID NO:40) | 3.25 | 1.86 | 0.73 | 0.51 | 0.07 | 0.03 |

Western Analysis using Phospho-RSXS*XP Ab (14-3-3-Ab)

Figure 3b. Western analysis of cell extracts from 293 cells transfected with GST-Bad and treated with TPA using phospho-14-3-3 binding motif antibody.

FIG. 4A

| PEPTIDE | SEQUENCE | MONOCLONAL ANTIBODIES | |
|---|---|---|---|
| | | 6B8 | 5A9 |
| Ser/ThrPro-P | x-x-x-x-x-x-Ser/Thr*-Pro-X-x-x-x-x-Cys (SEQ ID NO:26) | 1.774 | 0.731 |
| ProXSer/ThrPro-P | x-x-x-x-x-Pro-X-Ser/Thr*-Pro-X-x-x-x-x-Cys (SEQ ID NO:27) | 0.924 | 0.766 |
| ProXSer/ThrPro-P | x-x-x-x-x-Pro-X-Ser/Thr-Pro-X-x-x-x-x-Cys (SEQ ID NO:41) | 0.02 | 0.063 |
| ProXSer/ThrProXArg-P | x-x-x-x-x-Pro-X-Ser/Thr*-Pro-X-Arg/Lys-X-X-X-Cys (SEQ ID NO:42) | 1.955 | 1.275 |
| Thr-P | x-x-x-x-x-x-Thr*-x-x-x-x-x-x-Cys | 0 | -- |
| Ser-P | x-x-x-x-x-x-Ser*-x-x-x-x-x-x-Cys | 0.031 | 0.088 |
| Ser/Thr | x-x-x-x-x-x-Ser/Thr-x-x-x-x-x-x-Cys | 0.021 | 0.066 |
| Tyr-P | x-x-x-x-x-x-Tyr*-x-x-x-x-x-x-Cys | 0.023 | 0.072 |
| Rb (Ser795)-P | Ser-Pro-Tyr-Lys-Phe-Pro-Ser-Ser*-Pro-Leu-Arg-Ile-Pro-Gly-Cys (SEQ ID NO:43) | 0.032 | 0.124 |
| Rb (Thr373)-P | Val-Ile-Pro-Pro-His-Thr*-Pro-Val-Arg-Thr-Val-Met-Asn-Thr-Cys (SEQ ID NO:30) | 3.336 | 3.503 |
| Rb (Thr373) | Val-Ile-Pro-Pro-His-Thr-Pro-Val-Arg-Thr-Val-Met-Asn-Thr-Cys (SEQ ID NO:44) | 0.02 | 0.073 |

FIG. 4B
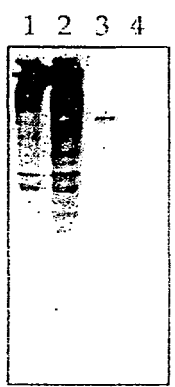
6B8
1 2 3 4
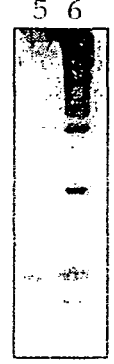
5A9
5 6
okadaic acid     − + − −  
phosphorylated RB   − − + −  
RB      − − − +
okadaic acid   − +

1 2 3 4

5 6 7 8

9 10 11 12

Signal to noise ratio of ELISA readings using phospho-Akt substrate antibody.

Western analysis of calyculin A-treated A431 cells using Phospho-Akt Substrate Antibody.

− +
calyculin A

Signal to noise ratio of ELISA reading using phospho-PKA substrates antibody.

Western analysis of
calyculin A-treated A431 cells
using Phospho-PKA Substrate
Antibody.

- + calyculin A

Western analysis of
A431 cell extracts

+ - + + - + - +  Cell Extracts
- - - + - - - -  PKI

Signal to noise ratio of ELISA reading using phospho-Serine/threonine phenylalanine antibody.

Western analysis of calyculin
A-treated A431 cells using phospho-
Serine/phenylalanine substrates antibody.

–   +
calyculin A

Signal to noise ratio of ELISA reading using a context-independent phospho-PKC consensus substrate motif antibody.

Western blot analysis using a context-independent phospho-PKC consensus substrate motif antibody.

Western blot analysis of whole cell lysates using a context-independent antibody specific for the phospho-PKC consensus substrate motif.

Western analysis of whole cell lysates using a phosphotyrosine and nitrotyrosine - specific context-independent antibodies.

Immunocytochemical staining of NIH/3T3 cells using a polyclonal context-independent antibody specific for nitrotyrosine (brown).

Phosphothreonine-X-arginine motif-specific context-independent antibody ELISAs.

(SEQ ID NO: 117) GLT*VK — c-Raf (T481)-P
(SEQ ID NO: 118) LAT*VK — Raf (T491)-P
(SEQ ID NO: 119) FFT*RH — PKC (Thr633)-P
(SEQ ID NO: 120) PLT*PR — ERF (Thr526)-P
(SEQ ID NO: 121) NVT*MR — Caspase-7 (Thr44)-P
(SEQ ID NO: 122) AVT*PK — APP1 (Thr668)-P Western blot analysis or Jurkat cell extracts using a context-independent antibody specific for the phosphothreonine-X-arginine motif.

IHC staining of proteins containing phosphorylated threonine-X-arginine motifs in human breast carcinoma.

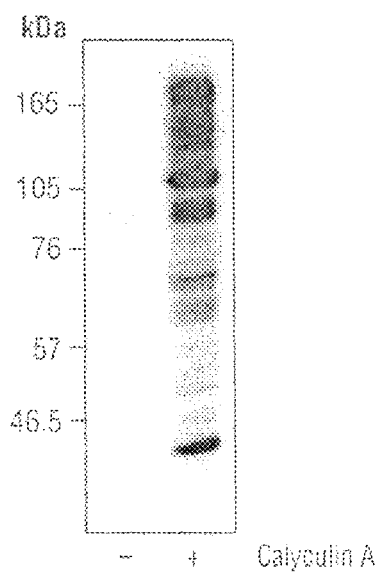

FIG. 23
Western blotting of COS cell extracts using a context-independent antibody specific for phospho-ATM/ATR consensus substrate motif.

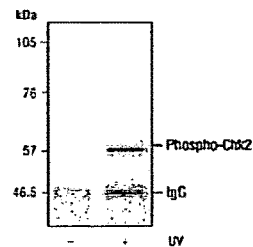

FIG. 24
Western blot analysis of UV treated COS cells, using a context-independent antibody specific for phospho-ATM/ATR consensus substrate motif.

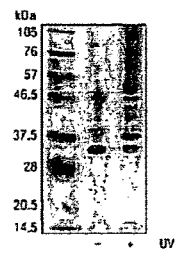

FIG. 25
Phospho-14-3-3 binding motif-specific, context-independent monoclonal antibody ELISAs (T* and S* denote phospho-threonine and serine).

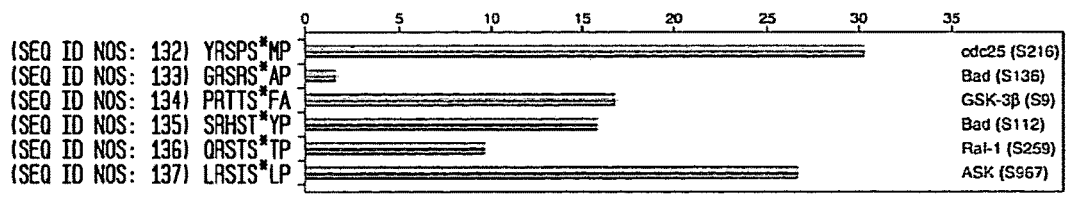

| | | |
|---|---|---|
| (SEQ ID NOS: 132) | YRSPS*MP | cdc25 (S216) |
| (SEQ ID NOS: 133) | GRSRS*AP | Bad (S136) |
| (SEQ ID NOS: 134) | PRTTS*FA | GSK-3β (S9) |
| (SEQ ID NOS: 135) | SRHST*YP | Bad (S112) |
| (SEQ ID NOS: 136) | QRSTS*TP | Raf-1 (S259) |
| (SEQ ID NOS: 137) | LRSIS*LP | ASK (S967) |

Western blot analysis of calyculin A treated A431 cells, using a context-independent antibodies specific for phospho-14-3-3 binding motif #1.

Phospho-PDK1 docking motif-specific, context-independent monoclonal antobody ELISAs.(T* and S* denote phospho-threonine and serine.)

Western blot analysis of extracts from A431 cells using a monoclonal context-independent antibody specific for the phospho-PDK1 docking motif.

Immunoprecipitation of extracts from NIH/3T3 cells using a monoclonal context-independent antibody specific for the phospho-PDK1 docking motif.

SEQUENCE LISTING

<160> NUMBER OF SEQ ID NOS: 317

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Thr

<400> SEQUENCE: 1

Ile Lys Asp Gly Ala Thr Met Lys Thr Phe Cys Gly Thr Pro
1               5                   10

-continued

```
<210> SEQ ID NO 2
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 2

Asp Ala Ala Val Thr Pro Lys Lys Arg His Leu Ser Lys Cys
1               5                   10

<210> SEQ ID NO 3
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Thr

<400> SEQUENCE: 3

Asp Thr Gln Ile Lys Arg Asn Thr Phe Val Gly Thr Pro Phe Cys
1               5                   10                  15

<210> SEQ ID NO 4
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 4

His Gln Val Val Thr Arg Trp Tyr Arg Cys
1               5                   10

<210> SEQ ID NO 5
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Thr

<400> SEQUENCE: 5

His Gln Val Leu Met Lys Thr Val Cys Gly
1               5                   10

<210> SEQ ID NO 6
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Thr

<400> SEQUENCE: 6

Ile Pro Ile Arg Val Tyr Thr His Glu Val Val Thr Leu Cys
1               5                   10

<210> SEQ ID NO 7
<211> LENGTH: 15
<212> TYPE: PRT
<213> ORGANISM: Homo sapiens
```

```
<220> FEATURE:
<221> NAME/KEY: MOD_RES
<222> LOCATION: (8)..(8)
<223> OTHER INFORMATION: Phosphorylated-Thr

<400> SEQUENCE: 7

Gly Val Pro Val Arg Thr Tyr Thr His Glu Val Val Thr Leu Cys
1               5                   10                  15

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Thr

<400> SEQUENCE: 8

Asn Gln Val Phe Leu Gly Phe Thr Tyr Val Ala Pro Lys Lys Cys
1               5                   10                  15

<210> SEQ ID NO 9
<211> LENGTH: 14
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Thr

<400> SEQUENCE: 9

Lys Glu His Met Met Asp Gly Val Thr Thr Arg Thr Phe Cys
1               5                   10

<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Thr
<220> FEATURE:
<221> NAME/KEY: MOD_RES
<222> LOCATION: (9)..(9)
<223> OTHER INFORMATION: Phosphorylated-Tyr

<400> SEQUENCE: 10

Asp His Thr Gly Phe Leu Thr Glu Tyr Val Ala Thr Arg Trp Cys
1               5                   10                  15

<210> SEQ ID NO 11
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr
<220> FEATURE:
<221> NAME/KEY: MOD_RES
<222> LOCATION: (9)..(9)
<223> OTHER INFORMATION: Phosphorylated-Ser

<400> SEQUENCE: 11

Glu Leu Leu Pro Thr Pro Pro Leu Ser Pro Ser Arg Arg Ser Cys
1               5                   10                  15
```

```
<210> SEQ ID NO 12
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr
<220> FEATURE:
<221> NAME/KEY: MOD_RES
<222> LOCATION: (12)..(12)
<223> OTHER INFORMATION: Phosphorylated-Tyr

<400> SEQUENCE: 12

Leu Ala Arg His Thr Asp Asp Glu Met Thr Gly Tyr Val Ala Thr Arg
1               5                   10                  15

Cys

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr
<220> FEATURE:
<221> NAME/KEY: MOD_RES
<222> LOCATION: (7)..(7)
<223> OTHER INFORMATION: Phosphorylated-Tyr

<400> SEQUENCE: 13

Ser Phe Met Met Thr Pro Tyr Val Val Thr Arg Tyr Tyr Arg Cys
1               5                   10                  15

<210> SEQ ID NO 14
<211> LENGTH: 14
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphoserine or Phosphothreonine
<220> FEATURE:
<221> NAME/KEY: MOD_RES
<222> LOCATION: (10)..(10)
<223> OTHER INFORMATION: Any one of the 20 amino acids except Cys
<220> FEATURE:
<221> NAME/KEY: MOD_RES
<222> LOCATION: (11)..(11)
<223> OTHER INFORMATION: Arg or Lys
<220> FEATURE:
<221> NAME/KEY: MOD_RES
<222> LOCATION: (12)..(14)
<223> OTHER INFORMATION: Any one of the 20 amino acids except Cys

<400> SEQUENCE: 14

Xaa Xaa Xaa Xaa Xaa Pro Xaa Xaa Pro Xaa Xaa Xaa Xaa Xaa
1               5                   10

<210> SEQ ID NO 15
<211> LENGTH: 14
<212> TYPE: PRT
<213> ORGANISM: Homo sapiens
```

```
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphorylated-Ser
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (11)..(14)
<223> OTHER INFORMATION: Any one of the 20 amino acids except Cys

<400> SEQUENCE: 15

Xaa Xaa Xaa Xaa Arg Ser Xaa Ser Xaa Pro Xaa Xaa Xaa Xaa
1               5                   10

<210> SEQ ID NO 16
<211> LENGTH: 14
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (11)..(14)
<223> OTHER INFORMATION: Any one of the 20 amino acids except Cys

<400> SEQUENCE: 16

Xaa Xaa Xaa Xaa Arg Ser Xaa Ser Xaa Pro Xaa Xaa Xaa Xaa
1               5                   10

<210> SEQ ID NO 17
<211> LENGTH: 14
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphoserine or Phosphothreonine
<220> FEATURE:
<221> NAME/KEY: MOD_RES
<222> LOCATION: (10)..(14)
<223> OTHER INFORMATION: Any one of the 20 amino acids except Cys

<400> SEQUENCE: 17

Xaa Xaa Xaa Xaa Xaa Pro Xaa Xaa Pro Xaa Xaa Xaa Xaa Xaa
1               5                   10
```

```
<210> SEQ ID NO 18
<211> LENGTH: 14
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(14)
<223> OTHER INFORMATION: Any one of the 20 amino acids except Cys

<400> SEQUENCE: 18

Xaa Xaa Xaa Xaa Xaa Pro Xaa Xaa Pro Xaa Xaa Xaa Xaa Xaa
1               5                   10

<210> SEQ ID NO 19
<211> LENGTH: 14
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (6)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphoserine or Phosphothreonine
<220> FEATURE:
<221> NAME/KEY: MOD_RES
<222> LOCATION: (9)..(13)
<223> OTHER INFORMATION: Any one of the 20 amino acids except Cys

<400> SEQUENCE: 19

Xaa Xaa Xaa Xaa Xaa Xaa Xaa Xaa Xaa Xaa Xaa Xaa Xaa Cys
1               5                   10

<210> SEQ ID NO 20
<211> LENGTH: 13
<212> TYPE: PRT
<213> ORGANISM: Homo sapiens
<220> FEATURE:
<221> NAME/KEY: MOD_RES
<222> LOCATION: (1)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Phosphoserine or Phosphothreonine
<220> FEATURE:
<221> NAME/KEY: MOD_RES
<222> LOCATION: (8)..(10)
<223> OTHER INFORMATION: Asp or Glu
<220> FEATURE:
<221> NAME/KEY: MOD_RES
<222> LOCATION: (11)..(13)
```

```
<223> OTHER INFORMATION: Any one of the 20 amino acids except Cys

<400> SEQUENCE: 20

Xaa Xaa Xaa Xaa Xaa Xaa Xaa Xaa Xaa Xaa Xaa Xaa Xaa
1               5                   10

<210> SEQ ID NO 21
<211> LENGTH: 15
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (6)..(7)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Phosphoserine or Phosphothreonine
<220> FEATURE:
<221> NAME/KEY: MOD_RES
<222> LOCATION: (10)..(10)
<223> OTHER INFORMATION: Phe or Tyr
<220> FEATURE:
<221> NAME/KEY: MOD_RES
<222> LOCATION: (11)..(14)
<223> OTHER INFORMATION: Any one of the 20 amino acids except Cys

<400> SEQUENCE: 21

Xaa Xaa Xaa Xaa Phe Xaa Xaa Phe Xaa Xaa Xaa Xaa Xaa Xaa Cys
1               5                   10                  15

<210> SEQ ID NO 22
<211> LENGTH: 14
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (6)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Phosphoserine or Phosphothreonine
<220> FEATURE:
<221> NAME/KEY: MOD_RES
<222> LOCATION: (8)..(13)
<223> OTHER INFORMATION: Any one of the 20 amino acids except Cys

<400> SEQUENCE: 22

Xaa Xaa Xaa Xaa Xaa Xaa Xaa Xaa Xaa Xaa Xaa Xaa Xaa Cys
1               5                   10

<210> SEQ ID NO 23
<211> LENGTH: 14
<212> TYPE: PRT
<213> ORGANISM: Homo sapiens
<220> FEATURE:
<221> NAME/KEY: MOD_RES
<222> LOCATION: (1)..(3)
<223> OTHER INFORMATION: Any one of the 20 amino acids except Cys
<220> FEATURE:
```

```
<221> NAME/KEY: MOD_RES
<222> LOCATION: (4)..(4)
<223> OTHER INFORMATION: Arg or Lys
<220> FEATURE:
<221> NAME/KEY: MOD_RES
<222> LOCATION: (5)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Phosphoserine or Phosphothreonine
<220> FEATURE:
<221> NAME/KEY: MOD_RES
<222> LOCATION: (8)..(13)
<223> OTHER INFORMATION: Any one of the 20 amino acids except Cys

<400> SEQUENCE: 23

Xaa Xaa Xaa Xaa Xaa Xaa Xaa Xaa Xaa Xaa Xaa Xaa Xaa Cys
1               5                   10

<210> SEQ ID NO 24
<211> LENGTH: 14
<212> TYPE: PRT
<213> ORGANISM: Homo sapiens
<220> FEATURE:
<221> NAME/KEY: MOD_RES
<222> LOCATION: (1)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Phosphoserine or Phosphothreonine
<220> FEATURE:
<221> NAME/KEY: MOD_RES
<222> LOCATION: (8)..(8)
<223> OTHER INFORMATION: Ile or Met
<220> FEATURE:
<221> NAME/KEY: MOD_RES
<222> LOCATION: (9)..(13)
<223> OTHER INFORMATION: Any one of the 20 amino acids except Cys

<400> SEQUENCE: 24

Xaa Xaa Xaa Xaa Xaa Xaa Xaa Xaa Xaa Xaa Xaa Xaa Xaa Cys
1               5                   10

<210> SEQ ID NO 25
<211> LENGTH: 14
<212> TYPE: PRT
<213> ORGANISM: Homo sapiens
<220> FEATURE:
<221> NAME/KEY: MOD_RES
<222> LOCATION: (1)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Phosphoserine or Phosphothreonine
<220> FEATURE:
<221> NAME/KEY: MOD_RES
<222> LOCATION: (8)..(8)
<223> OTHER INFORMATION: Phe or Ile
<220> FEATURE:
<221> NAME/KEY: MOD_RES
<222> LOCATION: (9)..(13)
<223> OTHER INFORMATION: Any one of the 20 amino acids except Cys

<400> SEQUENCE: 25

Xaa Xaa Xaa Xaa Xaa Xaa Xaa Xaa Xaa Xaa Xaa Xaa Xaa Cys
1               5                   10

<210> SEQ ID NO 26
<211> LENGTH: 15
<212> TYPE: PRT
```

```
<213> ORGANISM: Homo sapiens
<220> FEATURE:
<221> NAME/KEY: MOD_RES
<222> LOCATION: (1)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Phosphoserine or Phosphothreonine
<220> FEATURE:
<221> NAME/KEY: MOD_RES
<222> LOCATION: (9)..(14)
<223> OTHER INFORMATION: Any one of the 20 amino acids except Cys

<400> SEQUENCE: 26

Xaa Xaa Xaa Xaa Xaa Xaa Xaa Pro Xaa Xaa Xaa Xaa Xaa Xaa Cys
1               5                   10                  15

<210> SEQ ID NO 27
<211> LENGTH: 15
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphoserine or Phosphothreonine
<220> FEATURE:
<221> NAME/KEY: MOD_RES
<222> LOCATION: (10)..(14)
<223> OTHER INFORMATION: Any one of the 20 amino acids except Cys

<400> SEQUENCE: 27

Xaa Xaa Xaa Xaa Xaa Pro Xaa Xaa Pro Xaa Xaa Xaa Xaa Xaa Cys
1               5                   10                  15

<210> SEQ ID NO 28
<211> LENGTH: 14
<212> TYPE: PRT
<213> ORGANISM: Homo sapiens
<220> FEATURE:
<221> NAME/KEY: MOD_RES
<222> LOCATION: (1)..(6)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(13)
<223> OTHER INFORMATION: Any one of the 20 amino acids except Cys

<400> SEQUENCE: 28

Xaa Xaa Xaa Xaa Xaa Xaa Xaa Xaa Xaa Xaa Xaa Xaa Xaa Cys
1               5                   10

<210> SEQ ID NO 29
<211> LENGTH: 15
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
```

```
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphoserine or Phosphothreonine
<220> FEATURE:
<221> NAME/KEY: MOD_RES
<222> LOCATION: (10)..(10)
<223> OTHER INFORMATION: Any one of the 20 amino acids except Cys
<220> FEATURE:
<221> NAME/KEY: MOD_RES
<222> LOCATION: (11)..(11)
<223> OTHER INFORMATION: Arg or Lys
<220> FEATURE:
<221> NAME/KEY: MOD_RES
<222> LOCATION: (12)..(14)
<223> OTHER INFORMATION: Any one of the 20 amino acids except Cys

<400> SEQUENCE: 29

Xaa Xaa Xaa Xaa Xaa Pro Xaa Xaa Pro Xaa Xaa Xaa Xaa Xaa Cys
1               5                   10                  15

<210> SEQ ID NO 30
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 30

Val Ile Pro Pro His Thr Pro Val Arg Thr Val Met Asn Thr Cys
1               5                   10                  15

<210> SEQ ID NO 31
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 31

Ser Val Ala Lys Thr Met Asp Ala Gly Cys
1               5                   10

<210> SEQ ID NO 32
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 32

Arg Ile Tyr Ser Tyr Gln Met Ala Leu Thr Pro Val Val Val Lys Cys
1               5                   10                  15

<210> SEQ ID NO 33
<211> LENGTH: 15
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
```

```
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphorylated-Ser
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (11)..(14)
<223> OTHER INFORMATION: Any one of the 20 amino acids except Cys

<400> SEQUENCE: 33

Xaa Xaa Xaa Xaa Arg Ser Xaa Ser Xaa Pro Xaa Xaa Xaa Xaa Cys
1               5                   10                  15

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (11)..(14)
<223> OTHER INFORMATION: Any one of the 20 amino acids except Cys

<400> SEQUENCE: 34

Xaa Xaa Xaa Xaa Arg Ser Xaa Ser Xaa Pro Xaa Xaa Xaa Xaa Cys
1               5                   10                  15

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 35

Gly Leu Tyr Arg Ser Pro Ser Met Pro Glu Asn Leu Asn Arg Cys
1               5                   10                  15

<210> SEQ ID NO 36
<211> LENGTH: 15
<212> TYPE: PRT
<213> ORGANISM: Homo sapiens

<400> SEQUENCE: 36

Gly Leu Tyr Arg Ser Pro Ser Met Pro Glu Asn Leu Asn Arg Cys
1               5                   10                  15

<210> SEQ ID NO 37
<211> LENGTH: 15
<212> TYPE: PRT
```

```
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 37

Thr Arg Ser Arg His Ser Ser Tyr Pro Ala Gly Thr Glu Glu Cys
1               5                   10                  15

<210> SEQ ID NO 38
<211> LENGTH: 15
<212> TYPE: PRT
<213> ORGANISM: Homo sapiens

<400> SEQUENCE: 38

Thr Arg Ser Arg His Ser Ser Tyr Pro Ala Gly Thr Glu Glu Cys
1               5                   10                  15

<210> SEQ ID NO 39
<211> LENGTH: 15
<212> TYPE: PRT
<213> ORGANISM: Homo sapiens

<400> SEQUENCE: 39

Phe Arg Gly Arg Ser Arg Ser Ala Pro Pro Asn Leu Trp Ala Cys
1               5                   10                  15

<210> SEQ ID NO 40
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 40

Phe Arg Gly Arg Ser Arg Ser Ala Pro Pro Asn Leu Trp Ala Cys
1               5                   10                  15

<210> SEQ ID NO 41
<211> LENGTH: 15
<212> TYPE: PRT
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(14)
<223> OTHER INFORMATION: Any one of the 20 amino acids except Cys

<400> SEQUENCE: 41

Xaa Xaa Xaa Xaa Xaa Pro Xaa Xaa Pro Xaa Xaa Xaa Xaa Xaa Cys
1               5                   10                  15

<210> SEQ ID NO 42
<211> LENGTH: 15
<212> TYPE: PRT
```

```
<213> ORGANISM: Homo sapiens
<220> FEATURE:
<221> NAME/KEY: MOD_RES
<222> LOCATION: (1)..(5)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphoserine or Phosphothreonine
<220> FEATURE:
<221> NAME/KEY: MOD_RES
<222> LOCATION: (10)..(10)
<223> OTHER INFORMATION: Any one of the 20 amino acids except Cys
<220> FEATURE:
<221> NAME/KEY: MOD_RES
<222> LOCATION: (11)..(11)
<223> OTHER INFORMATION: Arg or Lys
<220> FEATURE:
<221> NAME/KEY: MOD_RES
<222> LOCATION: (12)..(14)
<223> OTHER INFORMATION: Any one of the 20 amino acids except Cys

<400> SEQUENCE: 42

Xaa Xaa Xaa Xaa Xaa Pro Xaa Xaa Pro Xaa Xaa Xaa Xaa Xaa Cys
1               5                   10                  15

<210> SEQ ID NO 43
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 43

Ser Pro Tyr Lys Phe Pro Ser Ser Pro Leu Arg Ile Pro Gly Cys
1               5                   10                  15

<210> SEQ ID NO 44
<211> LENGTH: 15
<212> TYPE: PRT
<213> ORGANISM: Homo sapiens

<400> SEQUENCE: 44

Val Ile Pro Pro His Thr Pro Val Arg Thr Val Met Asn Thr Cys
1               5                   10                  15

<210> SEQ ID NO 45
<211> LENGTH: 14
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys
<220> FEATURE:
<221> NAME/KEY: MOD_RES
<222> LOCATION: (6)..(6)
<223> OTHER INFORMATION: Any one of the 20 amino acids except Cys
<220> FEATURE:
<221> NAME/KEY: MOD_RES
<222> LOCATION: (8)..(9)
<223> OTHER INFORMATION: Any one of the 20 amino acids except Cys
<220> FEATURE:
<221> NAME/KEY: MOD_RES
<222> LOCATION: (10)..(10)
<223> OTHER INFORMATION: Phosphorylated-Thr
<220> FEATURE:
```

```
<221> NAME/KEY: MOD_RES
<222> LOCATION: (11)..(14)
<223> OTHER INFORMATION: Any one of the 20 amino acids except Cys

<400> SEQUENCE: 45

Cys Xaa Xaa Xaa Arg Xaa Arg Xaa Xaa Thr Xaa Xaa Xaa Xaa
1               5                   10

<210> SEQ ID NO 46
<211> LENGTH: 14
<212> TYPE: PRT
<213> ORGANISM: Homo sapiens
<220> FEATURE:
<221> NAME/KEY: MOD_RES
<222> LOCATION: (2)..(6)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (10)..(10)
<223> OTHER INFORMATION: Phosphorylated-Thr
<220> FEATURE:
<221> NAME/KEY: MOD_RES
<222> LOCATION: (11)..(14)
<223> OTHER INFORMATION: Any one of the 20 amino acids except Cys

<400> SEQUENCE: 46

Cys Xaa Xaa Xaa Xaa Xaa Arg Arg Xaa Thr Xaa Xaa Xaa Xaa
1               5                   10

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Any one of the 20 amino acids except Cys
<220> FEATURE:
<221> NAME/KEY: MOD_RES
<222> LOCATION: (6)..(7)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Phosphoserine or Phosphothreonine
<220> FEATURE:
<221> NAME/KEY: MOD_RES
<222> LOCATION: (10)..(10)
<223> OTHER INFORMATION: Phe or Tyr
<220> FEATURE:
<221> NAME/KEY: MOD_RES
<222> LOCATION: (11)..(14)
<223> OTHER INFORMATION: Any one of the 20 amino acids except Cys

<400> SEQUENCE: 47

Xaa Xaa Xaa Xaa Phe Xaa Xaa Phe Xaa Xaa Xaa Xaa Xaa Xaa Cys
1               5                   10                  15

<210> SEQ ID NO 48
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 48
```

Arg Gln Arg Ser Thr Ser Thr Pro
1               5

<210> SEQ ID NO 49
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 49

Lys Gly Arg Thr Trp Thr Leu Cys
1               5

<210> SEQ ID NO 50
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 50

Arg Pro Arg Thr Thr Ser Phe Ala
1               5

<210> SEQ ID NO 51
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 51

Arg Arg Arg Thr Ser Ser Phe Ala
1               5

<210> SEQ ID NO 52
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 52

Arg Arg Arg Ala Ala Ser Met Asp
1               5

<210> SEQ ID NO 53
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 53

Arg Ile Arg Thr Gln Ser Phe Ser
1               5

```
<210> SEQ ID NO 54
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 54

Arg Glu Arg Lys Arg Thr Val Trp
1               5

<210> SEQ ID NO 55
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 55

Lys Asp Arg Gln Gly Thr His Lys
1               5

<210> SEQ ID NO 56
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 56

Arg Asp Arg Asn Gly Thr His Leu
1               5

<210> SEQ ID NO 57
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 57

Lys Leu Arg Leu Ser Thr Asp Tyr
1               5

<210> SEQ ID NO 58
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 58

Arg Asp Lys Ser Val Thr Asp Ser
1               5

<210> SEQ ID NO 59
<211> LENGTH: 8
<212> TYPE: PRT
<213> ORGANISM: Homo sapiens
```

```
<220> FEATURE:
<221> NAME/KEY: MOD_RES
<222> LOCATION: (6)..(6)
<223> OTHER INFORMATION: Phosphorylated-Ser

<400> SEQUENCE: 59

Arg Leu Arg Lys Ser Ser Ser Tyr
1               5

<210> SEQ ID NO 60
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 60

Arg Pro Arg Ser Cys Thr Trp Pro
1               5

<210> SEQ ID NO 61
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 61

Arg Arg Arg Ala Ala Ser Met Asp
1               5

<210> SEQ ID NO 62
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 62

Arg Phe Phe Thr Arg
1               5

<210> SEQ ID NO 63
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 63

Arg Thr Tyr Thr Leu
1               5

<210> SEQ ID NO 64
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr
```

<400> SEQUENCE: 64

Lys Arg Ser Thr Met
1               5

<210> SEQ ID NO 65
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 65

Arg Arg Arg Ser Ser
1               5

<210> SEQ ID NO 66
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 66

Arg Arg Pro Ser Tyr
1               5

<210> SEQ ID NO 67
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 67

Arg Thr Tyr Thr His
1               5

<210> SEQ ID NO 68
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 68

Arg Ser Pro Ser Met
1               5

<210> SEQ ID NO 69
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 69

Arg Lys Arg Thr Val

<210> SEQ ID NO 70
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 70

Arg Gln Gly Thr His
1               5

<210> SEQ ID NO 71
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 71

Arg Ser Leu Thr Glu
1               5

<210> SEQ ID NO 72
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 72

Arg Gln Glu Thr Val
1               5

<210> SEQ ID NO 73
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 73

Arg Ala Tyr Thr His
1               5

<210> SEQ ID NO 74
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 74

Lys Arg Asp Thr Phe
1               5

<210> SEQ ID NO 75

```
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 75

Lys Ser Val Thr Asp
1               5

<210> SEQ ID NO 76
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 76

Arg Lys Ser Ser Ser
1               5

<210> SEQ ID NO 77
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 77

Arg Ser Cys Thr Tyr
1               5

<210> SEQ ID NO 78
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 78

Phe Phe Thr Arg His
1               5

<210> SEQ ID NO 79
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 79

Thr Trp Thr Leu Cys
1               5

<210> SEQ ID NO 80
<211> LENGTH: 5
<212> TYPE: PRT
<213> ORGANISM: Homo sapiens
<220> FEATURE:
```

```
<221> NAME/KEY: MOD_RES
<222> LOCATION: (3)..(3)
<223> OTHER INFORMATION: Phosphorylated-Ser

<400> SEQUENCE: 80

Gln Arg Ser Phe Val
1               5

<210> SEQ ID NO 81
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 81

Ala Tyr Ser Phe Cys
1               5

<210> SEQ ID NO 82
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 82

Gly Tyr Ser Phe Val
1               5

<210> SEQ ID NO 83
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 83

Thr Thr Ser Phe Ala
1               5

<210> SEQ ID NO 84
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 84

Thr Ser Ser Phe Ala
1               5

<210> SEQ ID NO 85
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr
```

```
<400> SEQUENCE: 85

Val Tyr Thr His Glu
1               5

<210> SEQ ID NO 86
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 86

Thr Tyr Thr His Glu
1               5

<210> SEQ ID NO 87
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 87

Ala Tyr Thr His Gln
1               5

<210> SEQ ID NO 88
<211> LENGTH: 15
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys and
      Trp
<220> FEATURE:
<221> NAME/KEY: MOD_RES
<222> LOCATION: (6)..(6)
<223> OTHER INFORMATION: Any one of the 20 amino acids except Cys and
      Trp
<220> FEATURE:
<221> NAME/KEY: MOD_RES
<222> LOCATION: (8)..(8)
<223> OTHER INFORMATION: Any one of the 20 amino acids except Cys and
      Trp and is biased 50% to Thr
<220> FEATURE:
<221> NAME/KEY: MOD_RES
<222> LOCATION: (9)..(9)
<223> OTHER INFORMATION: Any one of the 20 amino acids except Cys and
      Trp
<220> FEATURE:
<221> NAME/KEY: MOD_RES
<222> LOCATION: (10)..(10)
<223> OTHER INFORMATION: Phosphorylated-Thr
<220> FEATURE:
<221> NAME/KEY: MOD_RES
<222> LOCATION: (11)..(11)
<223> OTHER INFORMATION: Any one of the 20 amino acids except Cys and
      Trp and is biased 50% to Phe
<220> FEATURE:
<221> NAME/KEY: MOD_RES
<222> LOCATION: (12)..(12)
<223> OTHER INFORMATION: Any one of the 20 amino acids except Cys and
      Trp and is biased 50% to Gly
<220> FEATURE:
<221> NAME/KEY: MOD_RES
<222> LOCATION: (13)..(15)
<223> OTHER INFORMATION: Any one of the 20 amino acids except Cys and
      Trp
```

<400> SEQUENCE: 88

Cys Xaa Xaa Xaa Arg Xaa Arg Xaa Xaa Thr Xaa Xaa Xaa Xaa Xaa
1               5                   10                  15

<210> SEQ ID NO 89
<211> LENGTH: 13
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys, Trp
      or Tyr
<220> FEATURE:
<221> NAME/KEY: MOD_RES
<222> LOCATION: (5)..(6)
<223> OTHER INFORMATION: Lys or Arg
<220> FEATURE:
<221> NAME/KEY: MOD_RES
<222> LOCATION: (7)..(7)
<223> OTHER INFORMATION: Phosphorylated-Ser
<220> FEATURE:
<221> NAME/KEY: MOD_RES
<222> LOCATION: (8)..(8)
<223> OTHER INFORMATION: Phe, Leu or Val
<220> FEATURE:
<221> NAME/KEY: MOD_RES
<222> LOCATION: (9)..(10)
<223> OTHER INFORMATION: Lys or Arg
<220> FEATURE:
<221> NAME/KEY: MOD_RES
<222> LOCATION: (11)..(13)
<223> OTHER INFORMATION: Any one of the 20 amino acids except Cys, Trp
      or Tyr

<400> SEQUENCE: 89

Cys Xaa Xaa Xaa Xaa Xaa Ser Xaa Xaa Xaa Xaa Xaa Xaa
1               5                   10

<210> SEQ ID NO 90
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (5)..(5)
<223> OTHER INFORMATION: Phosphorylated-Ser
<220> FEATURE:
<221> NAME/KEY: MOD_RES
<222> LOCATION: (6)..(6)
<223> OTHER INFORMATION: Variable amino acid

<400> SEQUENCE: 90

Arg Xaa Xaa Xaa Ser Xaa Pro
1               5

<210> SEQ ID NO 91
<211> LENGTH: 14
<212> TYPE: PRT
<213> ORGANISM: Homo sapiens

```
<220> FEATURE:
<221> NAME/KEY: MOD_RES
<222> LOCATION: (1)..(3)
<223> OTHER INFORMATION: Any one of the 20 amino acids except Cys
<220> FEATURE:
<221> NAME/KEY: MOD_RES
<222> LOCATION: (5)..(5)
<223> OTHER INFORMATION: Any one of the 20 amino acids except Cys
<220> FEATURE:
<221> NAME/KEY: MOD_RES
<222> LOCATION: (6)..(6)
<223> OTHER INFORMATION: Phe or Tyr
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphorylated-Ser
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (11)..(13)
<223> OTHER INFORMATION: Any one of the 20 amino acids except Cys

<400> SEQUENCE: 91

Xaa Xaa Xaa Arg Xaa Xaa Xaa Ser Xaa Pro Xaa Xaa Xaa Cys
1               5                   10

<210> SEQ ID NO 92
<211> LENGTH: 16
<212> TYPE: PRT
<213> ORGANISM: Homo sapiens
<220> FEATURE:
<221> NAME/KEY: MOD_RES
<222> LOCATION: (2)..(7)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Phosphorylated-Thr
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(16)
<223> OTHER INFORMATION: Any one of the 20 amino acids except Cys

<400> SEQUENCE: 92

Cys Xaa Xaa Xaa Xaa Xaa Xaa Leu Thr Gln Xaa Xaa Xaa Xaa Xaa Xaa
1               5                   10                  15

<210> SEQ ID NO 93
<211> LENGTH: 16
<212> TYPE: PRT
<213> ORGANISM: Homo sapiens
<220> FEATURE:
<221> NAME/KEY: MOD_RES
<222> LOCATION: (2)..(7)
<223> OTHER INFORMATION: Any one of the 20 amino acids except Cys
<220> FEATURE:
<221> NAME/KEY: MOD_RES
<222> LOCATION: (9)..(9)
<223> OTHER INFORMATION: Phosphorylated-Ser
<220> FEATURE:
<221> NAME/KEY: MOD_RES
<222> LOCATION: (11)..(11)
<223> OTHER INFORMATION: Asp or Glu
<220> FEATURE:
```

```
<221> NAME/KEY: MOD_RES
<222> LOCATION: (12)..(16)
<223> OTHER INFORMATION: Any one of the 20 amino acids except Cys

<400> SEQUENCE: 93

Cys Xaa Xaa Xaa Xaa Xaa Leu Ser Gln Xaa Xaa Xaa Xaa Xaa Xaa
 1               5                  10                  15

<210> SEQ ID NO 94
<211> LENGTH: 13
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys
<220> FEATURE:
<221> NAME/KEY: MOD_RES
<222> LOCATION: (7)..(7)
<223> OTHER INFORMATION: Any one of the 20 amino acids except Cys
<220> FEATURE:
<221> NAME/KEY: MOD_RES
<222> LOCATION: (8)..(8)
<223> OTHER INFORMATION: Phosphorylated-Ser
<220> FEATURE:
<221> NAME/KEY: MOD_RES
<222> LOCATION: (9)..(9)
<223> OTHER INFORMATION: Any one of the 20 amino acids except Cys
<220> FEATURE:
<221> NAME/KEY: MOD_RES
<222> LOCATION: (11)..(13)
<223> OTHER INFORMATION: Any one of the 20 amino acids except Cys

<400> SEQUENCE: 94

Cys Xaa Xaa Xaa Arg Ser Xaa Ser Xaa Pro Xaa Xaa Xaa
 1               5                  10

<210> SEQ ID NO 95
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Phosphorylated-Thr

<400> SEQUENCE: 95

Phe Xaa Arg Xaa Xaa Thr Phe Phe
 1               5

<210> SEQ ID NO 96
<211> LENGTH: 17
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any one of the 20 amino acids except Cys and
      Trp
<220> FEATURE:
<221> NAME/KEY: MOD_RES
<222> LOCATION: (3)..(4)
<223> OTHER INFORMATION: Any one of the 20 amino acids except Cys and
      Trp and is biased 50% to Arg
<220> FEATURE:
```

```
<221> NAME/KEY: MOD_RES
<222> LOCATION: (6)..(6)
<223> OTHER INFORMATION: Any one of the 20 amino acids except Cys and
      Trp and is biased 50% to Lys
<220> FEATURE:
<221> NAME/KEY: MOD_RES
<222> LOCATION: (8)..(8)
<223> OTHER INFORMATION: Any one of the 20 amino acids except Cys and
      Trp and is biased 50% to Gln
<220> FEATURE:
<221> NAME/KEY: MOD_RES
<222> LOCATION: (9)..(9)
<223> OTHER INFORMATION: Any one of the 20 amino acids except Cys and
      Trp and is biased 50% to Gly
<220> FEATURE:
<221> NAME/KEY: MOD_RES
<222> LOCATION: (10)..(10)
<223> OTHER INFORMATION: Phosphorylated-Thr
<220> FEATURE:
<221> NAME/KEY: MOD_RES
<222> LOCATION: (13)..(13)
<223> OTHER INFORMATION: Any one of the 20 amino acids except Cys and
      Trp and is biased 50% to Tyr
<220> FEATURE:
<221> NAME/KEY: MOD_RES
<222> LOCATION: (14)..(15)
<223> OTHER INFORMATION: Any one of the 20 amino acids except Cys and
      Trp and is biased 50% to Phe
<220> FEATURE:
<221> NAME/KEY: MOD_RES
<222> LOCATION: (16)..(17)
<223> OTHER INFORMATION: Any one of the 20 amino acids except Cys and
      Trp

<400> SEQUENCE: 96

Cys Xaa Xaa Xaa Phe Xaa Arg Xaa Xaa Thr Phe Phe Xaa Xaa Xaa Xaa
1               5                   10                  15

Xaa

<210> SEQ ID NO 97
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr
<220> FEATURE:
<221> NAME/KEY: MOD_RES
<222> LOCATION: (5)..(5)
<223> OTHER INFORMATION: Variable amino acid

<400> SEQUENCE: 97

Val Ile Tyr Ala Xaa Pro
1               5

<210> SEQ ID NO 98
<211> LENGTH: 15
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any one of the 20 amino acids except Cys and
      Trp
<220> FEATURE:
<221> NAME/KEY: MOD_RES
<222> LOCATION: (4)..(4)
<223> OTHER INFORMATION: Any one of the 20 amino acids except Cys and
      Trp and is biased 50% to Ala
<220> FEATURE:
<221> NAME/KEY: MOD_RES
<222> LOCATION: (5)..(5)
<223> OTHER INFORMATION: Any one of the 20 amino acids except Cys and
```

```
                Trp
<220> FEATURE:
<221> NAME/KEY: MOD_RES
<222> LOCATION: (8)..(8)
<223> OTHER INFORMATION: Phosphorylated-Tyr
<220> FEATURE:
<221> NAME/KEY: MOD_RES
<222> LOCATION: (10)..(10)
<223> OTHER INFORMATION: Any one of the 20 amino acids except Cys and
      Trp and is biased 50% to Ala
<220> FEATURE:
<221> NAME/KEY: MOD_RES
<222> LOCATION: (12)..(12)
<223> OTHER INFORMATION: Any one of the 20 amino acids except Cys and
      Trp and is biased 50% to Phe
<220> FEATURE:
<221> NAME/KEY: MOD_RES
<222> LOCATION: (13)..(15)
<223> OTHER INFORMATION: Any one of the 20 amino acids except Cys and
      Trp

<400> SEQUENCE: 98

Cys Xaa Xaa Xaa Xaa Val Ile Tyr Ala Xaa Pro Xaa Xaa Xaa Xaa
1               5                   10                  15

<210> SEQ ID NO 99
<211> LENGTH: 9
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (5)..(5)
<223> OTHER INFORMATION: Phosphorylated-Thr
<220> FEATURE:
<221> NAME/KEY: MOD_RES
<222> LOCATION: (7)..(7)
<223> OTHER INFORMATION: Variable amino acid

<400> SEQUENCE: 99

Lys Xaa Xaa Xaa Thr Pro Xaa His Arg
1               5

<210> SEQ ID NO 100
<211> LENGTH: 14
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any one of the 20 amino acids except Cys and
      Trp
<220> FEATURE:
<221> NAME/KEY: MOD_RES
<222> LOCATION: (5)..(6)
<223> OTHER INFORMATION: Any one of the 20 amino acids except Cys and
      Trp and is biased 50% to His
<220> FEATURE:
<221> NAME/KEY: MOD_RES
<222> LOCATION: (7)..(7)
<223> OTHER INFORMATION: Any one of the 20 amino acids except Cys and
      Trp and is biased 50% to Lys
<220> FEATURE:
<221> NAME/KEY: MOD_RES
<222> LOCATION: (8)..(8)
<223> OTHER INFORMATION: Phosphorylated-Thr
<220> FEATURE:
<221> NAME/KEY: MOD_RES
<222> LOCATION: (10)..(10)
<223> OTHER INFORMATION: Any one of the 20 amino acids except Cys and
      Trp and is biased 50% to Lys
<220> FEATURE:
```

```
<221> NAME/KEY: MOD_RES
<222> LOCATION: (13)..(14)
<223> OTHER INFORMATION: Any one of the 20 amino acids except Cys and
      Trp

<400> SEQUENCE: 100

Cys Xaa Xaa Lys Xaa Xaa Xaa Thr Pro Xaa His Arg Xaa Xaa
1               5                   10

<210> SEQ ID NO 101
<211> LENGTH: 14
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys and
      Trp
<220> FEATURE:
<221> NAME/KEY: MOD_RES
<222> LOCATION: (5)..(7)
<223> OTHER INFORMATION: Any one of the 20 amino acids except Cys and
      Trp and is biased 50% to Glu and Asp
<220> FEATURE:
<221> NAME/KEY: MOD_RES
<222> LOCATION: (8)..(8)
<223> OTHER INFORMATION: Phosphorylated-Tyr
<220> FEATURE:
<221> NAME/KEY: MOD_RES
<222> LOCATION: (10)..(10)
<223> OTHER INFORMATION: Any one of the 20 amino acids except Cys and
      Trp and is biased 50% to Met
<220> FEATURE:
<221> NAME/KEY: MOD_RES
<222> LOCATION: (12)..(12)
<223> OTHER INFORMATION: Any one of the 20 amino acids except Cys and
      Trp and is biased 50% to Phe
<220> FEATURE:
<221> NAME/KEY: MOD_RES
<222> LOCATION: (13)..(14)
<223> OTHER INFORMATION: Any one of the 20 amino acids except Cys and
      Trp

<400> SEQUENCE: 101

Cys Xaa Xaa Xaa Xaa Xaa Xaa Tyr Met Xaa Met Xaa Xaa Xaa
1               5                   10

<210> SEQ ID NO 102
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr
<220> FEATURE:
<221> NAME/KEY: MOD_RES
<222> LOCATION: (3)..(3)
<223> OTHER INFORMATION: Variable amino acid

<400> SEQUENCE: 102

Tyr Met Xaa Met
1

<210> SEQ ID NO 103
<211> LENGTH: 15
<212> TYPE: PRT
<213> ORGANISM: Homo sapiens
<220> FEATURE:
<221> NAME/KEY: MOD_RES
<222> LOCATION: (2)..(7)
<223> OTHER INFORMATION: Any one of the 20 amino acids except Cys and
      Trp
```

```
<220> FEATURE:
<221> NAME/KEY: MOD_RES
<222> LOCATION: (8)..(8)
<223> OTHER INFORMATION: Any one of the 20 amino acids except Cys and
      Trp and is biased 50% to Glu
<220> FEATURE:
<221> NAME/KEY: MOD_RES
<222> LOCATION: (9)..(9)
<223> OTHER INFORMATION: Phosphorylated-Tyr
<220> FEATURE:
<221> NAME/KEY: MOD_RES
<222> LOCATION: (11)..(11)
<223> OTHER INFORMATION: Any one of the 20 amino acids except Cys and
      Trp
<220> FEATURE:
<221> NAME/KEY: MOD_RES
<222> LOCATION: (13)..(15)
<223> OTHER INFORMATION: Any one of the 20 amino acids except Cys and
      Trp

<400> SEQUENCE: 103

Cys Xaa Xaa Xaa Xaa Xaa Xaa Tyr Met Xaa Met Xaa Xaa Xaa
1               5                   10                  15

<210> SEQ ID NO 104
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Phosphorylated-Thr

<400> SEQUENCE: 104

Arg Gln Xaa Thr Phe Asp
1               5

<210> SEQ ID NO 105
<211> LENGTH: 15
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any one of the 20 amino acids except Cys and
      Trp
<220> FEATURE:
<221> NAME/KEY: MOD_RES
<222> LOCATION: (4)..(4)
<223> OTHER INFORMATION: Any one of the 20 amino acids except Cys and
      Trp and is biased 50% to Lys
<220> FEATURE:
<221> NAME/KEY: MOD_RES
<222> LOCATION: (7)..(7)
<223> OTHER INFORMATION: Any one of the 20 amino acids except Cys and
      Trp and is biased 50% to Gln
<220> FEATURE:
<221> NAME/KEY: MOD_RES
<222> LOCATION: (8)..(8)
<223> OTHER INFORMATION: Phosphorylated-Thr
<220> FEATURE:
<221> NAME/KEY: MOD_RES
<222> LOCATION: (11)..(11)
<223> OTHER INFORMATION: Any one of the 20 amino acids except Cys and
      Trp and is biased 50% to Leu
<220> FEATURE:
<221> NAME/KEY: MOD_RES
<222> LOCATION: (12)..(12)
<223> OTHER INFORMATION: Any one of the 20 amino acids except Cys and
      Trp and is biased 50% to Phe
<220> FEATURE:
```

```
<221> NAME/KEY: MOD_RES
<222> LOCATION: (13)..(15)
<223> OTHER INFORMATION: Any one of the 20 amino acids except Cys and
      Trp

<400> SEQUENCE: 105

Cys Xaa Xaa Xaa Arg Gln Xaa Thr Phe Asp Xaa Xaa Xaa Xaa Xaa
1               5                   10                  15

<210> SEQ ID NO 106
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(4)
<223> OTHER INFORMATION: Phosphorylated-Tyr

<400> SEQUENCE: 106

Glu Xaa Ile Tyr Gly Glu Phe
1               5

<210> SEQ ID NO 107
<211> LENGTH: 16
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys and
      Trp
<220> FEATURE:
<221> NAME/KEY: MOD_RES
<222> LOCATION: (5)..(5)
<223> OTHER INFORMATION: Any one of the 20 amino acids except Cys and
      Trp and is biased 50% to Glu
<220> FEATURE:
<221> NAME/KEY: MOD_RES
<222> LOCATION: (7)..(7)
<223> OTHER INFORMATION: Any one of the 20 amino acids except Cys and
      Trp and is biased 50% to Glu
<220> FEATURE:
<221> NAME/KEY: MOD_RES
<222> LOCATION: (9)..(9)
<223> OTHER INFORMATION: Phosphorylated-Tyr
<220> FEATURE:
<221> NAME/KEY: MOD_RES
<222> LOCATION: (13)..(16)
<223> OTHER INFORMATION: Any one of the 20 amino acids except Cys and
      Trp

<400> SEQUENCE: 107

Cys Xaa Xaa Xaa Xaa Glu Xaa Ile Tyr Gly Glu Phe Xaa Xaa Xaa Xaa
1               5                   10                  15

<210> SEQ ID NO 108
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Ser
<220> FEATURE:
<221> NAME/KEY: MOD_RES
<222> LOCATION: (4)..(4)
<223> OTHER INFORMATION: Lys or Arg

<400> SEQUENCE: 108
```

Ser Pro Arg Xaa
1

<210> SEQ ID NO 109
<211> LENGTH: 16
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any one of the 20 amino acids except Cys and
      Trp
<220> FEATURE:
<221> NAME/KEY: MOD_RES
<222> LOCATION: (5)..(7)
<223> OTHER INFORMATION: Any one of the 20 amino acids except Cys and
      Trp and is biased 50% to His
<220> FEATURE:
<221> NAME/KEY: MOD_RES
<222> LOCATION: (8)..(8)
<223> OTHER INFORMATION: Any one of the 20 amino acids except Cys and
      Trp and is biased 50% to Lys or Arg
<220> FEATURE:
<221> NAME/KEY: MOD_RES
<222> LOCATION: (9)..(9)
<223> OTHER INFORMATION: Phosphorylated-Ser
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (13)..(13)
<223> OTHER INFORMATION: Any one of the 20 amino acids except Cys and
      Trp and is biased 50% to Arg
<220> FEATURE:
<221> NAME/KEY: MOD_RES
<222> LOCATION: (14)..(16)
<223> OTHER INFORMATION: Any one of the 20 amino acids except Cys and
      Trp

<400> SEQUENCE: 109

Cys Xaa Xaa Xaa Xaa Xaa Xaa Xaa Ser Pro Arg Xaa Xaa Xaa Xaa Xaa
1               5                   10                  15

<210> SEQ ID NO 110
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Thr
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)..(5)
<223> OTHER INFORMATION: Phosphorylated-Ser

<400> SEQUENCE: 110

Thr Pro Xaa Xaa Ser Pro
1               5

<210> SEQ ID NO 111
<211> LENGTH: 18
<212> TYPE: PRT
<213> ORGANISM: Homo sapiens
<220> FEATURE:
<221> NAME/KEY: MOD_RES
<222> LOCATION: (2)..(2)

```
<223> OTHER INFORMATION: Any one of the 20 amino acids except Cys and
      Trp
<220> FEATURE:
<221> NAME/KEY: MOD_RES
<222> LOCATION: (3)..(3)
<223> OTHER INFORMATION: Any one of the 20 amino acids except Cys and
      Trp and is biased 50% to Pro or Phe
<220> FEATURE:
<221> NAME/KEY: MOD_RES
<222> LOCATION: (4)..(4)
<223> OTHER INFORMATION: Any one of the 20 amino acids except Cys and
      Trp
<220> FEATURE:
<221> NAME/KEY: MOD_RES
<222> LOCATION: (5)..(6)
<223> OTHER INFORMATION: Any one of the 20 amino acids except Cys and
      Trp and is biased 50% to Pro or Leu
<220> FEATURE:
<221> NAME/KEY: MOD_RES
<222> LOCATION: (7)..(7)
<223> OTHER INFORMATION: Any one of the 20 amino acids except Cys and
      Trp and is biased 50% to Pro
<220> FEATURE:
<221> NAME/KEY: MOD_RES
<222> LOCATION: (8)..(8)
<223> OTHER INFORMATION: Phosphorylated-Thr
<220> FEATURE:
<221> NAME/KEY: MOD_RES
<222> LOCATION: (10)..(10)
<223> OTHER INFORMATION: Any one of the 20 amino acids except Cys and
      Trp and is biased 50% to Pro
<220> FEATURE:
<221> NAME/KEY: MOD_RES
<222> LOCATION: (11)..(11)
<223> OTHER INFORMATION: Any one of the 20 amino acids except Cys and
      Trp and is biased 50% to Pro or Leu
<220> FEATURE:
<221> NAME/KEY: MOD_RES
<222> LOCATION: (12)..(12)
<223> OTHER INFORMATION: Phosphorylated-Ser
<220> FEATURE:
<221> NAME/KEY: MOD_RES
<222> LOCATION: (14)..(18)
<223> OTHER INFORMATION: Any one of the 20 amino acids except Cys and
      Trp

<400> SEQUENCE: 111

Cys Xaa Xaa Xaa Xaa Xaa Xaa Thr Pro Xaa Xaa Ser Pro Xaa Xaa Xaa
1               5                   10                  15

Xaa Xaa

<210> SEQ ID NO 112
<211> LENGTH: 15
<212> TYPE: PRT
<213> ORGANISM: Homo sapiens
<220> FEATURE:
<221> NAME/KEY: MOD_RES
<222> LOCATION: (2)..(6)
<223> OTHER INFORMATION: Any one of the 20 amino acids except Cys and
      Trp
<220> FEATURE:
<221> NAME/KEY: MOD_RES
<222> LOCATION: (8)..(8)
<223> OTHER INFORMATION: Phosphorylated-Ser
<220> FEATURE:
<221> NAME/KEY: MOD_RES
<222> LOCATION: (10)..(15)
<223> OTHER INFORMATION: Any one of the 20 amino acids except Cys and
      Trp

<400> SEQUENCE: 112

Cys Xaa Xaa Xaa Xaa Xaa Pro Ser Pro Xaa Xaa Xaa Xaa Xaa Xaa
1               5                   10                  15
```

-continued

```
<210> SEQ ID NO 113
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 113

Lys Arg Arg Arg Ser Ser Lys Asp
1               5

<210> SEQ ID NO 114
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 114

Lys Arg Lys Arg Ser Arg Lys Glu
1               5

<210> SEQ ID NO 115
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 115

Ser Arg Arg Pro Ser Tyr Arg Lys
1               5

<210> SEQ ID NO 116
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 116

Gly Trp Lys Asn Ser Ile Arg His
1               5

<210> SEQ ID NO 117
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 117

Gly Leu Thr Val Lys
1               5

<210> SEQ ID NO 118
<211> LENGTH: 5
<212> TYPE: PRT
<213> ORGANISM: Homo sapiens
```

```
<220> FEATURE:
<221> NAME/KEY: MOD_RES
<222> LOCATION: (3)..(3)
<223> OTHER INFORMATION: Phosphorylated-Thr

<400> SEQUENCE: 118

Leu Ala Thr Val Lys
1               5

<210> SEQ ID NO 119
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 119

Phe Phe Thr Arg His
1               5

<210> SEQ ID NO 120
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 120

Pro Leu Thr Pro Arg
1               5

<210> SEQ ID NO 121
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 121

Asn Val Thr Met Arg
1               5

<210> SEQ ID NO 122
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 122

Ala Val Thr Pro Lys
1               5

<210> SEQ ID NO 123
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser
```

```
<400> SEQUENCE: 123

Pro Leu Ser Gln Glu
1               5

<210> SEQ ID NO 124
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 124

Tyr Pro Ser Gln Glu
1               5

<210> SEQ ID NO 125
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr

<400> SEQUENCE: 125

Val Ser Thr Gln Glu
1               5

<210> SEQ ID NO 126
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Thr
<220> FEATURE:
<221> NAME/KEY: MOD_RES
<222> LOCATION: (5)..(5)
<223> OTHER INFORMATION: Phosphorylated-Ser

<400> SEQUENCE: 126

Ser Val Thr Gln Ser Gln Gly
1               5

<210> SEQ ID NO 127
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 127

Pro Ile Ser Gln Asn
1               5

<210> SEQ ID NO 128
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser
```

```
<400> SEQUENCE: 128

Ser Phe Ser Gln Pro
1               5

<210> SEQ ID NO 129
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 129

Ser Ser Ser Gln Pro
1               5

<210> SEQ ID NO 130
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 130

Asp Leu Ser Gln Val
1               5

<210> SEQ ID NO 131
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 131

Ser Leu Ser Gln Gly
1               5

<210> SEQ ID NO 132
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 132

Tyr Arg Ser Pro Ser Met Pro
1               5

<210> SEQ ID NO 133
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 133

Gly Arg Ser Arg Ser Ala Pro
```

```
<210> SEQ ID NO 134
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 134

Pro Arg Thr Thr Ser Phe Ala
1               5

<210> SEQ ID NO 135
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 135

Ser Arg His Ser Thr Tyr Pro
1               5

<210> SEQ ID NO 136
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 136

Gln Arg Ser Thr Ser Thr Pro
1               5

<210> SEQ ID NO 137
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 137

Leu Arg Ser Ile Ser Leu Pro
1               5

<210> SEQ ID NO 138
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 138

Phe Leu Gly Phe Ser Tyr
1               5

<210> SEQ ID NO 139
```

```
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 139

Phe Ser Asn Phe Ser Phe
1               5

<210> SEQ ID NO 140
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 140

Phe Arg Asn Phe Ser Tyr
1               5

<210> SEQ ID NO 141
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 141

Phe Gln Gly Phe Thr Tyr
1               5

<210> SEQ ID NO 142
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 142

Phe Ala Gly Phe Ser Tyr
1               5

<210> SEQ ID NO 143
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 143

Phe Leu Gly Phe Thr Tyr
1               5

<210> SEQ ID NO 144
<211> LENGTH: 6
<212> TYPE: PRT
<213> ORGANISM: Homo sapiens
<220> FEATURE:
```

```
<221> NAME/KEY: MOD_RES
<222> LOCATION: (5)..(5)
<223> OTHER INFORMATION: Phosphorylated-Thr

<400> SEQUENCE: 144

Phe Ser His Phe Thr Phe
1               5

<210> SEQ ID NO 145
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 145

Phe Pro Gln Phe Ser Tyr
1               5

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Arg Ser Ser
1

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Ser, Thr or Ala
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(7)
<223> OTHER INFORMATION: Phe or Leu

<400> SEQUENCE: 147

Arg Xaa Arg Xaa Xaa Xaa Xaa
1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr

<400> SEQUENCE: 148

Arg Xaa Arg Xaa Xaa Xaa
1               5

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile or Met
<220> FEATURE:
<221> NAME/KEY: MOD_RES
<222> LOCATION: (2)..(2)
<223> OTHER INFORMATION: Arg, Lys or His
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (10)..(10)
<223> OTHER INFORMATION: Val, Leu, Ile or Met

<400> SEQUENCE: 149

Xaa Xaa Xaa Xaa Xaa Xaa Xaa Xaa Xaa Xaa
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile or Met
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Arg, Lys or His
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES

```
<222> LOCATION: (6)..(6)
<223> OTHER INFORMATION: Ser or Thr
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (10)..(10)
<223> OTHER INFORMATION: Val, Leu, Ile or Met

<400> SEQUENCE: 150

Xaa Xaa Xaa Xaa Xaa Xaa Xaa Xaa Xaa Xaa
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile or Met
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Arg, Lys or His
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (10)..(10)
<223> OTHER INFORMATION: Val, Leu, Ile or Met

<400> SEQUENCE: 151

Xaa Xaa Xaa Xaa Xaa Xaa Xaa Xaa Xaa Xaa
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile, Met or Phe
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Arg, Lys or His
<220> FEATURE:
```

```
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (10)..(10)
<223> OTHER INFORMATION: Val, Leu, Ile, Met or Phe

<400> SEQUENCE: 152

Xaa Xaa Xaa Xaa Xaa Xaa Xaa Xaa Xaa Xaa
1               5                   10

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro, Leu, Ile or Met
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Leu, Ile, Asp or Glu

<400> SEQUENCE: 153

Xaa Xaa Xaa Ser Gln
1               5

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Leu Ser Gln Glu
1

<210> SEQ ID NO 155
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr

<400> SEQUENCE: 155

Xaa Gln
1
```

```
<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile, Met or Phe
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (10)..(10)
<223> OTHER INFORMATION: Val, Leu, Ile, Met or Phe

<400> SEQUENCE: 156

Xaa Xaa Arg Xaa Xaa Xaa Xaa Xaa Xaa Xaa
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Phe
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (3)..(3)
<223> OTHER INFORMATION: Gln or Met
<220> FEATURE:
<221> NAME/KEY: MOD_RES
<222> LOCATION: (4)..(4)
<223> OTHER INFORMATION: Gln, Met, Lys, Leu or Phe
<220> FEATURE:
<221> NAME/KEY: MOD_RES
<222> LOCATION: (6)..(6)
<223> OTHER INFORMATION: Val, Leu, Ile, Met or Phe
<220> FEATURE:
<221> NAME/KEY: MOD_RES
<222> LOCATION: (7)..(7)
<223> OTHER INFORMATION: Asp, Glu or Ile
<220> FEATURE:
<221> NAME/KEY: MOD_RES
<222> LOCATION: (8)..(8)
<223> OTHER INFORMATION: Leu, Met, Lys or Ile
<220> FEATURE:
<221> NAME/KEY: MOD_RES
<222> LOCATION: (9)..(9)
<223> OTHER INFORMATION: Phe or Lys
```

```
<400> SEQUENCE: 157

Xaa Xaa Xaa Xaa Ser Xaa Xaa Xaa Xaa
1               5

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr

<400> SEQUENCE: 158

Arg Xaa Xaa Xaa
1

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid

<400> SEQUENCE: 159

Arg Xaa Xaa Ser Val
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile, Phe or Tyr
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(7)
<223> OTHER INFORMATION: Val, Leu, Ile, Phe or Tyr

<400> SEQUENCE: 160

Xaa Xaa Arg Xaa Xaa Xaa Xaa
1               5
```

```
<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile, Phe or Tyr
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(4)
<223> OTHER INFORMATION: Ala, Asn, Asp, Cys, Gln, Glu, Ile, Leu, Met,
      Phe, Pro, Ser, Thr, Trp or Val
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr

<400> SEQUENCE: 161

Xaa Xaa Arg Xaa Xaa Xaa
1               5

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (4)..(5)
<223> OTHER INFORMATION: Arg or Lys

<400> SEQUENCE: 162

Xaa Ser Pro Xaa Xaa
1               5

<210> SEQ ID NO 163
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Arg or Lys

<400> SEQUENCE: 163
```

```
Xaa Pro Xaa Xaa
1

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (7)..(7)
<223> OTHER INFORMATION: Pro, Lys or Met
<220> FEATURE:
<221> NAME/KEY: MOD_RES
<222> LOCATION: (8)..(8)
<223> OTHER INFORMATION: Arg or Lys

<400> SEQUENCE: 164

Arg Xaa Pro Met Ser Pro Xaa Xaa Lys
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (7)..(7)
<223> OTHER INFORMATION: Arg, Lys or His

<400> SEQUENCE: 165

Pro Leu Xaa Pro Ile Pro Xaa
1               5

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Arg, Lys or His

<400> SEQUENCE: 166

Pro Leu Xaa Pro Xaa Xaa
1               5
```

```
<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, His or Gly
<220> FEATURE:
<221> NAME/KEY: MOD_RES
<222> LOCATION: (3)..(3)
<223> OTHER INFORMATION: His or Pro
<220> FEATURE:
<221> NAME/KEY: MOD_RES
<222> LOCATION: (4)..(4)
<223> OTHER INFORMATION: Lys, Gly or His
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (8)..(9)
<223> OTHER INFORMATION: Arg, Lys or His

<400> SEQUENCE: 167

Xaa His Xaa Xaa Ser Pro Xaa Xaa Xaa
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Ser or Thr

<400> SEQUENCE: 168

Xaa Pro Gly Xaa Pro Gly Thr Pro
1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile or Met
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(5)
<223> OTHER INFORMATION: Variable amino acid
```

```
<220> FEATURE:
<221> NAME/KEY: MOD_RES
<222> LOCATION: (6)..(6)
<223> OTHER INFORMATION: Ser or Thr

<400> SEQUENCE: 169

Xaa Xaa Xaa Xaa Xaa Xaa
1               5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr

<400> SEQUENCE: 170

Xaa Xaa Xaa Xaa Xaa
1               5

<210> SEQ ID NO 171
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr

<400> SEQUENCE: 171

Xaa Xaa Xaa Xaa
1

<210> SEQ ID NO 172
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
```

```
<221> NAME/KEY: MOD_RES
<222> LOCATION: (2)..(3)
<223> OTHER INFORMATION: Variable amino acid

<400> SEQUENCE: 172

Xaa Xaa Xaa Ser
1

<210> SEQ ID NO 173
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr

<400> SEQUENCE: 173

Ser Pro Xaa Xaa Xaa
1               5

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Glu
<220> FEATURE:
<221> NAME/KEY: MOD_RES
<222> LOCATION: (3)..(3)
<223> OTHER INFORMATION: Asp or Tyr
<220> FEATURE:
<221> NAME/KEY: MOD_RES
<222> LOCATION: (4)..(4)
<223> OTHER INFORMATION: Ala or Asp
<220> FEATURE:
<221> NAME/KEY: MOD_RES
<222> LOCATION: (5)..(5)
<223> OTHER INFORMATION: Ala or Gly
<220> FEATURE:
<221> NAME/KEY: MOD_RES
<222> LOCATION: (8)..(8)
<223> OTHER INFORMATION: Ile, Tyr, Phe or Gly
<220> FEATURE:
<221> NAME/KEY: MOD_RES
<222> LOCATION: (9)..(9)
<223> OTHER INFORMATION: Ile, Gly or Phe
<220> FEATURE:
<221> NAME/KEY: MOD_RES
<222> LOCATION: (10)..(10)
<223> OTHER INFORMATION: Phe or Gly
<220> FEATURE:
<221> NAME/KEY: MOD_RES
<222> LOCATION: (11)..(11)
<223> OTHER INFORMATION: Phe, Pro or Leu

<400> SEQUENCE: 174

Tyr Xaa Xaa Xaa Xaa Ser Ile Xaa Xaa Xaa Xaa
1               5                   10

<210> SEQ ID NO 175
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Asp or Ala
<220> FEATURE:
<221> NAME/KEY: MOD_RES
<222> LOCATION: (2)..(4)
<223> OTHER INFORMATION: Glu or Asp
<220> FEATURE:
<221> NAME/KEY: MOD_RES
<222> LOCATION: (6)..(7)
<223> OTHER INFORMATION: Glu, Asp or Ala
<220> FEATURE:
<221> NAME/KEY: MOD_RES
<222> LOCATION: (8)..(9)
<223> OTHER INFORMATION: Glu or Asp

<400> SEQUENCE: 175

Xaa Xaa Xaa Xaa Ser Xaa Xaa Xaa Xaa
1               5

<210> SEQ ID NO 176
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Glu or Asp

<400> SEQUENCE: 176

Xaa Xaa Xaa Xaa
1

<210> SEQ ID NO 177
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Glu, Asp or Ser

<400> SEQUENCE: 177

Xaa Xaa Xaa Xaa
1
```

```
<210> SEQ ID NO 178
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser, Thr or Tyr

<400> SEQUENCE: 178

Xaa Xaa Xaa Xaa
1

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Glu, Ser or Thr

<400> SEQUENCE: 179

Ser Xaa Xaa Xaa
1

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
```

```
<222> LOCATION: (6)..(6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 180

Xaa Xaa Xaa Xaa Xaa Xaa Ser Xaa Xaa Arg
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(6)
<223> OTHER INFORMATION: Variable amino acid

<400> SEQUENCE: 181

Arg Xaa Xaa Xaa Xaa Xaa Arg
1               5

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid

<400> SEQUENCE: 182

Arg Lys Xaa Arg Ser
1               5

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Variable amino acid

<400> SEQUENCE: 183

Arg Arg Lys Xaa Thr
1               5

<210> SEQ ID NO 184
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid

<400> SEQUENCE: 184

Arg Arg Xaa Xaa Ser
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Leu, Ile, Met or Phe
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(7)
<223> OTHER INFORMATION: Ile, Leu, Met, Val or Glu

<400> SEQUENCE: 185

Xaa Arg Arg Xaa Xaa Xaa Xaa
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Val or Leu

<400> SEQUENCE: 186

Arg Xaa Xaa Xaa Xaa Arg
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(7)
<223> OTHER INFORMATION: Val, Leu or Ile
<220> FEATURE:
<221> NAME/KEY: MOD_RES
<222> LOCATION: (8)..(8)
<223> OTHER INFORMATION: Variable amino acid

<400> SEQUENCE: 187

Xaa Xaa Arg Arg Xaa Xaa Xaa Xaa
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (7)..(7)
<223> OTHER INFORMATION: Val, Leu or Ile
<220> FEATURE:
<221> NAME/KEY: MOD_RES
<222> LOCATION: (8)..(8)
<223> OTHER INFORMATION: Variable amino acid

<400> SEQUENCE: 188

Lys Lys Xaa Arg Arg Thr Xaa Xaa
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (7)..(7)
<223> OTHER INFORMATION: Val, Leu or Ile
<220> FEATURE:
<221> NAME/KEY: MOD_RES
<222> LOCATION: (8)..(8)
<223> OTHER INFORMATION: Variable amino acid

<400> SEQUENCE: 189

Arg Lys Lys Xaa Arg Thr Xaa Xaa
1               5
```

```
<210> SEQ ID NO 190
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Thr Pro Tyr
1

<210> SEQ ID NO 191
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Glu Tyr
1

<210> SEQ ID NO 192
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid

<400> SEQUENCE: 192

Thr Xaa Tyr
1

<210> SEQ ID NO 193
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Thr Gly Tyr
1

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid

<400> SEQUENCE: 194

Arg Pro Xaa Ser Thr Pro
1               5
```

```
<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr, Pro or Ser
<220> FEATURE:
<221> NAME/KEY: MOD_RES
<222> LOCATION: (2)..(2)
<223> OTHER INFORMATION: Gly, Pro, Glu or Tyr
<220> FEATURE:
<221> NAME/KEY: MOD_RES
<222> LOCATION: (3)..(3)
<223> OTHER INFORMATION: Pro, Leu or Ile
<220> FEATURE:
<221> NAME/KEY: MOD_RES
<222> LOCATION: (4)..(4)
<223> OTHER INFORMATION: Leu, Met or Pro
<220> FEATURE:
<221> NAME/KEY: MOD_RES
<222> LOCATION: (7)..(7)
<223> OTHER INFORMATION: Gly, Pro or Phe
<220> FEATURE:
<221> NAME/KEY: MOD_RES
<222> LOCATION: (8)..(8)
<223> OTHER INFORMATION: Pro, Phe, Gly or Tyr
<220> FEATURE:
<221> NAME/KEY: MOD_RES
<222> LOCATION: (9)..(9)
<223> OTHER INFORMATION: Phe, Tyr or Ile

<400> SEQUENCE: 195

Xaa Xaa Xaa Xaa Ser Pro Xaa Xaa Xaa
1               5

<210> SEQ ID NO 196
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr

<400> SEQUENCE: 196

Pro Xaa Xaa Pro
1

<210> SEQ ID NO 197
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Lys Ser Pro Pro
1
```

-continued

```
<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr

<400> SEQUENCE: 198

Ser Xaa Xaa Xaa Xaa
1               5

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid

<400> SEQUENCE: 199

Ser Xaa Xaa Xaa Ser Pro
1               5

<210> SEQ ID NO 200
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Ser or Thr

<400> SEQUENCE: 200

Xaa Xaa Pro
1

<210> SEQ ID NO 201
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Arg or Lys

<400> SEQUENCE: 201
```

```
Xaa Pro Xaa
1

<210> SEQ ID NO 202
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Leu Thr Pro
1

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Pro Leu Thr Leu Pro
1               5

<210> SEQ ID NO 204
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Thr Leu Pro
1

<210> SEQ ID NO 205
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Thr Leu Pro
1

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid

<400> SEQUENCE: 206

Leu Xaa Thr
1
```

```
<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Phe, Val, Leu or Ala
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid

<400> SEQUENCE: 207

Xaa Xaa Xaa Xaa Arg Xaa Xaa Ser Xaa Xaa
1               5                   10

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr

<400> SEQUENCE: 208

Ser Xaa Xaa Xaa Xaa
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Asn
<220> FEATURE:
<221> NAME/KEY: MOD_RES
<222> LOCATION: (2)..(2)
<223> OTHER INFORMATION: Phe, Leu or Met
<220> FEATURE:
<221> NAME/KEY: MOD_RES
<222> LOCATION: (3)..(4)
<223> OTHER INFORMATION: Arg or Lys
<220> FEATURE:
<221> NAME/KEY: MOD_RES
<222> LOCATION: (6)..(7)
<223> OTHER INFORMATION: Arg, Val, Ile or Met
```

```
<220> FEATURE:
<221> NAME/KEY: MOD_RES
<222> LOCATION: (8)..(8)
<223> OTHER INFORMATION: Val, Ile, Met or Phe
<220> FEATURE:
<221> NAME/KEY: MOD_RES
<222> LOCATION: (9)..(9)
<223> OTHER INFORMATION: Ile, Met or Phe

<400> SEQUENCE: 209

Xaa Xaa Xaa Xaa Ser Xaa Xaa Xaa Xaa
1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gln or Met

<400> SEQUENCE: 210

Gly Pro Xaa Ser Pro Ile
1               5

<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (3)..(3)
<223> OTHER INFORMATION: Variable amino acid

<400> SEQUENCE: 211

Xaa Arg Xaa Ser
1

<210> SEQ ID NO 212
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr

<400> SEQUENCE: 212

Xaa Xaa Xaa Xaa
1
```

```
<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe or Tyr

<400> SEQUENCE: 213

Phe Xaa Xaa Phe Xaa Xaa
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Met or Lys
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (3)..(3)
<223> OTHER INFORMATION: Met, Arg, Gln or Phe
<220> FEATURE:
<221> NAME/KEY: MOD_RES
<222> LOCATION: (4)..(4)
<223> OTHER INFORMATION: Met, Phe, Leu or Ile
<220> FEATURE:
<221> NAME/KEY: MOD_RES
<222> LOCATION: (6)..(6)
<223> OTHER INFORMATION: Leu, Ile, Met or Phe
<220> FEATURE:
<221> NAME/KEY: MOD_RES
<222> LOCATION: (7)..(7)
<223> OTHER INFORMATION: Phe, Arg or Lys
<220> FEATURE:
<221> NAME/KEY: MOD_RES
<222> LOCATION: (8)..(8)
<223> OTHER INFORMATION: Leu or Ile
<220> FEATURE:
<221> NAME/KEY: MOD_RES
<222> LOCATION: (9)..(9)
<223> OTHER INFORMATION: Phe, Leu or Ile

<400> SEQUENCE: 214

Xaa Xaa Xaa Xaa Ser Xaa Xaa Xaa Xaa
1               5

<210> SEQ ID NO 215
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Val or Ile

<400> SEQUENCE: 215

Xaa Xaa Xaa Ser Xaa
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Lys Lys Gln Ile Ser Val Arg
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Arg or Lys
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr

<400> SEQUENCE: 217

Xaa Xaa Xaa Xaa Xaa
1               5

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Arg or Lys
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
```

<223> OTHER INFORMATION: Ser or Thr

<400> SEQUENCE: 218

Xaa Xaa Xaa Xaa
1

<210> SEQ ID NO 219
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr

<400> SEQUENCE: 219

Lys Xaa Xaa Xaa
1

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr

<400> SEQUENCE: 220

Lys Xaa Xaa Xaa Xaa
1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Val, Leu, Ile, Phe or Tyr
<220> FEATURE:
<221> NAME/KEY: MOD_RES
<222> LOCATION: (6)..(7)
<223> OTHER INFORMATION: Variable amino acid

```
<400> SEQUENCE: 221

Arg Xaa Xaa Xaa Xaa Xaa Xaa Asp
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid

<400> SEQUENCE: 222

Arg Lys Xaa Xaa Ser
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg or Asn
<220> FEATURE:
<221> NAME/KEY: MOD_RES
<222> LOCATION: (8)..(8)
<223> OTHER INFORMATION: Phe or Asp

<400> SEQUENCE: 223

Arg Arg Arg Xaa Ser Ile Ile Xaa
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Arg Arg Arg Arg Ser Ile Ile Phe Ile
1               5

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
```

```
<223> OTHER INFORMATION: Val, Leu, Ile, Phe or Tyr

<400> SEQUENCE: 225

Arg Arg Xaa Xaa Xaa
1               5

<210> SEQ ID NO 226
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid

<400> SEQUENCE: 226

Arg Xaa Ser
1

<210> SEQ ID NO 227
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr

<400> SEQUENCE: 227

Xaa Xaa Xaa
1

<210> SEQ ID NO 228
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid

<400> SEQUENCE: 228

Arg Xaa Xaa Ser
1

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(2)
<223> OTHER INFORMATION: Arg or Lys
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Arg or Lys

<400> SEQUENCE: 229

Xaa Xaa Xaa Xaa Xaa Xaa
1               5

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (5)..(5)
<223> OTHER INFORMATION: Arg or Lys

<400> SEQUENCE: 230

Xaa Xaa Xaa Xaa Xaa
1               5

<210> SEQ ID NO 231
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
```

```
<400> SEQUENCE: 231

Xaa Xaa Xaa Xaa
1

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Arg or Lys

<400> SEQUENCE: 232

Xaa Xaa Xaa Xaa Xaa Xaa
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Arg Lys Gly Ser Leu Arg Gln
1               5

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Phe
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (9)..(10)
<223> OTHER INFORMATION: Arg or Lys

<400> SEQUENCE: 234

Arg Xaa Arg Arg Xaa Gly Ser Phe Xaa Xaa
1               5                   10
```

```
<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Arg or Phe
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (4)..(4)
<223> OTHER INFORMATION: Lys or Gln
<220> FEATURE:
<221> NAME/KEY: MOD_RES
<222> LOCATION: (7)..(7)
<223> OTHER INFORMATION: Phe or Met
<220> FEATURE:
<221> NAME/KEY: MOD_RES
<222> LOCATION: (10)..(10)
<223> OTHER INFORMATION: Variable amino acid

<400> SEQUENCE: 235

Xaa Xaa Arg Xaa Gly Ser Xaa Lys Lys Xaa Ala
1               5                   10

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid

<400> SEQUENCE: 236

Arg Xaa Arg Lys Gly Ser Phe
1               5

<210> SEQ ID NO 237
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Glu or Arg
<220> FEATURE:
<221> NAME/KEY: MOD_RES
<222> LOCATION: (3)..(3)
<223> OTHER INFORMATION: Variable amino acid

<400> SEQUENCE: 237

Arg Xaa Xaa Ser
1

<210> SEQ ID NO 238
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 238

Arg Lys Gln Gly Ser Val Arg Arg
1               5

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)..(6)
<223> OTHER INFORMATION: Arg or Lys

<400> SEQUENCE: 239

Ala Arg Xaa Xaa Arg Xaa Arg Ser Phe Arg Arg
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Lys
<220> FEATURE:
<221> NAME/KEY: MOD_RES
<222> LOCATION: (8)..(9)
<223> OTHER INFORMATION: Arg or Lys

<400> SEQUENCE: 240

Arg Arg Arg Lys Xaa Ser Phe Xaa Xaa Lys Ala
1               5                   10

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (2)..(2)
<223> OTHER INFORMATION: Val, Leu or Ala
<220> FEATURE:
<221> NAME/KEY: MOD_RES
<222> LOCATION: (4)..(4)
<223> OTHER INFORMATION: Gln, Lys or Glu

<400> SEQUENCE: 241

Xaa Xaa Arg Xaa Met Ser
1               5
```

```
<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(8)
<223> OTHER INFORMATION: Phe or Met

<400> SEQUENCE: 242

Phe Xaa Arg Xaa Xaa Ser Xaa Xaa
1               5

<210> SEQ ID NO 243
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Arg or Lys

<400> SEQUENCE: 243

Xaa Xaa Xaa
1

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Arg or Lys

<400> SEQUENCE: 244
```

```
Xaa Xaa Xaa Xaa Xaa
1               5

<210> SEQ ID NO 245
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr

<400> SEQUENCE: 245

Xaa Pro
1

<210> SEQ ID NO 246
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (4)..(4)
<223> OTHER INFORMATION: Variable amino acid

<400> SEQUENCE: 246

Lys Xaa Pro Xaa Lys
1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Variable amino acid

<400> SEQUENCE: 247

Lys Ser Pro Xaa Xaa Lys
1               5

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Variable amino acid

<400> SEQUENCE: 248

Lys Ser Pro Xaa Xaa Xaa Lys
1               5
```

```
<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(7)
<223> OTHER INFORMATION: Variable amino acid

<400> SEQUENCE: 249

Lys Ser Pro Xaa Xaa Xaa Xaa Lys
1               5

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Lys Thr Pro Ala Lys Glu Glu
1               5

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid

<400> SEQUENCE: 251

Arg Xaa Xaa Ser Pro Val
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Val, Leu, Ile, Phe or Tyr
<220> FEATURE:
<221> NAME/KEY: MOD_RES
<222> LOCATION: (9)..(9)
<223> OTHER INFORMATION: Val, Leu, Ile, Phe or Tyr

<400> SEQUENCE: 252

Arg Arg Phe Gly Ser Xaa Arg Arg Xaa
1               5

<210> SEQ ID NO 253
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (3)..(3)
<223> OTHER INFORMATION: Variable amino acid

<400> SEQUENCE: 253

Ser Ser Xaa Ser
1

<210> SEQ ID NO 254
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val, Leu, Ile, Met or Phe
<220> FEATURE:
<221> NAME/KEY: MOD_RES
<222> LOCATION: (3)..(3)
<223> OTHER INFORMATION: Glu, Asp, Val or Ile
<220> FEATURE:
<221> NAME/KEY: MOD_RES
<222> LOCATION: (4)..(4)
<223> OTHER INFORMATION: Tyr or Phe

<400> SEQUENCE: 254

Ser Xaa Xaa Xaa
1

<210> SEQ ID NO 255
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (2)..(2)
<223> OTHER INFORMATION: Ile, Leu or Pro

<400> SEQUENCE: 255

Xaa Xaa Thr Pro
1

<210> SEQ ID NO 256
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Tyr, Ile, Val, Pro, Ala, Lys, His, Ser or
      Thr
<220> FEATURE:
<221> NAME/KEY: MOD_RES
<222> LOCATION: (3)..(3)
<223> OTHER INFORMATION: Val or Thr
<220> FEATURE:
<221> NAME/KEY: MOD_RES
<222> LOCATION: (5)..(5)
```

```
<223> OTHER INFORMATION: Gly, Ser, Thr, Asn, Tyr, Arg, Lys or His

<400> SEQUENCE: 256

Ser Xaa Xaa Phe Xaa
1               5

<210> SEQ ID NO 257
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Val, Leu or Ile

<400> SEQUENCE: 257

Thr Xaa Xaa Xaa
1

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Arg Pro Val Ser Ser Ala Ala Ser Val Tyr
1               5                   10

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 259

Arg Xaa Arg Xaa Xaa Ser Xaa Pro
1               5

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid

<400> SEQUENCE: 260

Arg Ser Xaa Xaa Xaa Pro
1               5

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid

<400> SEQUENCE: 261

Arg Xaa Xaa Xaa Ser Xaa Pro
1               5

<210> SEQ ID NO 262
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Lys Cys Ser Thr Trp Pro
1               5

<210> SEQ ID NO 263
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid

<400> SEQUENCE: 263

Arg Xaa Xaa Ser
1
```

```
<210> SEQ ID NO 264
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Tyr Thr Val
1

<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Glu or Asp

<400> SEQUENCE: 265

Ser Xaa Xaa Glu
1

<210> SEQ ID NO 266
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr

<400> SEQUENCE: 266

Xaa Pro
1

<210> SEQ ID NO 267
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Tyr Ile Ile
1

<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Variable amino acid

<400> SEQUENCE: 268

Asp Ser Gly Xaa Xaa Ser
```

```
<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Phe
<220> FEATURE:
<221> NAME/KEY: MOD_RES
<222> LOCATION: (2)..(2)
<223> OTHER INFORMATION: Val, Leu, Ile, Phe, Tyr or Pro
<220> FEATURE:
<221> NAME/KEY: MOD_RES
<222> LOCATION: (3)..(3)
<223> OTHER INFORMATION: Val, Leu, Ile, Phe, Tyr, Ala or Gln
<220> FEATURE:
<221> NAME/KEY: MOD_RES
<222> LOCATION: (4)..(4)
<223> OTHER INFORMATION: Thr, Gln, His or Met
<220> FEATURE:
<221> NAME/KEY: MOD_RES
<222> LOCATION: (6)..(6)
<223> OTHER INFORMATION: Ser or Thr

<400> SEQUENCE: 269

Xaa Xaa Xaa Xaa Ser Xaa
1               5

<210> SEQ ID NO 270
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr

<400> SEQUENCE: 270

Ser Xaa Pro
1

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Arg Arg Val Ser Phe
1               5

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272
```

Lys Ser Val Thr Trp
1               5

<210> SEQ ID NO 273
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)..(4)
<223> OTHER INFORMATION: Asp, Ile, Ser or Tyr

<400> SEQUENCE: 273

Thr Xaa Xaa Xaa
1

<210> SEQ ID NO 274
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid

<400> SEQUENCE: 274

Thr Xaa Pro Tyr
1

<210> SEQ ID NO 275
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Thr Glu Tyr
1

<210> SEQ ID NO 276
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid

<400> SEQUENCE: 276

Thr Xaa Pro Tyr
1

<210> SEQ ID NO 277
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid

<400> SEQUENCE: 277

Pro Xaa Ile Xaa Ile Thr
1               5

<210> SEQ ID NO 278
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid

<400> SEQUENCE: 278

Xaa Xaa Xaa Pro Xaa
1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(7)
<223> OTHER INFORMATION: Variable amino acid

<400> SEQUENCE: 279

Xaa Xaa Xaa Xaa Xaa Xaa Xaa
1               5
```

```
<210> SEQ ID NO 280
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(6)
<223> OTHER INFORMATION: Variable amino acid

<400> SEQUENCE: 280

Xaa Xaa Xaa Xaa Xaa Xaa
1               5

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(6)
<223> OTHER INFORMATION: Variable amino acid
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Variable amino acid

<400> SEQUENCE: 281

Xaa Xaa Xaa Xaa Xaa Xaa Xaa Xaa
1               5

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
```

<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (7)..(7)
<223> OTHER INFORMATION: Variable amino acid

<400> SEQUENCE: 282

Xaa Xaa Xaa Xaa Xaa Xaa Xaa
1               5

<210> SEQ ID NO 283
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (6)..(6)
<223> OTHER INFORMATION: Variable amino acid

<400> SEQUENCE: 283

Xaa Xaa Xaa Xaa Xaa Xaa
1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)..(5)

<223> OTHER INFORMATION: Ser or Thr
<220> FEATURE:
<221> NAME/KEY: MOD_RES
<222> LOCATION: (6)..(7)
<223> OTHER INFORMATION: Variable amino acid

<400> SEQUENCE: 284

Xaa Xaa Xaa Xaa Xaa Xaa Xaa
1               5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(6)
<223> OTHER INFORMATION: Variable amino acid
<220> FEATURE:
<221> NAME/KEY: MOD_RES
<222> LOCATION: (7)..(7)
<223> OTHER INFORMATION: Glu or Asp
<220> FEATURE:
<221> NAME/KEY: MOD_RES
<222> LOCATION: (8)..(8)
<223> OTHER INFORMATION: Variable amino acid

<400> SEQUENCE: 285

Xaa Xaa Xaa Xaa Xaa Xaa Xaa Xaa
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(7)
<223> OTHER INFORMATION: Variable amino acid
<220> FEATURE:
<221> NAME/KEY: MOD_RES
<222> LOCATION: (9)..(9)
<223> OTHER INFORMATION: Variable amino acid

<400> SEQUENCE: 286

Xaa Xaa Xaa Xaa Xaa Xaa Xaa Pro Xaa
1               5

<210> SEQ ID NO 287
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(5)
<223> OTHER INFORMATION: Variable amino acid

<400> SEQUENCE: 287

Arg Xaa Xaa Xaa Xaa
1               5

<210> SEQ ID NO 288
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
<223> OTHER INFORMATION: Variable amino acid

<400> SEQUENCE: 288

Xaa Xaa Xaa Xaa Xaa
1               5

<210> SEQ ID NO 289
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(5)
<223> OTHER INFORMATION: Variable amino acid

<400> SEQUENCE: 289

Xaa Asp Xaa Xaa Xaa
1               5
```

```
<210> SEQ ID NO 290
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid

<400> SEQUENCE: 290

Xaa Xaa Xaa Asp Xaa
1               5

<210> SEQ ID NO 291
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Variable amino acid

<400> SEQUENCE: 291

Xaa Xaa Xaa Gln Xaa
1               5

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Val, Leu or Ile
<220> FEATURE:
<221> NAME/KEY: MOD_RES
<222> LOCATION: (4)..(5)
<223> OTHER INFORMATION: Variable amino acid

<400> SEQUENCE: 292

Xaa Xaa Tyr Xaa Xaa
1               5

<210> SEQ ID NO 293
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid

<400> SEQUENCE: 293

Xaa Xaa Xaa Xaa Tyr Xaa Xaa
1               5

<210> SEQ ID NO 294
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (6)..(6)
<223> OTHER INFORMATION: Variable amino acid

<400> SEQUENCE: 294

Xaa Tyr Xaa Xaa Xaa Xaa
1               5

<210> SEQ ID NO 295
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (3)..(3)
<223> OTHER INFORMATION: Variable amino acid
<220> FEATURE:
```

```
<221> NAME/KEY: MOD_RES
<222> LOCATION: (5)..(6)
<223> OTHER INFORMATION: Variable amino acid

<400> SEQUENCE: 295

Xaa Xaa Xaa Tyr Xaa Xaa
1               5

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (6)..(6)
<223> OTHER INFORMATION: Ile or Met
<220> FEATURE:
<221> NAME/KEY: MOD_RES
<222> LOCATION: (7)..(7)
<223> OTHER INFORMATION: Variable amino acid

<400> SEQUENCE: 296

Xaa Xaa Tyr Xaa Xaa Xaa Xaa
1               5

<210> SEQ ID NO 297
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid

<400> SEQUENCE: 297

Xaa Xaa Tyr Xaa Asn Xaa
1               5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
```

<222> LOCATION: (3)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid

<400> SEQUENCE: 298

Xaa Asn Xaa Tyr Xaa Xaa
1               5

<210> SEQ ID NO 299
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid

<400> SEQUENCE: 299

Xaa Tyr Tyr Xaa Xaa
1               5

<210> SEQ ID NO 300
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid

<400> SEQUENCE: 300

Xaa His Tyr Xaa Xaa
1               5

<210> SEQ ID NO 301
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 301

```
Xaa Xaa Tyr Xaa Xaa Cys Xaa
1               5

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid

<400> SEQUENCE: 302

Xaa Tyr Xaa Xaa Xaa Xaa Cys Xaa
1               5

<210> SEQ ID NO 303
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 303

Xaa Tyr Xaa Xaa Xaa Trp Xaa
1               5

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(6)
<223> OTHER INFORMATION: Variable amino acid

<400> SEQUENCE: 304

Xaa Xaa Lys Xaa Xaa Xaa Lys
1               5

<210> SEQ ID NO 305
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid

<400> SEQUENCE: 305

Xaa Xaa Gly Lys Xaa Xaa
1               5

<210> SEQ ID NO 306
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid

<400> SEQUENCE: 306

Xaa Xaa Lys Xaa Glu
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid

<400> SEQUENCE: 307

Xaa Xaa Lys Lys Xaa Xaa
1               5

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(6)
```

```
<223> OTHER INFORMATION: Variable amino acid

<400> SEQUENCE: 308

Xaa Xaa Glu Lys Xaa Xaa
1               5

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid

<400> SEQUENCE: 309

Xaa Xaa Lys Leu Xaa Xaa
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 310

Xaa Xaa Lys Xaa Glu Xaa Lys Xaa Xaa
1               5

<210> SEQ ID NO 311
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 311

Arg Gly Gly Arg Gly Gly
1               5

<210> SEQ ID NO 312
<211> LENGTH: 15
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid

<400> SEQUENCE: 312

Xaa Xaa Xaa Xaa Arg Ser Xaa Ser Xaa Pro Xaa Xaa Xaa Xaa Cys
1               5                   10                  15

<210> SEQ ID NO 313
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 313

Arg Xaa Arg Ser Xaa Ser Xaa Pro
1               5

<210> SEQ ID NO 314
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 314

Thr Pro Xaa Xaa Ser Pro
1               5

<210> SEQ ID NO 315
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (10)..(14)
<223> OTHER INFORMATION: Xaa can be any naturally occurring amino acid
```

```
<400> SEQUENCE: 315

Cys Xaa Xaa Xaa Xaa Arg Gly Gly Xaa Xaa Xaa Xaa Xaa
1               5                   10

<210> SEQ ID NO 316
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 316

Pro Xaa Thr Pro Xaa Arg
1               5

<210> SEQ ID NO 317
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is methylarginine
<220> FEATURE:
<221> NAME/KEY: misc_feature
<222> LOCATION: (4)..(4)
<223> OTHER INFORMATION: Xaa is methylarginine

<400> SEQUENCE: 317

Xaa Gly Gly Xaa Gly Gly
1               5
```

PRODUCTION OF MOTIF-SPECIFIC AND CONTEXT-INDEPENDENT ANTIBODIES USING PEPTIDE LIBRARIES AS ANTIGENS

RELATED APPLICATIONS

This application is a continuation of, and claims priority to, U.S. Ser. No. 11/484,485, filed Jul. 11, 2006 (now allowed), itself a continuation-in-part of, U.S. Ser. No. 10/014,485, filed Nov. 13, 2001 (now issued), itself a continuation-in-part of U.S. Ser. No. 09/535,364, filed Mar. 24, 2000 (now issued), which is a continuation-in-part of U.S. Ser. No. 09/148,712, filed Sep. 4, 1998 (now issued), the teachings of which are incorporated by reference herein.

BACKGROUND OF THE INVENTION

The present invention relates to the production of motif-specific, context-independent antibodies which are specific to a short amino acid motif presented in the context of variable surrounding amino acid or peptide sequences. Antibodies with these properties are useful in characterizing various forms of cellular regulation as well as serving to profile genome wide changes in cellular protein levels and protein modification.

Identifying the targets of intracellular signaling cascades are of major importance in understanding cell growth, differentiation, and cell death. Protein kinase cascades relay information from the cell surface to multiple cellular compartments including the nucleus and more distant cell processes such as synapses (Karin et al., Curr. Opin. Cell. Biol. 6:415-424 (1994)). Although a few targets of protein phosphorylation have been identified, most remain unknown, particularly those that regulate cell growth and differentiation. For example, the MAP kinase cascade is known to play an important role in the regulation of cell growth (Lewis et al., Adv. Cancer Res. 74:49-139 (1998), Crowley et al., Cell 77:841-852 (1994)). However, beyond a handful of substrates, few protein targets responsible for the diverse actions of the MAP kinase cascade have been identified (Fukunaga and Hunter, EMBO 16(8):1921-1933 (1997), Stukenberg et al., Curr. Biol. 7:338-348 (1997)).

Another example of cell signaling proteins are the 14-3-3 proteins, which represent a phylogenetically conserved family of phosphoserine binding proteins whose precise role in cell signaling has yet to be determined (Burbelo and Hall, Curr. Biol. 5(2):95-96 (1995)). These proteins represent a large fraction of total brain protein and are known to bind a wide variety of signaling molecules including: ras, raf, bad, cdc25, and many others (Yaffe et al., Cell 91:961-971 (1997)). Recently, it has been shown that 14-3-3 proteins bind specifically to phosphorylated sites on proteins with the following motif: RXRSXS*XP (SEQ ID NO: 313) where S* is phosphoserine and X represents any amino acid (Muslin et al., Cell 84:889-897 (1996), Yaffe et al. supra(1997)).

Similarly, histones have long been known to be modified by acetylation at specific lysine residues. Acetylation of lysine in histones is thought to reduce protein-DNA interactions and serve to open chromatin in regions undergoing transcription (Struhl, Genes & Development, 12:599-606 (1998)). Recently, other proteins associated with transcription complexes have been shown to be acetylated on lysine although the functional significance is unclear (Imhof et al., Curr. Biol. 7:689-692 (1997), Struhl supra (1998)).

Antibodies against phosphotyrosine have proven to be of great value in identifying and characterizing intracellular signaling mechanisms (Ross et al., Nature 294:654 (1981), Kozma et al., Method. Enzymol. 201:28 (1991), White and Backer, Method. Enzymol. 201:65 (1991), Kamps, Method. Enzymol. 201:101 (1991)). Their value derives from two properties; 1) their ability to discriminate whether or not a protein is tyrosine phosphorylated, and 2) their ability to react with a large variety of different proteins. These properties have proven invaluable in tracing intracellular signaling pathways and identifying new targets of activated tyrosine kinases.

Ideally, the most useful phosphotyrosine antibodies should be as general as possible, that is they should recognize phosphotyrosine independently of the protein sequences in which it is embedded (context independent) so as to allow detection of all possible phosphotyrosine residues. The most successful approaches for producing phosphotyrosine antibodies have utilized phosphotyrosine or phosphotyramine coupled via their free amino groups to keyhole limpet hemocyanin using hetero- or bifunctional crosslinking agents (Frackelton et al., Method. Enzymol. 201:79 (1991), White and Backer supra (1991), Wang, Method. Enzymol. 201:53 (1991), Kamps supra (1991)). Although currently produced polyclonal and monoclonal phosphotyrosine antibodies do recognize many different proteins, they often show crossreactivity with other phosphate containing compounds, for example, mononucleotides (Frackelton et al. supra (1991), Kamps supra (1991)). More importantly, most phosphotyrosine antibodies raised in this fashion display variable sequence reactivity, depending not only on the phosphorylated amino acid, but also upon the amino acid sequences surrounding phosphotyrosine. For example, the present inventors have observed that most phosphotyrosine antibodies do not recognize phosphotyrosine preceded by proline as found in the activation loop of JNK and hence do not react significantly with activated (tyrosine phosphorylated) JNK [(Tan et al. unpublished observations)]. The reason for the variable reactivity is likely due to the fact that the phosphotyrosine antigen is not presented directly to the immune system in the context of variable surrounding amino acids, but is instead presented as a hapten, inappropriately coupled to the KLH carrier via artificial linkages. This approach tends to produce antibodies that react well with phosphotyrosine but are sometimes blocked by surrounding amino acids as they are not present in the antigen.

Other approaches have utilized total cellular phosphotyrosine containing proteins as immungens (Glenney, Method. Enzymol. 201:92 (1991), Wang supra (1991)) with considerable success but the context-dependence of the resulting antibody specificities was not carefully determined, although antibodies raised in this fashion did react with a majority of tyrosine phosphorylated proteins. Estimates as to the fraction of tyrosine phosphorylated proteins detected range from 50% to 94% (Kamps supra (1991)).

Attempts to use the above mentioned techniques to produce similar antibodies for phosphoserine and phosphothreonine have met with limited success. Antibodies produced to date have limited crossreactivity and lower affinity for phosphoserine or phosphothreonine probably due to the poor immunogenicity of these phospho-amino acids compared to phosphotyrosine (Heffetz et al., Method. Enzymol. 201:44 (1991)). Context-dependence and low affinity have limited the utility of currently available phosphoserine and phosphothreonine antibodies, especially when compared to phosphotyrosine antibodies.

Site-specific phosphoserine and phosphothreonine antibodies were first described by Nairn et al. in 1982 and have proven to be highly useful tools to study protein phosphorylation (Czernik et al., *Method. Enzymol.* 201:264 (1991), Czernik et al., *Neuroprot.* 6:56-61 (1995)). One drawback of this type of antibody is that a different antibody needs to be produced for each site of interest. Clearly, development of antibodies that detect phosphoserine or phosphothreonine in a substantially context-independent fashion would be desirable for use in tracing serine/threonine kinase cascades and in defining their biological responses. Likewise, development of context-independent phosphotyrosine antibodies would overcome the limitations of currently available antibodies.

Motif-specific, context-independent antibodies would also be useful in identifying new targets of 14-3-3 action (i.e., other proteins phosphorylated at this motif) and in characterizing the protein kinases that phosphorylate these sites. Likewise antibodies reactive against acetylated lysine would serve as useful tools to study the functional significance of acetylation of histones.

Such antibodies can further be used as general reagents for detecting phosphorylation or other enzymatic modification in vitro, such as in high throughput kinase assays for drug screens, as a single antibody can be used to recognize many different phosphorylated substrates. Phosphotyrosine antibodies are currently employed in high throughput kinase assays to screen for selective, high affinity tyrosine kinase inhibitors. Compounds or drugs that block kinase enzyme activity are detected by their ability to inhibit kinase activity as determined by a reduction of phosphotyrosine antibody binding to phosphorylated substrate. Similar assays can be set up to screen for pharmaceutically useful compounds using antibodies produced as described above for phosphoserine, phosphothreonine, or antibodies detecting other protein modifications.

Antibodies that detect short recurring motifs in a context-independent fashion will also be particularly useful in profiling genome wide changes in protein levels and protein modification. For example, the use of context-independent phosphothreonine antibodies and 2D gel electrophoresis to profile genome wide changes in protein phosphorylation (Patterson and Garrels, *Cell Biology: A Laboratory Handbook* 249-257 (1994), Academic Press) as the result of drug treatment or overexpression of a particular protein will undoubtedly prove useful in identifying potential drug-protein interactions and suggest new downstream targets for overexpressed proteins.

SUMMARY OF THE INVENTION

In accordance with the present invention, there is provided a method of producing antibodies that selectively recognize a plurality of peptides or proteins within a genome that contain the same short motif. Motif-specific antibodies of the invention therefore recognize the motif highly independent of the surrounding amino acid, peptide, or protein sequences. The method allows the production of motif-specific, context-independent antibodies that recognize single modified amino acids, for example phosphorylated serine, threonine, and tyrosine, or acetylated lysine, as well other unmodified or modified short motifs of multiple invariant amino acids.

The method encompasses the production and purification of highly context-independent antibodies that recognize specific and highly degenerate amino acid motifs common to multiple peptides or proteins within a genome, such as those found in kinase consensus sequences or other enzyme binding sites. Motifs recognized by the antibodies of the invention typically comprise one to six invariant amino acids. Furthermore, the method can be used to produce highly context-independent polyclonal or monoclonal antibodies.

Antibodies produced by the method of the present invention may be specific to virtually any desired recurring protein motif, either modified or unmodified. In preferred embodiments, the motif includes at least one modified amino acid, such as a phosphorylated, methylated, or glycosylated amino acid. For example, the method can be used to produce antibodies recognizing phosphothreonine alone or phosphothreonine together with several invariant amino acids in a motif, such as found in MAPK substrates, 14-3-3 binding proteins, or CDK consensus phosphorylation sites. It can also be used to produce antibodies specific for other modified amino acids, for example, acetylated lysine or nitrotyrosine, or to detect any short non-unique motif of one or more amino acids, in a highly context-independent fashion. Alternatively, the antibodies may be specific for unmodified motifs, such as those found in protein cleavage motifs, e.g. caspase cleavage motifs.

The invention also provides motif-specific, context-independent antibodies that specifically recognize short motifs comprising all or part of the following: MAPK consensus substrate motifs, CDK consensus substrate motifs, PKA consensus substrate motifs, Akt consensus substrate motifs, PKC consensus substrate motifs, ATM consensus substrate motifs, 14-3-3 consensus binding motifs, PDK1 consensus docking motifs, phosphothreonine-X-(arginine(R)/lysine (K)), PKC Zeta consensus substrate motifs, ABL kinase consensus substrate motifs, insulin receptor consensus substrate motifs, PI3K P85 consensus binding motifs, CaMKII consensus substrate motifs, SRC kinase consensus substrate motifs, CDC2/CDK2 consensus substrate motifs, GSK3 kinase consensus substrate motifs, and proline(P)-(phosphoserine/phosphthreonine)-proline(P). The antibodies of the invention are not limited, however, to these exemplary motifs, and other preferred species of modified motifs within the scope of the invention are described in more detail below.

The present invention further provides a method of profiling large and diverse protein populations on a genome-wide scale by utilizing motif-specific, context-independent antibodies against motifs conserved on such proteins. For example, phosphorylation-specific antibodies allow genome-wide profiling of changes in protein phosphorylation as a result of drug treatment.

The present invention also provides a method of identifying an unknown substrate of a known enzyme through the use of motif-specific, context-independent antibodies which are raised against motifs common to other substrates of the enzyme.

The use of such motif-specific, context-independent antibodies as a reagent for the detection of enzymatic modifications of a given motif within a substrate is also encompassed by the present invention.

BRIEF DESCRIPTION OF THE DRAWINGS

FIG. 1a is a table depicting the specificity of the affinity-purified, polyclonal antibodies produced against a phosphorylated threonine peptide library in Example I, when tested against specific peptides (SEQ ID NOs: 1-13).

FIG. 1b is a table depicting the specificity of the phosphothreonine antibodies of Example I when tested against various phosphopeptide libraries (SEQ ID NOs: 14-29).

FIG. 1d is a table depicting the context-independence of the anti-phosphothreonine antibodies of Example I as shown by immobilized grid.

FIG. 2a is a table depicting the specificity of the affinity-purified, polyclonal antibodies produced against a phosphorylated PXS*P peptide library in Example II (SEQ ID NOs: 30-32).

FIG. 3a is a table depicting the lack of reactivity of the affinity-purified, polyclonal 14-3-3 antibodies of Example III when tested against non-phosphopeptides or phosphopeptides lacking the motif (SEQ ID NOs: 33-40).

FIG. 4a is a table depicting the specificity of the monoclonal antibodies produced against a phosphorylated PXT*PXR (SEQ ID NO:316) library in Example IV (SEQ ID NOs: 41-44).

FIG. 4b is a Western analysis depicting the reactivity of the CDK consensus site monoclonal antibodies of Example IV against phosphorylated and nonphosphorylated RB protein.

FIG. 21 is a Western blot analysis of calyculin A treated A431 cells, using a context-independent antibody specific for the phospho-14-3-3 binding motif #2 (phospho(Ser)-Arg-X-(Tyr/Phe)-X-pSer).

FIG. 22 depicts phospho-ATM/ATR consensus substrate motif-specific, context-independent antibody ELISAs: Signal to noise ratio of phospho versus nonphospho peptides. (S* or T* denote phosphorylated serine or threonine) (SEQ ID NOs: 123-131).

FIG. 23 shows Chk2 transfected and UV treated COS cell extracts immunoprecipitated with Chk2 antibody then detected by Western blotting, using a motif-specific, context-independent antibody specific for phospho-ATM/ATR consensus substrate motif.

FIG. 24 is a Western blot analysis of UV treated COS cells, using a context-independent antibody specific for phospho-ATM/ATR consensus substrate motif.

FIG. 25 depicts phospho-14-3-3 binding motif-specific, context-independent monoclonal antibody ELISAs: Signal to noise ratio of phospho versus nonphospho 14-3-3 binding motif-containing peptides. (T* and S* denote phosphorylated threonine and serine) (SEQ ID NOs: 132-137).

DETAILED DESCRIPTION OF THE INVENTION

Figure 1C:
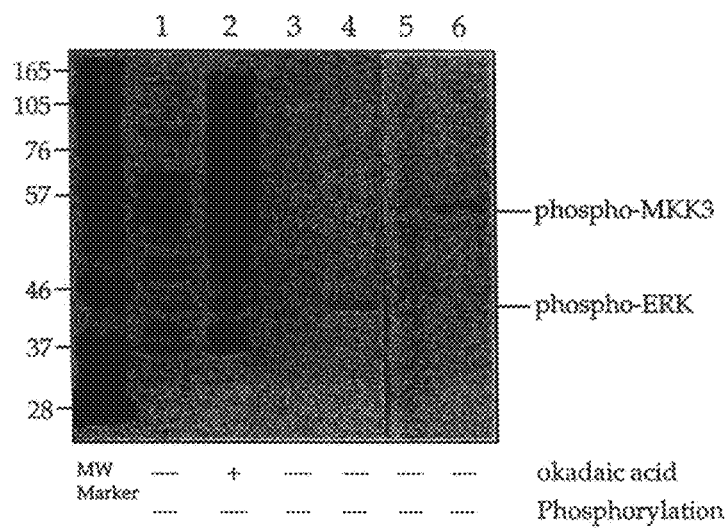
FIG. 1c is a Western analysis which depicts the reactivity of the phosphothreonine antibodies of Example I against cell extracts from cells treated with and without okadaic acid and against other phosphoproteins.

The present invention is based upon the concept that the concentration of any individual sequence in a peptide library used as antigen is extremely low and hence will be insufficient to drive an immune response in a host. The only antigenic determinants of sufficiently high concentration to drive the immune response are thus the fixed (i.e. invariant) residues common to each sequence, as well as the peptide backbone itself.

Immunizing a host with a degenerate peptide library comprising (i) a short fixed amino acid motif (the target motif) containing one or more invariant amino acids, and (ii) a plurality of degenerate amino acids representing many of the 19 amino acids (excepting cysteine) at positions flanking the motif will produce antibodies specific for all or part of the target motif and tolerant to many, if not all, amino acids at the degenerate (i.e. variable) positions flanking the fixed motif. Such antibodies will then react with the antigenic determinant (a motif consisting of all or part of the target motif) despite being presented in the context of a broad range of different surrounding amino acid, peptide, or protein sequences. The highly context-independent antibodies are thus capable of recognizing a plurality of peptides or proteins within a genome that contain the motif, typically consisting of 1-6 invariant amino acids together with one or more post-translationally modified amino acids. The produced antibody may be specific for a motif consisting of a part of the target motif that contains a modified residue, in which case the antibody will recognize peptides and proteins containing that part of the target motif, as well as proteins containing the entire target motif. The invariant residue(s) of the fixed target motif may be a single unmodified or modified amino acid, such as a phosphorylated or unphosphorylated residue, or may be multiple unmodified or modified amino acids, such as a consensus recognition site, comprising a short motif. These short motifs, unlike longer peptide sequences that represent unique protein sequences or sites, frequently serve as targets of enzymatic modification, such as single phosphorylatable residues or consensus substrate or consensus binding sites, which are common to multiple peptide or protein targets in a cell.

As used herein, "antibodies" means polyclonal or monoclonal antibodies, including Fc fragments, Fab fragments, chimeric antibodies, or other antigen-specific antibody fragments.

As used herein, "degenerate amino acids" means amino acid positions that are non-fixed and thus variant. The term includes amino acid positions that are highly degenerate, representing most, if not all, of the 20 amino acids at that position, positions that are moderately degenerate (i.e. biased towards certain of the 20 amino acids), and positions that are slightly degenerate, representing at least two different amino acids.

As used herein, "degenerate peptide library" means a peptide library comprising a plurality of individual peptides collectively containing one or more degenerate amino acids. The term includes a peptide library of any length suitable for use as an immunogen to raise anti-peptide antibodies, typically, but not limited to, about 6 to 20 amino acids.

As used herein, "flanking," with respect to the position of the motif in a peptide library, means to the side or sides of, and does not necessarily mean contiguous or adjacent to.

As used herein, "modified" amino acid as means any naturally-occurring (in vivo) post-translationally modified amino acid, including but not limited to phosphorylated, acetylated, glycosylated, methylated, and ubiquitinated amino acids. Modified amino acids may be singly modified or may contain multiple moieties of the same modification (e.g. doubly- or triply-acetylated arginine, doubly-methylated arginine). Reference to, e.g. "methylarginine" encompasses the various forms, e.g. monomethyl, dimethyl, of such modified amino acid.

As used herein, "motif" means a short amino acid sequence, typically comprising 1 to 6 invariant (i.e. non-degenerate) amino acids including at least one modified amino acid, which occurs in a plurality of peptides or proteins within a genome, and thus is recurring (non-unique). The term includes single amino acid motifs, such as phosphothreonine, and multiple amino acid motifs, such as comprised in kinase consensus substrate motifs, protein binding motifs, phosphatase motifs, or protein cleavage motifs. Motifs including multiple invariant amino acids may also comprise multiple variant (i.e. degenerate) amino acid positions. For example RXRXXT*, the Akt substrate consensus sequence motif, contains 3 invariant amino acids and 3 degenerate amino acids.

As used herein, "motif-specific, context-independent antibody" means an antibody which preferentially recognizes a plurality of peptides or proteins within a genome that contain the motif for which the antibody is specific; the specificity of the antibody is thus substantially independent of the surrounding protein or peptide context in which the antigenic motif occurs. Motif-specific, context-independent antibodies are thus suitable for genome-wide profiling applications, as the antibodies recognize many, if not most, of proteins within a genome containing the motif. The motif that the antibody preferentially binds may consist of all or part of the "target motif" presented in the immunizing degenerate peptide library, but in either case includes any modified amino acid(s) presented in the target motif.

As used herein, "substrate" means any target molecule, including peptides or proteins, which an enzyme specifically recognizes and acts upon.

The general method by which motif-specific, context-independent antibodies are produced in accordance with the present invention is as follows:

(1) Motif-specific antibodies that specifically recognize many different proteins or peptides containing a desired motif substantially independently of the amino acids flanking the motif may be obtained by constructing (e.g. synthesizing), for use as an immunogen, a degenerate peptide library comprising (i) a fixed target motif comprising one or more invariant amino acids, and (ii) a plurality of degenerate amino acids flanking the motif. In a preferred embodiment, the target motif includes at least one modified amino acid. For example, in one preferred embodiment, the library comprises XXXXXXJ*XXXXXXC where X=all 20 amino acids except cysteine, and the motif, J*,=a modified (*) amino acid (J), for example, phosphothreonine (T*) or acetylated-lysine (K*). The terminal cysteine is used to couple the library to a carrier, thus cysteine is excluded from the degenerate positions to avoid unwanted coupling. Other exemplary peptide libraries and motifs are set out in the Examples provided below (e.g. a degenerate library comprising (in place of the J* indicated above) the MAPK consensus substrate motif, PXS*P, is described in Example II). It will be appreciated that the specific target residue(s) of the motif may be unmodified and that a shorter or longer library may be generated and less than all of the degenerate amino acids flanking the motif may be varied.

It will be recognized that a peptide library of any length suitable for use as an immunogen to raise anti-peptide antibodies may be advantageously employed in the practice of the invention. The construction and typical range of length of such peptide antigens has been well described. See e.g., ANTIBODIES: A LABORATORY MANUAL, Harlow and Lane Eds., p. 75-76, Cold Spring Harbor Laboratory (1988); Czernik, supra. at 266-67. Generally, the length of suitable peptide antigen is only limited by the increasing cost and difficulty of synthesizing ever larger peptides, which do not appreciably improve antigenicity. Thus, in one embodiment, the peptide library of the invention is about 6 to 20 residues long. In another preferred embodiment, the peptide library is about 6 to 14 residues long. In still another preferred embodiment, the peptide library is about 6 to 18 residues long.

The peptide library may be constructed, as in a preferred embodiment, with most, if not all, of the amino acids flanking the motif being highly degenerate; the amino acids are those positions are any of the 19 amino acids (excepting cysteine). However, less highly degenerate libraries may alternatively be constructed to contain bias for or against certain residues at particular flanking amino acid positions, or in which less than all of the flanking amino acids are degenerate. For example, in another preferred embodiment, degenerate amino acids at positions flanking the motif may be any amino acid except cysteine (C) and tryptophan (W). Cysteine is excluded to avoid unwanted coupling, as discussed. Tryptophan is excluded because it is a rare amino acid generally, and rarely occurs in positions surrounding modification sites, such as phosphorylation sites, in proteins. Biasing the flanking amino acid positions against W is also believed to reduce the likelihood of generating any antibody response to W, which is a large and somewhat antigenic residue, thus focusing the antibody response of the host on the desired motif. Tyrosine (Y) may also be excluded for the same reason.

Similarly, certain flanking amino acid positions may be biased for particular residues to increase the antigenicity of the immunizing degenerate peptide library. In some cases, it may be known that a given motif adopts a certain structure, in vivo, that is influenced by the presence of particular amino acids surrounding that motif. In such cases, a degenerate peptide library may similarly be constructed with biased flanking residues in an effort to increase the immunogenicity of the fixed motif in the peptide library by introducing structure mimicking that found in vivo. For example, if desired, the influence of particular flanking residues may be determined in advance as follows: A library of peptides that contain a single modifiable target residue, such as phosphotyrosine, and varying flanking residues is constructed. The library is reacted with a desired enzyme, such as a particular kinase of interest, to modify the target residue. The modified peptides are then separated from any unmodified peptides, and batch-sequenced (e.g. by Edman degradation) to examine the abundance of each amino acid at a particular flanking position. An enriched amino acid at a particular flanking position indicates that residue is favored by the enzyme at that flanking position. (per personnel communication, Lewis Cantley). A degenerated peptide library may then be constructed with bias towards the favored residue(s) one or more flanking positions.

In a preferred embodiment, selected flanking amino acids may be biased in order to achieve about 50% representation of one or two amino acids at a given degenerate position in the peptide library and about 50% of all other amino acids except C and W represented at that position. This bias is introduced by biasing the coupling mixture for the desired position during synthesis, described below. By way of further example, in a preferred embodiment (see Example XV(b)), context-independent antibodies specific for the ABL kinase consensus substrate motif (VIY*AXP, where Y*=phosphotyrosine; SEQ ID NO: 97) may be produced by constructing a biased degenerate peptide library comprising CXX<u>A</u>XVIY*A<u>A</u>P<u>F</u>XXX (SEQ ID NO: 98), where bold indicates invariant residues of the motif, X=any amino acid except C and W, and <u>A</u> and <u>F</u>=flanking positions biased 50% towards alanine (A) or phenylalanine (F), respectively (the other 50% representing any amino acid except C or W). Where bias towards two or more amino acids at a given degenerate position is desired, the coupling mixture for that position may be prepared with a total bias of 50% to the desired residues, collectively (e.g. total bias of 50% to K and R (in other words about 25% total bias to each of K and R). It will be recognized that a greater or lesser amount of bias (than 50%) may be advantageously employed. Further examples of such biased peptide libraries are provided in Example XV. It is also anticipated that a mixture of peptides corresponding to approximately 10 known kinase substrates sharing a common motif may be used as an immunogen to generate antibodies to the common motif that are somewhat context-independent.

The degenerate amino acids in the library, including those within or flanking the motif, may be varied at more than one position simultaneously, or, as in the preferred embodiment, varied at only one surrounding sequence position per degenerate molecule, such that a library is produced which is completely degenerate at every position except the fixed residue(s) of the motif. The peptide library can be synthesized by standard F-Moc solid phase peptide synthesis using an ABI peptide synthesizer and using mixtures of each amino acid during degenerate coupling reactions.

The target motif may consist of a single invariant amino acid (either modified or unmodified), or may comprise multiple amino acids, typically 1 to 6 invariant amino acids, representing a short motif common to a plurality of different peptides or proteins within a genome. The uniqueness of a particular peptide sequence is related to its length, since only one of twenty possible amino acids occurs at each position in the peptide chain. Thus, the probability of a sequence of length (n) occurring at random is $1/20$ raised to the nth power. By way of example, for a particular sequence of length 4 (i.e. 4 fixed residues of a motif) there are a total of $(20)4=160,000$ possible amino acid sequence, hence the probability of this specific sequence occurring is $1/160,000=6.25 \times 10^{-6}$. For vertebrate genomes encoding approximately 90,000 proteins of an average length of 500 amino acids, there are approximately 30 million different amino acid sequences, so a 4 amino acid sequence motif would occur at random roughly $(90,000 \times 500) \times 6.25 \times 10-6=300$ times across the entire genome. Similarly, a 5 amino acid motif will occur about 15 times, a 6 amino acid motif will occur around once, and a 7 amino acid motif will occur about 0.05 times across the entire genome.

Thus, from this rough analysis, it is clear that an immunizing peptide sequence should generally be 7 amino acids or greater in length in order to generate an antibody with unique specificity (i.e. not reactive with any other human proteins). For precisely this reason, conventional site-specific peptide immunogens are typically 10-15 amino acids in length, which is small enough to focus the antibody response to the desired region of the protein, yet long enough to ensure multiple overlapping unique epitopes. See, e.g. ANTIBODIES: A LABORATORY MANUAL (1988), supra. Epitopes recognized by native immune system antibodies are typically even larger. Conversely, the range of motif length useful for generating conserved motifs across many proteins is between about 1 to 6 amino acids. This short range comports with both statistical prediction, as discussed above, and the observation that most, if not all, kinase consensus motifs reported to date comprise 6 or fewer invariant amino acids. See, e.g. L. Cantley, "Use of Peptide Libraries to Determine the Substrate Specificity of Protein Kinases," in Cell Signaling Technology, Inc.'s Catalogue and Technical Reference (2000-2001), p. 198; Songyang et al., Current Biology 4: 973-982 (1994); Songyang et al., Mol. Cell. Biol. 16: 6486-6493 (1996); Nishilawa et al., J. Biol. Chem. 272: 952-960 (1990); Kemp et al., Trends Biochem. Sci. 15: 342-346 (1990); al-Obeid et al., Biopolymers 47: 197-223 (1998); Yaffe et al., Nature Biotech. 19: 348-353 (2001); PROTEIN PHOSPHORYLATION: A PRACTICAL APPROACH, D. Hardie ed., p. 267, IRL Press (1993).

In preferred embodiments, the target motif comprises at least one modified amino acid, e.g. a phosphorylated amino acid. Alternatively, the motif may comprise multiple modified amino acids (e.g. T*PXXS*P (SEQ ID NO: 314)), the GSK consensus substrate motif, comprises two phosphorylated residues). In other embodiments, the motif is an unmodified motif, such as protein cleavage motifs (e.g. caspase cleavage motifs). In certain preferred embodiments, the motif is a single phosphorylated amino acid, a single acetylated amino acid, or a single nitrosylated amino acid. Such preferred motifs include, but are not limited to, a single phosphothreonine, a single phosphoserine, a single phosphotyrosine, a single acetyl-lysine, and a single nitrotyrosine. In other preferred embodiments, the motif comprises at least two invariant amino acids including at least one phosphotyrosine or phosphothreonine, or comprises at least one phosphoserine but does not consist of phosphoserine-proline. Another preferred motif is phosphothreonine-X-arginine (T*XR). In other preferred embodiments, the motif comprises all or part of a kinase consensus substrate motif or a protein binding motif. Such preferred motifs include, but are not limited to, all or part of MAPK consensus substrate motifs, CDK consensus substrate motifs, PKA consensus substrate motifs, Akt consensus substrate motifs, PKC consensus substrate motifs, ATM consensus substrate motifs, 14-3-3 consensus binding motifs, and bulky-ring/PDK1 consensus docking motifs. In still other preferred embodiments, the motif comprises all or part of PKC Zeta consensus substrate motifs, ABL kinase consensus substrate motifs, CDK5 consensus substrate motifs, insulin receptor consensus substrate motifs, PI3K P85 consensus binding motifs, CaMKII consensus substrate motifs, Src kinase consensus substrate motifs, CDC2/CDK2 consensus substrate motifs, GSK3 kinase consensus substrate motifs, and proline-phosphoserine-proline (PS*P).

Still other preferred kinase consensus substrate motifs, protein binding motifs, and phosphatase consensus substrate motifs include those listed below in Tables 1 and 2 (s=phosphoserine; t=phosphothreonine; y=phosphtyrosine; k=acetyl-lysine). Table 1 lists published motifs (PMID=PubMed identification number), while Table 2 lists the most common kinase substrate motifs identified from analysis of all published protein phosphorylation sequences (in the PhosphoSite® bioinformatics resource database (www.phosphosite.org)).

TABLE 1

| MOTIF SEQUENCE | SEQ ID NO | KINASE | PMID |
|---|---|---|---|
| RRss | 146 | AGC family | 16020478 |
| RXR[STA][STA][st][FL] | 147 | Akt | 8985174 |
| RXRXX[st] | 148 | Akt | 8985174 |
| [VLIM][RKH]XXX[st]XXX[VLIM] | 149 | AMPK | 7902296 |
| [VLIM]X[RKH]XX[st]XXX[VLIM] | 150 | AMPK | 7902296 |
| [VLIM]XX[RKH]X[st]XXX[VLIM] | 151 | AMPK | 7902296 |
| [VLIMF]X[RKH]XX[st]XXX[VLIMF] | 152 | AMPK | 7698321 |
| [PLIM]X[LIDE]sQ | 153 | ATM | 10608806 |
| LsQE | 154 | ATM family | 10801797 |
| [st]Q | 155 | ATM/ATR/DNA-PK | 10608806 |
| [VLIMF]XRXX[st]XXX[VLIMF] | 156 | CaMK1 | 7698321 |
| [KF][RK][QM][QMKLF]s[VLIMF][DEI][LMKI][FK] | 157 | CaMK2 | 8887677 |
| RXX[st] | 158 | CaMK2 | 1956339 |
| RXXsV | 159 | CaMK2 | 9817025 |
| [VLIFY]XRXX[st][VLIFY] | 160 | CaMK2-alpha | 9452427 |
| [VLIFY]XR[ANDCQEILMFPSTWV]X[st] | 161 | CaMK4 | 9452427 |

TABLE 1-continued

| | | | |
|---|---|---|---|
| [RK]sP[RK][RK] | 162 | Cdc2 | 12586835 |
| [st]PX[RK] | 163 | CDK 1, 2, 4, 5 | 8810285 |
| RXPMsP[PKM][RK]K | 164 | CDK2/cdc2 | 8887677 |
| PL[st]PIP[RKH] | 165 | CDK4 | 7874496 |
| PL[st]PX[RKH] | 166 | CDK4 | 9003781 |
| [KHG]H[HP][KGH]sP[RK][RKH][RKH] | 167 | CDK5 | 11684694 |
| [ST]PG[st]PGTP | 168 | CDK5 | 9003781 |
| [VLIM]X[RK]XX[st] | 169 | Chk1 | 10648819 |
| [st][ED]XX[ST] | 170 | CK1 | 12925738 |
| [st]XX[st] | 171 | CK1 | 2117608 |
| [st]XXS | 172 | CK1 | 12925738 |
| SPXX[st] | 173 | CK1 | 1956339 |
| Y[YE][DY][AD][AG]sl[IYFG][IGF][FG][FPL] | 174 | CK1-gamma | 8887677 |
| [EDA][ED][ED][ED]s[EDA][EDA][ED][ED] | 175 | CK2 | 8887677 |
| [st]XX[ED] | 176 | CK2 | 2044770 |
| [st]XX[EDs] | 177 | CK2 | 12631575 |
| [st]XX[STY] | 178 | CK2 | 15121840 |
| sXX[Est] | 179 | CK2 | 1650349 |
| [RK]X[RK]X[RK]XsXXR | 180 | CLK | 10480872 |
| RXX[st]XXR | 181 | CLK1 | 10954422 |
| RKXRs | 182 | DAPK3 | 15001356 |
| RRKXt | 183 | DAPK3 | 15001356 |
| RRXXs | 184 | DAPK3 | 15001356 |
| [VLIMF]RRXX[st][ILMVF] | 185 | DCAMKL1 | 12590608 |
| RXX[st][VL]R | 186 | DMPK | 10913253 |
| [RK]XRRX[st][VLI]X | 187 | DMPK-E | 12897125 |
| KKXRRt[VLI]X | 188 | DMPK-E | 12897125 |
| RKKXRt[VLI]X | 189 | DMPK-E | 12897125 |
| tPy | 190 | Dual specificity JNK | 11390361 |
| tEy | 191 | Dual specificity MAPK | 12646559 |
| tXy | 192 | Dual specificity MAPK | 11248552 |
| tGy | 193 | Dual specificity p38 | 9295308 |
| RPXsTP | 194 | DYRK1A | 10644696 |
| [TPS][GPEY][PLI][LMP]sP[GPF][PFGY][FYI] | 195 | Erk1 | 8887677 |
| PX[st]P | 196 | ERK1 | 1907971 |
| KsPP | 197 | ERK1, -2, p38, CDK5, GSK-3 | 12586839 |
| sXXX[st] | 198 | GSK3 | 2820993 |
| sXXXSP | 199 | GSK3 | 1956339 |

TABLE 1-continued

| | | | |
|---|---|---|---|
| [RK][st]P | 200 | Histone HI Kinase | 1956339 |
| [st]P[RK] | 201 | Histone HI Kinase | 1956339 |
| LtP | 202 | KSR | 8376361 |
| PLtLP | 203 | KSR | 8376361 |
| PtLP | 204 | KSR | 8376361 |
| tLP | 205 | KSR | 7477354 |
| LXt | 206 | LKB1 | 14985505 |
| XX[FVLA]XRXXsXX | 207 | MAPKAPK-2 | 8280084 |
| sXXX[st] | 208 | MAPKKK | 15629715 |
| [RN][FLM][RK][RK]s[RVIM][RVIM][VIMF][IMF] | 209 | Nek1 | 8887677 |
| GP[QM]sPl | 210 | p38 | 15629715 |
| [RK]RXs | 211 | PAK-gamma | 12384990 |
| [RK][RX]X[st] | 212 | PAKs | 9405039 |
| FXXF[st][FY] | 213 | PDK1 | 11516946 |
| [FMK][RK][MRQF][MFLI]s[LIMF][FRK][LI][FLI] | 214 | Phosphorylase Kinase | 8887677 |
| [RK]XXs[VI] | 215 | Phosphorylase Kinase | 1956339 |
| RKKQIsVR | 216 | Phosphorylase Kinase | 6277942 |
| [RK][RK][RK]X[st] | 217 | Pim1 | 1416988 |
| [RK][RK]X[st] | 218 | PKA | 1956339 |
| KXX[st] | 219 | PKA | 1956339 |
| KXXX[st] | 220 | PKA | 1956339 |
| R[RK]X[st][VLIFY][DCX]XD | 221 | PKA | 14679191 |
| RKXXs | 222 | PKA | 1956339 |
| RRR[RN]sll[FD] | 223 | PKA | 8887677 |
| RRRRsllFI | 224 | PKA | 7874496 |
| RRX[st][VLIFY] | 225 | PKA | 8463304 |
| RXs | 226 | PKA | 1956339 |
| [RK]X[st] | 227 | PKA, PKC | 1956339 |
| RXXs | 228 | PKA, RSK2 | 1956339 |
| [RK][RK]X[st]X[RK] | 229 | PKC | 8887677 |
| [RK]X[st]X[RK] | 230 | PKC | 1956339 |
| [RK]XX[st] | 231 | PKC | 1956339 |
| [RK]XX[st]X[RK] | 232 | PKC | 1956339 |
| ARKGsLRQ | 233 | PKC alpha | 8887677 |
| R[RF]RR[RK]GsF[RK][RK] | 234 | PKC alpha | 8887677 |
| [LRF][RK]R[KQ]Gs[FM]KKXA | 235 | PKC beta | 12566450 |
| RXRKGsF | 236 | PKC delta | 8995387 |
| R[KER]Xs | 237 | PKC epsilon | 8995387 |

TABLE 1 -continued

| MOTIF SEQUENCE | | | |
|---|---|---|---|
| RKQGsVRR | 238 | PKC epsilon | 8995387 |
| ARXXR[RK]RsFRR | 239 | PKC eta | 8995387 |
| RRRK[GK]sF[RK][RK]KA | 240 | PKC gamma | 8995387 |
| [VL][VLA]R[QKE]Ms | 241 | PKC mu | 8995387 |
| FXRXXs[FM][FM] | 242 | PKC zeta | 8995387 |
| [st]X[RK] | 243 | PKC, PKA | 1956339 |
| [RK]XX[st][RK] | 244 | PKG | 9817025 |
| [st]P | 245 | Proline-directed Kinase | 16020478 |
| K[st]PXK | 246 | Proline-directed Kinase | 9819213 |
| KsPXXK | 247 | Proline-directed Kinase | 9592082 |
| KsPXXXK | 248 | Proline-directed Kinase | 9819213 |
| KsPXXXXK | 249 | Proline-directed Kinase | 9592082 |
| KtPAKEE | 250 | Proline-directed Kinase | 9819213 |
| RXXsPV | 251 | Proline-directed Kinase | 15358237 |
| RRFGs[VLIFY]RR[VLIFY] | 252 | SLK1 | 7874496 |
| SsXs | 253 | TGF-beta1 R | 9525694 |

| MOTIF SEQUENCE | | BINDING PROTEIN | PMID |
|---|---|---|---|
| s[VLIMF][EDVI][YF] | 254 | MDC1/BRCT | 14578343 |
| [IL][ILP]tP | 255 | CDC4/WD40 | 11734846 |
| s[FYIVPAKHST][VT]F[GSTNYRKH] | 256 | BRCA1/BRCT | 14578343 |
| tXX[VLI] | 257 | Chk2/FHA | 11106755 |
| RPVSSAAsVY | 258 | 14-3-3 | 9524113 |
| RXRXXsXP | 259 | 14-3-3 | 9524113 |
| RSX[st]XP | 260 | 14-3-3 | 9428519 |
| RX[YF]XsXP | 261 | 14-3-3 | 9428519 |
| KCStWP | 262 | 14-3-3 | 12819209 |
| RXXs | 263 | 14-3-3 | 9524113 |
| YtV | 264 | 14-3-3 | 12196105 |
| s[ED][ED]E | 265 | BARD1/BRCT | 14578343 |
| [st]P | 266 | WW | 11607836 |
| sYll | 267 | RAD9/BRCT | 14578343 |
| DsGXXs | 268 | SCF-Beta/TRCP | 11248545 |
| [PF][VLIFYP][VLIFYAQ][TQHM]S[st] | 269 | Plk1/Polobox | 14532005 |
| S[st]P | 270 | Plk1/Polobox | 15139812 |
| RRVsF | 271 | PP1 | 16426965 |

TABLE 1 -continued

| | | | |
|---|---|---|---|
| KsVTW | 272 | PP1 | 16426971 |
| tXX[DISY] | 273 | FHA | 11106755 |
| MOTIF SEQUENCE | | PHOSPHATASE | PMID |
| tXpY | 274 | PP2C delta | 15807522 |
| tEY | 275 | MKP1 | 16183637 |
| tXpY | 276 | MKP3 | 11432864 |
| PXIXIt | 277 | Calcineurin | 16407284 |

TABLE 2

| MOTIF SEQUENCE | SEQ ID NO |
|---|---|
| XX[st]PX | 278 |
| X[KR]XX[st]XX | 279 |
| X[ST]X[st]XX | 280 |
| XX[st]XXX[ST]X | 281 |
| XX[st]XX[DE]X | 282 |
| XX[st]X[DE]X | 283 |
| X[ST]XX[st]XX | 284 |
| XX[st]XXX[ED]X | 285 |
| XX[st]XXXXPX | 286 |
| RX[st]XX | 287 |
| XX[st][LI]X | 288 |
| XD[st]XX | 289 |
| XX[st]DX | 290 |
| XX[st]QX | 291 |
| X[VLI]yXX | 292 |
| X[DE]XXyXX | 293 |
| XyXX[VL]X | 294 |
| X[DE]XyXX | 295 |
| XXyXX[IM]X | 296 |
| XXyXNX | 297 |
| XNXyXX | 298 |
| XYyXX | 299 |
| XHyXX | 300 |
| XXyXXCX | 301 |
| XyXXXXCX | 302 |
| XyXXXWX | 303 |

Other preferred kinase consensus substrate motifs include XRXRXX[s/t]PX and X[s/t]DXEX.

The incorporation of modified amino acids at invariant (i.e. fixed) positions within the motif in the peptide library should not be limited to phosphorylation or acetylations, as other modified protected amino acids can also be incorporated. For example, motifs comprising one or more amino acids modified with lipids (e.g. farnesylated, isoprenylated) or protected O-linked or N-linked sugars (e.g. glycosylated), methylated, or ribosylated amino acids, or nucleotides, polymers of nucleotides, nucleosides, or amino acids such as ubiquitin, or amino acid analogues may be advantageously employed in the invention. Amino acids modified with residues resulting from the cleavage of a post-translational modification (e.g. gly-gly addition resulting from cleavage of ubitquitin modification) are within the scope of the invention.

In one preferred embodiment, the invention provides a motif-specific, context-independent antibody that specifically binds a recurring, modified motif consisting of (i) two to six invariant amino acids including at least one phosphorylated, acetylated, or methylated amino acid, and, optionally, (ii) one or more degenerate amino acid position(s), said antibody specifically binding said motif in a plurality of non-homologous peptides or proteins within an organism in which it recurs.

Exemplary preferred methylated motifs include, but are not limited to, the following motifs: rGG, rGGrGG (SEQ ID NO: 311), rXr, rG, and GrG (where r=dimethyl-(symmetrical or asymmetrical) arginine). Such motifs are, or may be, important signaling sites for methyltransferase enzymes involved in chromatin regulation, etc.

Exemplary preferred acetylated motifs include, but are not limited to, the motifs listed in Table 3 below (k=acetyl-lysine). These motifs are the most common acetyl-transferase substrate motifs identified from analysis of all published protein acetylation sequences (in the PhosphoSite® bioinformatics resource database (www.phosphosite.org)). Such motifs are, or may be, important signaling sites for acetyltransferase enzymes involved in chromatin regulation, histone modification, etc.

TABLE 3

| Motif Sequence | SEQ ID NO |
|---|---|
| XXkXXXK | 304 |
| XXGkXX | 305 |
| XXkXE | 306 |
| XXKkXX | 307 |
| XXEkXX | 308 |
| XXkLXX | 309 |
| XXkXEXkXX | 310 |

Alternatively, the incorporation of unmodified amino acids at fixed positions in the peptide library may be selected to mimic conserved motifs, for example zinc fingers or repeating arginine residues.

(2) In order to produce as equal a representation of each non-excluded amino acid as possible at each degenerate position, several rounds of altering the amino acid composition, synthesizing, and peptide sequencing are conducted. Amino acid sequence analysis at several different positions along the peptide is conducted to verify a random amino acid representation at each position and that the random representation is maintained throughout the synthesis. It will be recognized by one of skill in the art that the number of rounds may vary in order to achieve an equal distribution of all amino acids at each position.

Alternatively, the representation of particular amino acids at certain degenerate positions in the peptide library may be intentionally biased, as discussed above. For example, in addition to exclusion of cysteine (C) (to avoid unwanted coupling), the rare residue tryptophan (W) may also be generally excluded at each degenerate position. Biasing the degenerate amino acids flanking the motif against W is believed to reduce the likelihood of generating any unwanted antibodies to W, a large, somewhat antigenic residue. Similarly, certain flanking amino acid positions may be biased for particular residues to increase the antigenicity of the immunizing degenerate peptide library, as discussed above. For example, in a preferred embodiment, selected flanking amino acids may be biased in order to achieve about 50% representation of one or two amino acids at a given degenerate position in the peptide library and about 50% of all other amino acids except C and W represented at that position. This bias is introduced at specific degenerate positions by biasing the coupling mixture for the desired position during synthesis, described below. It will be recognized that a greater or lesser amount of bias (than 50%) may be advantageously employed.

(3) The degenerate peptide library is used as an antigen, preferably by covalent coupling to a carrier. In a preferred embodiment, keyhole limpet hemocyanin (KLH) emulsified in Freund's adjuvant is used as the coupling agent, and the coupled peptide library injected intradermally into a host, such as female New Zealand white rabbits, in order to raise context-independent antibodies specific for a motif consisting of all or part of the target motif, but in either case including the invariant modified residue(s) of the target motif. Antibodies of the invention include those specific for either the target motif itself (in which case the antibodies will not recognize peptides or proteins lacking the entire target motif) or for a part of the target motif (in which case the antibodies will recognize peptides or proteins containing only that part of the target motif, as well as those containing the entire target motif). In the latter case, the motif for which the antibody is specific consists of that part of the target motif that is antigenic. Booster injections may be given in incomplete Freund's adjuvant until an immune response is obtained. Antibody titre is measured by a suitable method, such as ELISA against the motif-specific peptide libraries. Antisera raised in this manner may be used in both crude or purified preparations, as outlined below.

For motifs containing invariant positions that may be two or three specific allowable residues, e.g. bulky ring/PDK1 docking motif ((F/Y)(r/S*) or (S*/T*)F) and CDC2/CDK2 consensus substrate motif (S*PR(K/R)), a single degenerate peptide library will typically be constructed with a mixture of allowable residues at such positions, and then coupled to the carrier. Alternatively, however, more than one degenerate peptide library, each with only one of the allowable residues at such positions, may first be constructed, coupled to the carrier for immunization, and then the antisera from immunization with each library mixed together. By way of example, a degenerate peptide library comprising the ATM consensus substrate motif, L(T*/S*)Q(D/E), may be constructed as two distinct degenerate libraries, one comprising LT*Q(D/E) and the other LS*Q(D/E), which are used for immunization separately, and the antisera then mixed together (see, e.g., Example XIII).

(4) Antisera from the most promising hosts are purified, for example over protein A, and adsorbed over a J (non-modified motif) peptide library column. In a preferred embodiment, the nonadsorbed fraction (flow through) is then applied to a J* column (modified motif), eluted at suitable pH, dialyzed and tested for J* (modified motif) specificity by a suitable method, such as ELISA using J* and J as antigen.

(5) Antibodies affinity purified in this fashion recognize the J* (modified motif) peptide library but do not react with the J (unmodified motif) library and exhibit a high degree of specificity for J*. These antibodies may be further tested for lack of reactivity against the unmodified form of the target motif (comprising modified amino acid(s), J*), or a J* homologue, utilizing a suitable method, such as ELISA.

(6) Antibodies may be further tested, as in preferred embodiments, by western blotting or another suitable method, using cell extracts prepared from cells treated with and without a selected protein modification enzyme inhibitor, such as protein phosphatase inhibitor okadaic acid. Treatments that increase protein modification will increase the number of antibody reactive proteins as well as the intensity of reactivity. The J* (modified motif)-specific antibodies will react with a relatively small number of proteins from control extracts but will react with a very large number following treatment with the selected inhibitor. The antibodies will show no reactivity with the inactive-non-modified versions of these proteins, demonstrating a high degree of J* specificity and suggesting broad cross-reactivity to many different proteins within a genome that contain the same modified motif.

(7) The degree of context-independence may be more carefully examined, as in preferred embodiments, for example, by ELISA analysis against individual J* (modified motif) peptides that are mixed together or tested individually. Such analysis can indicate if poor reactivity occurs with certain motifs, such as when J* (modified motif) is followed by proline, for example.

(8) The context-dependence of the J* (modified motif) antibody recognition may be further examined, as in the preferred embodiment, using a immobilized grid of modified-peptide libraries. In addition to a fixed target motif, J*, each different library is synthesized to contain an additional fixed amino acid at different positions relative to J* but with all other positions containing all 20 amino acids except cysteine. Each peptide library is coated, for example, on the bottom of an ELISA well and exposed to the J* antibodies. Motif-specific antibodies that do not react with a particular spot (peptide library) on the grid do not bind when the specified amino acid is present at the specified position. This analysis determines whether or not a particular amino acid at a particular position relative to J* (modified motif) will allow or block binding. Such testing aids in determining whether the antibody is specific for the entire target motif (presented in the degenerate peptide library) or for a part of the target motif, as discussed above. Such testing also confirms the context-independence of the antibody. For example, in a preferred embodiment, the invention provides a context-independent antibody that recognizes a motif consisting of a single phosphothreonine, where the specificity of the antibody is independent of variations in the amino acid residue at the −1 position relative to the motif, as determined by peptide grid (binding) analysis (see Example I).

Alternatively, purified antibodies can be linked to beads, allowed to bind the modified or unmodified library, unbound sequences washed away, and bound sequences recovered and subject to amino acid sequencing to determine the amount of each amino acid present at each position in the library. This information will indicate what amino acids are tolerated at each position.

(9) Monoclonal antibodies may be prepared, as in one form of the preferred embodiment, by coupling the J* (modified motif) degenerate peptide library to a suitable carrier, such as KLH, and injected into a host, such as BalbC mice, in order to raise antibodies specific for the target motif or part of the target motif. The J* peptide-KLH conjugate may be emulsified in Freund's adjuvant and booster injections in incomplete Freund's adjuvant may be carried out every other week until a response is obtained.

(10) Antibody titre is measured by a suitable method, such as ELISA against J* (modified motif) and non-J* peptide libraries. Sera from hosts showing high-titre responses are adsorbed with immobilized non-J* peptide and the nonadsorbed fraction tested by, for example, western blotting.

(11) Spleens from hosts showing J* (modified motif)-specific responses are fused to myeloma cells and hybridoma clones are selected and screened. Supernatants from individual clones are screened first for their ability to bind the J*-peptide library. Positive clones are next screened for their cross-reactivity against the non-J* library. Clones showing the highest degree of J*-specificity are chosen for further analysis as described above in steps (5) through (8).

(12) Overproduction of monoclonal antibodies resulting from step (11) above may be carried out, for example, by harvesting ascites, culturing selected hybridoma clones, or cloning into a host organism, such as *E. coli*.

The motif-specific, context-independent antibodies of the invention produced by this method provide the ability to specifically recognize multiple peptides or proteins within a genome that contain the same motif using a single antibody. In a preferred embodiment, the antibodies of the invention recognize a majority of peptides or proteins containing the motif within a genome. For example, the antibodies of the invention may be used to identify an unknown substrate of an enzyme. In a preferred embodiment, such antibodies are first generated against the modified form of a motif that is recognized by the enzyme of interest, for example, a consensus site. These antibodies are then used to screen a sample for the presence of other, unknown substrates which contain the same modified motif. This method enables the rapid detection of important new substrates in a variety of cascades which involve conserved substrate motifs. For example, antibodies that selectively recognize a wide variety of proteins only when phosphorylated at the MAPK consensus phosphorylation site would greatly facilitate the detection of new MAP kinase targets. The highly context-independent antibodies of the invention enable such genome-wide profiling, as they recognize many of, if not most, peptides or proteins containing the same short motif. MAP kinase could be overexpressed in cell culture, activated by growth factors, and target substrate proteins identified by western blotting using antibodies that selectively recognize the phosphorylated substrate proteins (Stukenberg et al., *Curr. Biol.* 7:338-348 (1997). Alternatively, MAPK could be used to phosphorylate cDNA expression libraries in vitro and MAPK consensus-site antibodies used to identify cDNA clones expressing MAPK phosphorylated substrates (Funkunaga and Hunter, *EMBO* 16(8):1921-1933 (1997). Similarly, the method may be employed to identify new substrates containing specific unmodified motifs, e.g. protein cleavage motifs.

Similarly, motif-specific, context-independent antibodies of the instant invention may be used to identify an enzyme which modifies a known substrate motif. Such antibodies, whether specific for modified (e.g. phosphorylated) or unmodified (e.g. zinc finger) motifs, can be used to detect whether a certain enzyme of interest has modified a substrate which contains that motif. This method allows for the rapid detection of important new proteins which act on known classes of substrates containing contain conserved motifs, for the example MAPK consensus site. In a preferred embodiment, the antibody recognizes the modified form of the motif, and an enzyme sample is reacted with known substrate containing the unmodified form of the motif, and the antibody then used to screen whether any substrate has been modified by the enzyme. Alternatively, the method may be employed to identify enzymes that act on unmodified motifs, such as protein cleavage motifs.

The motif-specific, context-independent antibodies of the invention may also be used in vitro as reagents in high-throughput assays, such as drug screens, to detect the enzymatic modification of certain substrates containing a conserved motif in a cell or tissue. For example, antibodies specific for a certain phosphorylated motif enable the rapid detection of inhibitors of the enzyme that act at that motif. In the case of a drug screen, a single motif-specific antibody can be used to assay the activity of a wide range of enzymes acting at many diverse sequence motifs. Phosphotyrosine antibodies are currently employed in high throughput kinase assays to screen for selective, high affinity tyrosine kinase inhibitors. Compounds or drugs that block enzyme activity are detected by their ability to inhibit kinase activity as determined by a reduction of phosphotyrosine antibody binding to phosphorylated substrate. Similar assays can be set up to screen for pharmaceutically useful compounds using antibodies produced as described above for phosphoserine, phosphothreonine, or antibodies detecting other protein modifications. In a preferred embodiment, the antibody recognizes the modified form of a common motif, and is used to screen an extract of a cell or tissue treated with a drug to profile drug-induced changes in the level or post-translational modification of proteins in the extract that contain the modified motif.

Antibody based detection of protein kinase activity has several advantages over radioactive assays for use in automated high throughput kinase assays. First, radioactive assays are difficult to automate because they employ transfer of 32-P gamma-labeled ATP to a peptide substrate. The phosphopeptide is then separated from labeled ATP using phosphocellulose filters and several washing steps, and finally, phosphorylation is quantitated by liquid scintillation methods. Together these steps are time consuming and difficult to automate. Antibody detection allows a wide variety of ELISA-type assays that are well suited for antomation and high throughput screens.

Second, radioactive assays require low levels of ATP to insure high levels of 32-P incorporation for maximal sensitivity. Low levels of ATP in the kinase assay bias the search for inhibitors towards compounds that compete with ATP binding in the protein kinase catalytic cleft. Such screens consistently yield competitive inhibitors at the ATP binding site which due to the highly conserved nature of this binding site results in inhibitors with poor selectivity.

Current high-throughput kinase assays typically utilize biotinylated peptide substrates immobilized on the bottom of a 96 or 386 well plate that is subsequently incubated together with the desired protein kinase, ATP, and the appropriate kinase buffer. Kinase activity is measured using a fluorescently labeled phosphospecific-antibody that reacts only with the phosphorylated peptide substrate. These assays come in two formats homogeneous (not involving wash steps and heterogeneous (involving wash steps). Homogeneous fluorescent assays typically utilize lanthanide-labelled phosphoantibody binding to a phosphorylated peptide substrate that has linked to it an enery acceptor, for example allophycocyanin. Binding of the phosphoantibody the phosphorylated peptide substrate brings the two fluorophores close enough together to allow fluorescence resonance energy transfer to occur shifting the frequency of the emitted signal, indicating the presence of a biomolecular complex. Different compounds are added to each well and the ability of the compound to inhibit substrate phosphorylation is determined by inhibition of fluorescence energy transfer. This format is similar to the scintillation proximity assay commonly used in radioactive assays. Other homogeneous assays involve the use of fluorescence polarization to measure the binding of phosphoantibody to phosphorylated substrate.

The key feature in the homogeneous assays are the limited number of steps and the ease in automation. A large variety of heterogeneous kinase assays based upon ELIZA formats are also currently in use. These assays typically utilizing fluorescently labeled phosphoantibodies binding phosphorylated peptide substrates that are immobilized in 96 or 386 well formats. In this case wash steps are required to separate bound from unbound antibody. Fluorescently labeled antibody retained in the well is then detected using time resolved fluorescence.

The motifs used to generate antibodies for such modification screening assays may be either modified or unmodified substrate motifs. Antibodies generated against unmodified motifs will not bind if the substrate has been subsequently modified by an enzyme. Similarly, antibodies generated against modified motifs can detect increases in modified substrate concentrations owing to enzymatic activity.

Similar approaches may be applied to study a variety of other enzymatic modifications, and are not limited to the protein kinase or acetyltransferase activities discussed below. For example, the approach could be used to generate antibodies that recognize many other types of protein modification, including, but not limited to, the addition of sugars, methyl groups, carboxyl groups, the addition of various lipids, or the addition of nucleotides, or polymers of nucleotides, nucleosides, or amino acids such as ubiquitin.

Likewise, such motif-specific, context-independent antibodies may be used on a genome-wide scale to simultaneously profile large and diverse protein populations (e.g. in a cell, tissue, or fluid) which contain conserved motifs. A specific two or three amino acid binding site, for example consecutive arginine residues, should appear (based upon a random distribution of amino acids) once every 400 or 8000 residues, respectively, (equating to approximately once per protein, or once every 20 proteins, respectively, (assuming the average protein is 400 amino acids)). Thus, an antibody that specifically recognizes such a motif in a manner that is substantially independent of the context in which it occurs allows for the rapid screening of a great number of proteins or peptides containing the motif. For example, there at least 14 known human proteins containing the AKT consensus substrate motif. See Yaffe et al., supra at p. 350 (Table 1). A context-independent antibody specific for all or part of this motif thus allows for the single-antibody detection of these many motif-containing AKT substrates, as well as the identification of other unknown AKT substrates containing the same consensus motif.

Phosphorylation specific antibodies allow genome wide profiling of changes in phosphorylation of proteins (e.g. in a cell, tissue, or fluid) as a result of drug treatment or the overexpression of specific genes/proteins as a result of such treatment. Such antibodies also facilitate the profiling of expression of specific proteins in sequenced genomes.

For example, suppose that a drug is developed which inhibits the cell-cycle dependent protein kinase cdc2. The drug has been shown to inhibit cdk2 with high affinity, but the specificity of the compound needs to be further tested to examine whether other protein kinases are inhibited and if so, which ones.

As an early step in this process cell lines may be treated with the drug and the effects on total cell protein phosphorylation monitored using a panel of motif-specific and general phosphoantibodies to examine the nature of the phospho-substrates inhibited by the compound or lead drug.

Total protein from cell extracts prepared from control or drug treated cells may be fractionated using, for example, 2-dimentional gels (isoelectric focusing in the first dimension and standard SDS-polyacrylamide molecular weight fractionation in the second dimension), transferred to nitrocellulose membranes, and analyzed by western blotting using, in this hypothetical case, kinase consensus site-specific phosphoantibodies. Alternatively, genome-wide modification may be profiled by analyzing complex mixtures of peptides in cellular digests, as described in U.S. Ser. No. 60/299,893 (Rush et al., filed Jun. 2, 2001, assigned to Cell Signaling Technology, Inc.).

In this case, global analysis of total cell proteins using a cdc2 consensus site specific antibody would provide information regarding the ability of the drug to block phosphorylation at all potential cdc2 site substrates. The pattern of inhibition at other non-cdc2 substrates (i.e. the degree of specificity) could also be examined using antibodies to different kinase consensus sites, or using antibodies to phosphotyrosine to determine whether the inhibitor also acts to block tyrosine kinases.

Currently, for mammalian cells, the identity of the majority of protein "spots" visualized on 2-D gels are unknown. However, as all human genes are identified and sequenced and the corresponding proteins characterized and "spots" identified, analysis by protein profiling in accordance with the present invention will become even more powerfully informative. The identity of the proteins inhibited will not only confirm the drug specificity but the identity of additional "nonspecific" proteins inhibited will also suggest possible side effects. Identical analysis can be carried out in simpler, completely sequenced organisms, such as yeast where many of the protein "spots" on 2-D gels have already been identified.

The Examples presented below are only intended as specific preferred embodiments of the present invention and are not intended to limit the scope of the invention except as provided in the claims herein. The present invention encompasses modifications and variations of the methods taught herein which would be obvious to one of ordinary skill in the art.

Example 1

Context-Independent Phosphothreonine Antibodies

Synthesis of Peptide Library Antigens:

Phospho-specific antibodies that react with any protein containing phosphorylated threonine residues, i.e that bind phosphothreonine independently of the surrounding amino acids, were obtained by synthesizing a highly degenerate peptide library XXXXXXThr*XXXXXXC where X=all 20 amino acids except cysteine and Thr*=phosphothreonine.

The phosphothreonine peptide library was synthesized by standard F-Moc solid phase peptide synthesis using an ABI peptide synthesizer and using mixtures of each amino acid during degenerate coupling reactions. Degenerate peptides were synthesized using an ABI model 433A peptide synthesizer, using FastMoc chemistry (Fields et al., *Pept. Res.* 4:95-101 (1991), hereby incorporated by reference herein) at a scale of 0.085 mmol. Fmoc/NMP chemistry utilizing HBTU amino acid activation (Dourtoglou et al., *Synthesis* 1984: 572-574 (1984), Knorr et al., *Tetra. Let.* 30:1927-1930 (1989), Knorr et al., in *Peptides* 1988 37-129 (1989), Walter de Gruter & Co, all hereby incorporated by reference herein) was employed for all cycles. Preloaded Fmoc-Cys(Trt) HMP (p-hydroxymethylphenoxymethyl)polystyrene resin functionalized at 0.5 mmol/g was used for each degenerate pool of peptides. Peptides were synthesized using single coupling during each cycle, although coupling times were extended at each position containing a phosphorylated amino acid. The final Fmoc was removed during synthesis. Utilization of preloaded HMP resin along with final Fmoc group removal yields peptides having both free amino and carboxy termini after cleavage and deprotection.

In order to produce as equal a representation of each amino acid as possible at each degenerate position several rounds of altering the amino acid composition, synthesizing, and peptide sequencing were conducted. The desired peptide pools were to contain an equimolar mix of 19 amino acids (all standard amino acids except Cys) at each degenerate site. Because the rate of reactivity of each protected amino acid differs, simply mixing equimolar amounts (each at approximately 5.26% of total) does not result in a population of peptides that is equimolar at each position. In order to maximize degeneracy at each residue, peptide synthesis was first done using equimolar "mixes" at each position. Phenylthiocarbamyl-amino acid analysis was performed therefore allowing assessment of relative amino acid content at each position. Based on amino acid analysis the molar amounts of each amino acid in the "mix" were adjusted to compensate for different reaction rates, in order to ensure equal representation of each amino acid at each degenerate position. Several rounds of peptide synthesis followed by amino acid analysis were necessary to optimize the amino acid mix, which resulted in a totally degenerate peptide. The optimized amino acid mix arrived at was as follows: G (4.6%); A (5.6%); V (3.3%); L (2.5%); I (4.25%); S (4.4%); T (8.4%); F (2.25%); Y (6.0%); W (6.8%); M (2.9%); P (2.5%); D (5.8%); N (9.5%); E (6.2%); Q (9.4%); K (6.1%); R (6.4%); H (3.5%).

Cleavage of the degenerate peptides from the resin along with removal of side chain protecting groups occurs simultaneously upon treatment with TFA. The cleavage mixture (Perkin Elmer, Emeryville, Calif. (1995)) consists of the following: 0.75 g phenol, 0.125 ml methyl sulfide, 0.25 ml 1,2-ethanedithiol, 0.5 ml milliQ H2O, 0.5 ml thioanisol, 10 ml TFA. The entire mixture was added to the peptide resin (approx. 300 mg). The resin was flushed with nitrogen and gently stirred at room temperature for 3 hours. The resin was then filtered allowing the peptide to be precipitated into cold (0° C.) methyl-t-butyl ether. The ether fraction was centrifuged allowing collection of the precipitate. The peptide precipitate was vacuum dried, analyzed by mass spectroscopy, and HPLC purified.

A sample of the peptide was dissolved in acetonitrile/water (50:50, v/v) and analyzed on a Perceptive Biosystems (Framingham, Mass.) MALDI-TOF mass spectrometer using 2,4,6-trihydroxyacetophenone plus ammonium citrate as the matrix. As expected, the peptide mixture did not show a homogeneous product. MALDI-TOF analysis demonstrated that the peptide pool was degenerate, showing an average mass and the expected statistically normal curve of peptide mass.

Peptides were purified using a Waters HPLC system consisting of a Lambda-Max Model 481 Multiwavelength detector, 500 series pumps, and Automated gradient controller. A Vydac semi-preparative C18 column was used for reverse-phase purification. A 60 min. linear gradient, 10%-100% B, was used at a flow rate of 2 ml/minute. Buffer A consisted of 0.1% TFA/$H_2O$ (v/v) while buffer B consisted of 0.1% TFA/60% $CH_3CN$/40% $H_2O$ (v/v/v). Detection was at 214 nm.

Because the peptide pool was degenerate (as demonstrated by mass spectroscopy) HPLC purification was not expected to yield a homogeneous product. Base-line separation of peptide mixtures was not achieved by this method and it was only intended as a crude purification/desalting step. Mass spectroscopy was performed and all fractions whose mass was within the theoretical range were pooled and lyophilyzed.

Amino acid sequence analysis at several different positions along the peptide indicated a random amino acid representation at each position and that the random representation was maintained throughout the synthesis. The results indicated the production of highly diverse peptide libraries that would serve as suitable antigens.

Production of Rabbit Polyclonal Antibodies:

All peptides synthesized contained C-terminal cysteine residues allowing conjugation to the carrier protein (KLH) using the heterobifunctional cross-linking reagent m-maleimidobenzoyl-N-hydroxysuccinimide ester (MBS). The conjugation procedure used was as described by the manufacturer (Pierce), although the amount of peptide coupled to KLH was increased to 10 mg in order to provide increased material for immunization and boosting of animals. Scale-up required use of a larger desalting column (Bio-Rad 10 DG (Cambridge, Mass.)) to remove the excess MBS after reaction to N-termini and the ε-amino group of KLH Lysine residues.

The phosphothreonine peptide library was covalently coupled to keyhole limpet hemocyanin (KLH) (250 μgrams), emulsified in Freund's adjuvant and injected intradermally into female New Zealand white rabbits. Booster injections (200 μgrams) in incomplete Freund's adjuvant were carried out every other week until a response was obtained. Rabbit sera was screened at three week intervals for the presence of phosphopeptide specific immunoreactivity by ELISA using both the phosphothreonine and non-phosphothreonine peptide libraries. When the titre of antibody against phosphopeptide reached $10^5$, rabbits were put on a production bleed schedule with bleeds collected every two weeks. When 40 ml of high titre serum were obtained, purification of phosphospecific antibodies was initiated, as described below.

Antisera from the most promising rabbit was purified over protein A and passed over a nonphospho Thr/Ser peptide library column. The nonadsorbed fraction (flow through) was applied to a phosphothreonine column, eluted at low pH, dialyzed and tested for phosphospecificity by ELISA using phospho- and nonphosphopeptides. Antibodies affinity-purified in this fashion recognized the phosphorylated threonine peptide library but did not react with the nonphosphothreonine/serine library, indicating a high degree of specificity for phosphothreonine (see FIG. 1a). ELISA results also indicated that the antibodies also reacted specifically with a mixture of 18 different phosphothreonine peptides but showed no reactivity with any of the corresponding nonphosphopeptides (FIG. 1b). The antibodies also exhibited a strict preference for phosphothreonine, showing no reactivity with a mixture of 38 different phosphoserine peptides (FIG. 1b) or peptides containing phosphotyrosine.

We next tested the antibodies by western blotting using cell extracts prepared from cells treated with and without the protein phosphatase inhibitor okadaic acid. As shown in FIG. 1c the phosphothreonine antibodies react with a relatively small number of proteins from control extracts but react with a very large number following treatment with okadaic acid (see the smear of high Mol Wt. reactive proteins in FIG. 1c, lane 2). The antibodies also reacted specifically with the active forms of MAPK (ERK1) and MKK3 only when phosphorylated at threonine residues at their respective activation loops. The antibodies showed no reactivity with the inactive-nonphosphorylated versions of these proteins (FIG. 1c, lanes 3-6). These results demonstrate a high degree of phosphothreonine specificity and suggest broad cross-reactivity to many different threonine-phosphorylated proteins and peptides.

Figure 2B:
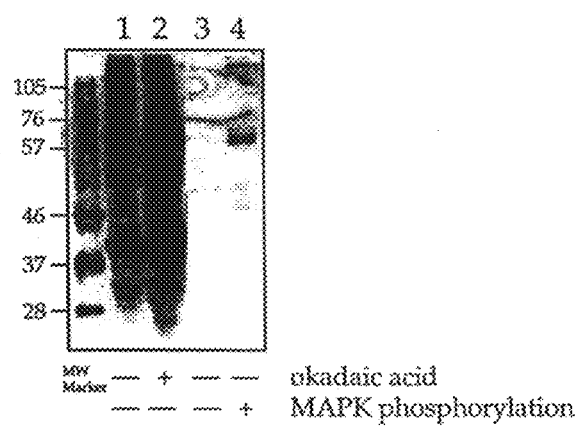
FIG. 2b is a Western analysis depicting the reactivity of the phospho-PXS*P antibodies of Example II against cell extracts from cells treated with and without okadaic acid and against other phosphoproteins.

To examine more carefully the degree of context-independence, ELISA analysis was conducted against individual threonine phosphorylated peptides that were mixed together in the previous experiment. As shown in FIG. 1a, the phosphothreonine antibody reacts well with all phosphopeptides except those where phosphothreonine is immediately followed by proline, for example the c-Myc and APP1 phosphopeptides (FIG. 2b). These results indicate that purified rabbit antibodies reacted in a phosphospecific manner with a wide variety of phosphothreonine but react only poorly with phosphopeptides where the phosphorylated threonine is followed by proline.

The context-dependence of phosphothreonine antibody recognition was further examined using a immobilized grid of phosphopeptide libraries. In addition to a fixed phosphothreonine, each different library was synthesized to contain an additional fixed amino acid at the −4, −3, −2, −1, +1, +2, +3 positions relative to phosphothreonine but with all other positions containing all 20 amino acids except cysteine. Each peptide library was coated on the bottom of an ELISA well and exposed to the phosphothreonine antibodies. Antibodies that do not react with a particular spot (peptide library) on the grid do not bind when the specified amino acid is present at the specified position. This analysis determines whether or not a particular amino acid at a particular position relative to phosphothreonine will allow or block binding (FIG. 1d).

Results confirmed that the phosphothreonine antibodies tolerated all amino acids in the −1, −2, −3, −4, and +2, +3 position, and bound equally well to every amino acid except proline at the +1 position (see FIG. 1d, first row). The reactivity as defined by this binding profile indicates that the antibodies will bind all phosphothreonine containing sequences except those followed immediately in −1 position by proline. Further analysis using a variety of specific phosphothreonine containing peptides confirmed these results.

Phosphothreonine specific antibodies from several other rabbits immunized with the same peptide library antigens were further purified and characterized. Antibodies purified from sera obtained from two other rabbits also produced broadly cross-reacting phosphothreonine antibodies as determined by ELISA. One rabbit produced antibodies that react equally well with peptides containing proline following the phosphothreonine. Taken together, these results demonstrate the broad context-independence of the phosphothreonine response obtained when combinatorial peptide libraries are used as immunogens.

Example II

Protein Kinase Consensus Site-Specific Phosphoantibodies

MAPK-Consensus Recognition Sites: PXS*P

A peptide library of the preferred site for MAPK phosphorylation PXS*P was synthesized (FIG. 2a) substantially as described in Example I. In addition to an equimolar mix of phosphoserine and threonine, amino acids at two other positions were also fixed; proline at −2 and proline at +1. This library was coupled to KLH and injected into rabbits as described for phosphothreonine. IgG from the most promising rabbit was protein A purified and passed over a nonphospho-Thr/Ser peptide library column. The nonadsorbed fraction (flow through) was applied to a phospho-PXS*P column, eluted at low pH, dialyzed and tested for phosphospecificity by ELISA using phospho- and nonphosphopeptides.

Antibodies affinity purified in this fashion reacted strongly with the phosphorylated PXS*P peptide library but did not react with the nonphosphothreonine/serine library (see FIG. 2a). ELISA results also indicated that the antibodies also reacted specifically with a mixture of 18 different phosphothreonine peptides but showed no reactivity with any of the corresponding nonphosphopeptides (FIG. 2a). In addition to being phosphospecific, the antibodies exhibited a preference for proline at the −2 and +1 positions and showed no reactivity with phosphorylated peptides that lack proline at this position (FIG. 2a). The antibodies reacted strongly with the RB and cdk4 phosphopeptides but showed no reactivity with the MKK3, PKCalpha, or p70S6 phosphopeptides that lack proline at the +1 position (FIG. 2a). These antibodies do react with some peptides lacking proline at −2, for example the cdk4 phosphopeptide, suggesting that proline at this position is not absolutely necessary.

PXS*P antibodies were further tested by western blotting using cell extracts prepared from cells treated with and without the protein phosphatase inhibitor okadaic acid. Binding of the PXS*P antibodies to cell extracts from RS 4;11 cells was strongly enhanced following treatment with okadaic acid (smear of high Mol Wt. proteins in FIG. 2b, lane 2). The antibodies also reacted specifically with ATF-2 phosphorylated in vitro with MAP kinase but not the non-phosphorylated form of this protein (FIG. 2b, lanes 3 and 4), demonstrating a high degree of phospho-specificity and broad cross-reactivity to many different phosphorylated proteins and peptides.

The specificity of PXS*P antibody recognition was also examined using an immobilized grid of phosphopeptide libraries. As described above, in addition to a fixed phosphothreonine or phosphoserine, each different library was synthesized to contain an additional fixed amino acid at the −1, +1, +2 positions relative to phosphothreonine but with all other positions containing all 20 amino acids except cysteine.

The PXS*P antibody reacted weakly with peptide libraries where proline was fixed at the −1 position and reacted strongly with libraries where proline was fixed at both the −2 and +1 positions. The reactivity as defined by this binding profile indicates that the PXS*P antibodies strongly bind only sequences containing the PXS*P motif, as expected, but that the antisera still contain some residual reactivity to S*P (as a result of impurities), which could be removed by further purification using immobilized S*P peptide library.

Example III

Protein Kinase Consensus Site-Specific Phosphoantibodies 14-3-3 Binding Site: RSXS*XP (SEQ ID NO: 313)

Antibodies that identify 14-3-3 targets were obtained by synthesizing a peptide library: XXXXRSXS*XPXXXXC (SEQ ID NO: 312) where S* is phosphoserine and X represents any amino acid and C is cysteine. The above 14-3-3 phosphopeptide library was synthesized by standard F-Moc solid phase peptide synthesis using an ABI peptide synthesizer and mixtures of each amino acid except cysteine during degenerate coupling reactions, as discussed in Example I.

Figure 3B:
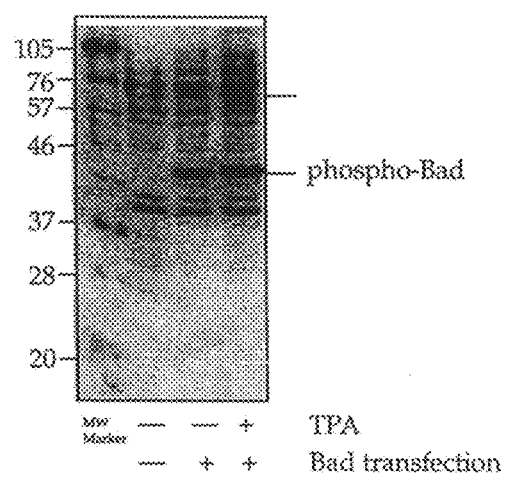
FIG. 3b is a Western analysis depicting the reactivity of the phospho-14-3-3 antibodies of Example III against cell extracts from cells transfected with GST-Bad and with TPA.

The 14-3-3 phosphopeptide library was coupled to KLH and injected into rabbits as described above for phosphothreonine and PXS*P. Antisera from the most promising rabbit was purified over protein A and adsorbed over a nonphospho-14-3-3 peptide library column. The flow-through of this column was applied to a phospho-14-3-3 column eluted at low pH, dialyzed and tested for phospho-specificity by ELISA using phospho- and nonphospho-14-3-3 peptide libraries. These affinity purified phospho-14-3-3 antibodies recognized the phosphorylated 14-3-3 peptide library but not the nonphospho-14-3-3 library, indicating a high degree of specificity for phospho-14-3-3 (see FIG. 3a). The antibodies also reacted strongly with several different peptides containing the 14-3-3 motif including; phospho-Bad-Ser136, cdc25-Ser216, and more weakly with phospho-Bad-Ser112 which contains a slight variant motif. The antibodies showed no reactivity with the corresponding nonphosphopeptides (FIG. 3a) or with many other phosphopeptides that did not contain the motif.

Phospho-14-3-3 antibodies were further tested by western blotting using cell extracts prepared from cells transfected with a GST-Bad fusion protein and treated with and without the phorbol ester TPA. The antibodies reacted with a small number of proteins from control extracts (see FIG. 3b). Bad was detected in extracts prepared from transfected cells but not control cells. Since the basal level of Bad phosphorylation is high it was difficult to see increased phosphorylation with TPA, although TPA did induce the phosphorylation of several higher molecular weight proteins (arrow in FIG. 3b). These results indicate that the phospho-14-3-3 antibodies can detect phosphorylated Bad and other TPA stimulated phosphoproteins.

ELISA analysis against the previously described grid of serine/threonine phosphorylated peptide libraries was also conducted. As expected, the phospho-14-3-3 antibodies have an absolute requirement for proline at the +2 position.

A second, monoclonal, motif-specific, context-independent antibody that recognizes the 14-3-3 motif #1 was also produced, as described in Example XIV(a), below.

Example IV

Production of Mouse Monoclonal Antibodies: CDK Consensus Phosphorylation Site PXT*PXR The PXT*/S*PXR sequence represents a consensus phosphorylation site for many of the cell cycle-dependent proteins kinases (cdks). Antibodies that recognize this phosphorylated motif would be useful to identify new cdk substrates important in controlling cell cycle progression. The PXT*/S*PXR peptide library shown in FIG. 4a was coupled to KLH and injected into Balb/c mice. The phosphopeptide-KLH conjugate (50 µgrams) emulsified in Freund's adjuvant was injected IP. Booster injections (12.5 to 25 µgrams) in incomplete Freund's adjuvant were carried out every three weeks until a response was obtained. Antibody titre was measured by ELISA against the immunized phosphopeptide library. Sera from mice showing high-titre responses were adsorbed with immobilized nonphospho Thr/Ser peptide and the nonadsorbed fraction tested by western blotting (data not shown).

Splenocytes from a mouse showing phosphospecific responses were fused to myeloma X63Ag8.635 cells (Kearney et al., J. Immunol. 123:1548-1550 (1979)) and approximately 1,100 hybridoma clones were selected and screened. Supernatants from individual clones were screened first for their ability to bind the immunized phosphopeptide library and next for their cross-reactivity against the non-phosphopeptide library. Two different clones showing the highest degree of phospho-specificity were chosen for further analysis. The specificity of clones 6B8 and 5A9 were further characterized using the phosphopeptide libraries and phosphopeptides shown in FIG. 4a. Both clones reacted specifically with phosphothreonine containing libraries and individual peptides but did not significantly react with phosphoserine containing peptides, indicating that phosphothreonine selective clones had been identified. Both clones reacted strongly with peptide libraries where proline is fixed in the −2 and +1 positions relative to phosphothreonine. Reactivity against T*P and PXT*P libraries does not indicate relaxed specificity since one of 400 and one of 20 peptides in the respective libraries will have the appropriate amino acids at the fixed positions. Both clones reacted strongly with a single RB phosphothreonine peptide containing each of the fixed positions present in the immunized library but did not react significantly with the corresponding nonphosphopeptide.

Western analysis shows that okadaic acid treatment of cultured cells dramatically increases the reactivity with both clones 6B8 and 5A9 (FIG. 4b). Clone 6B8 is also shown to detect cdc2 phosphorylated RB by western blotting (FIG. 4b) but does not react with nonphosphorylated RB protein. Clone 5A9 was deposited in accordance with the terms and conditions of the Budapest Treaty on Sep. 4, 1998 with the American Type Culture Collection under ATCC Accession No. HB12563.

Subsequent testing indicated the specificity of this antibody requires T*P, a part of the target motif which includes the modified residue. Hence, this motif-specific, context-independent antibody is capable of recognizing multiple proteins that contain a T*P motif, including where this motif is presented within the CDK consensus substrate motif (PXT*PXR) (SEQ ID NO: 316).

Example V

Acetylated-Lysine Specific Antibodies

Antibodies specifically reactive against acetylated lysine but not reactive against non-acetylated lysine were obtained by synthesizing the following acetylated lysine peptide library: XXXXXXK*XXXXXXC where K* is acetylated and X represents any amino acid except cysteine and C is cysteine. The acetylated lysine peptide library was synthesized as described previously by standard F-Moc solid phase peptide synthesis using commercially available fully protected acetylated lysine.

The peptide library was coupled to KLH and injected into rabbits. The K*-peptide-KLH conjugate (250 µgrams) was used as immunogen as described for the other phosphopeptide libraries. Antisera from the most promising rabbit were purified over protein A and adsorbed over a non-acetylated lysine peptide library column. The flow through of this column was applied to an acetylated lysine column, eluted at low pH, dialyzed and tested for phosphospecificity by ELISA.

Figure 5A:
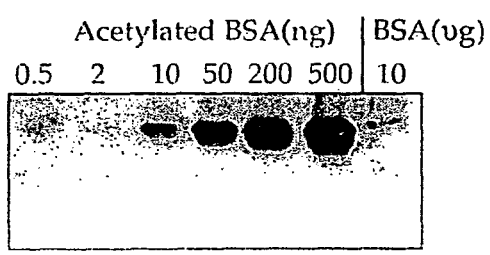
FIG. 5a is a Western analysis depicting the specificity of the acetylated-lysine antibodies of Example V against acetylated BSA.

Acetylated-lysine antibodies, affinity purified as described above, recognized the acetylated lysine peptide library but not the non-acetylated library, indicating a high degree of specificity for acetylated lysine as measured by ELISA. The antibodies also reacted specifically with as little as 0.5 ng of acetylated bovine serum albumin (BSA) but showed no reactivity with up to 10 µgrams of nonacetylated BSA (see FIG. 5a).

Figure 5B:
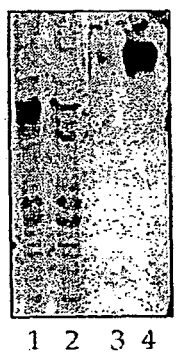
FIG. 5b is a Western analysis depicting the reactivity of the acetylated-lysine antibodies of Example V against various proteins present in C6-cell extracts when antibodies are preincubated with nonacetylated peptide library.
Figure 5C:
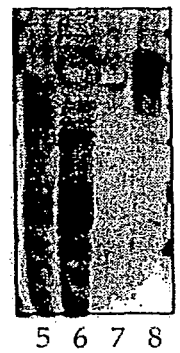
FIG. 5c is a Western analysis depicting the reactivity of the acetylated-lysine antibodies of Example V against various proteins present in C6-cell extracts when antibodies are preincubated with acetylated peptide library.
Figure 5D:
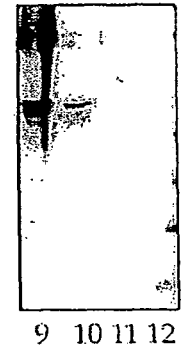
FIG. 5d is a Western analysis depicting the reactivity of the acetylated-lysine antibodies of Example V against the control acetylated BSA when antibodies are preincubated with acetylated peptide library.

The antibodies were further examined by western blotting using cell extracts prepared from cells treated with and without anisomycin. The antibodies react with a number of different proteins present in the C6-cell extracts (FIG. 5b). In panels b and c, antibodies were preincubated with 1 µgram of nonacetylated peptide library (FIG. 5b) or 1 µgram of acetylated peptide library (FIG. 5c). Preincubation with nonacetylated peptide library had little effect on antibody reactivity with acetylated control protein or bands visualized in the cell extract (FIG. 5c, lanes 5-8). However, preincubation of the antibodies with the acetylated lysine peptide library completely blocked antibody binding to control acetylated BSA as well as binding to many proteins present in the cell extract (FIG. 5d, lanes 9-12). These results demonstrate a high degree of specificity for acetylated lysine and indicate that the antibodies recognize a broad spectrum of different sized proteins that contain acetylated lysine in a variety of surrounding sequence contexts (compare FIGS. 5c and d, lanes 1, 2).

Example VI

Phosphoantibody to the Substrate Consensus Sequence for Akt: RXRXXT*

The Akt protein kinase is an important regulator of cell survival and insulin signaling, but very few of its in vivo targets have been identified. Studies with synthetic peptide substrates of Akt (D. R. Alessi et al. FEBS Lett. 399:333-338 (1996)) as well as the analysis of known Akt phosphorylation sites on GSK-3 (T. F. Franke et al. Cell 88:435-437 (1997)), Bad (M. Pap et al. J. Biol. Chem. 273:19929-19932 (1998); Datta et al. Cell 91:231-241 (1997)), FKHR Brunet et al. Cell 96:857-868 (1999)), and Caspase-9 (M. H. Cardone et al. Science 282:1318-1321 (1998)) indicate that Akt phosphorylates its substrates only at a serine or threonine in a conserved motif characterized by arginine at positions −5 and −3.

To study and discover new Akt targets, an antibody was developed that specifically recognizes the phosphorylated form of the Akt substrate consensus sequence RXRXXT*. This antibody was raised against the following synthetic peptide antigen, where X represents a position in the peptide synthesis where a mixture of all twenty amino acids (excluding cysteine) were used, and Thr* represents phosphothreonine: Cys-X—X—X-Arg-X-Arg-X—X-Thr*—X—X—X—X (SEQ ID NO: 45). The synthetic phospho-peptide was conjugated KLH (keyhole limpet hemocyanin) and injected into rabbits. Test bleeds were collected and characterized by ELISA on phospho and non-phospho versions of the peptide antigen.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia ÄKTA FPLC to isolate the IgG antibody fraction. Affinity chromatography is then performed using peptide coupled to Sulfo-Link resin from Pierce (#20401; coupling directions according to manufacturer). Phospho-Akt Substrate Antibody was found to be already highly phospho-specific as crude serum, so that a subtraction step on a column containing the non-phospho peptide was not necessary and the elution from the Protein A column could be used directly for affinity chromatography on a phospho-peptide-containing column. Protein A eluate was incubated with phospho-peptide resin by rotation in a sealed column at room temperature for one hour. Column was then drained, washed twice with PBS, and eluted with 0.1M Glycine, pH 2.7 and pooled fractions neutralized with 1M Tris-HCl, pH 9.5 (~1-2% of fraction volume). The eluted phospho-specific antibody was then dialyzed overnight in PBS at 4° C.

Figure 6:
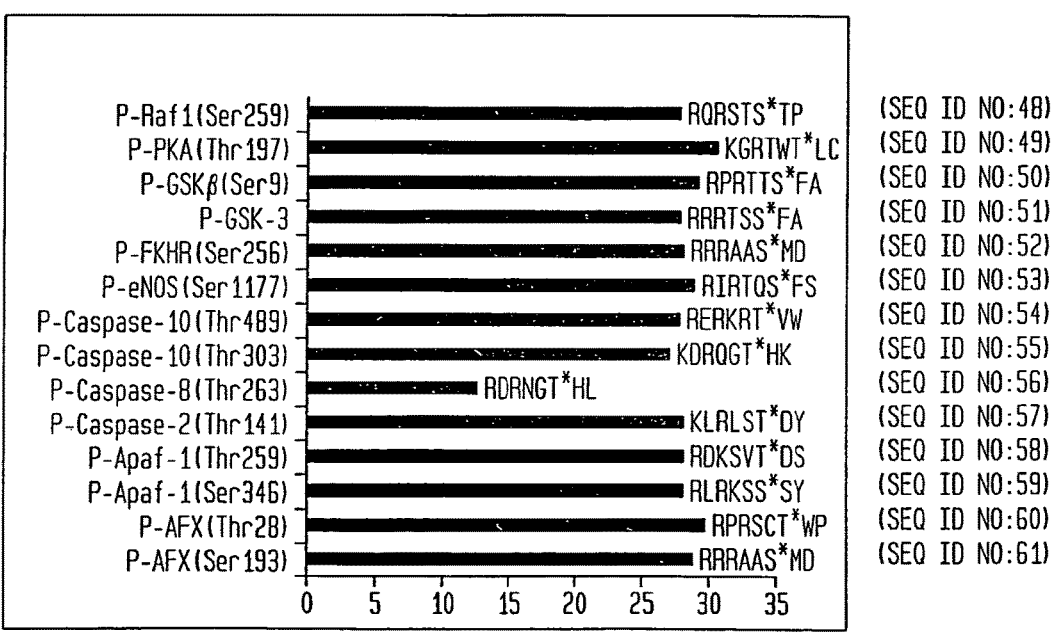
FIG. 6 shows the signal to noise ratio of ELISA readings using phospho-Akt substrate antibody with phospho-peptides of Akt substrates vs. non-phospho-peptides of Akt substrates (SEQ ID NOs: 48-61).
Figure 7:
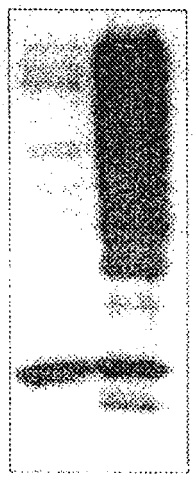
FIG. 7 is a Western analysis of calyculin A-treated A431 cells using phospho-Akt substrate antibody.

The resulting antibody is highly specific for peptides which contain phospho-threonine/serine preceeded by arginine at positions −5 and −3 (FIG. 6). Some cross-reactivity is observed for peptides which contain arginine at positions −3 and −2. (FIG. 6) also shows that this antibody is highly phospho-specific and recognizes these motifs only when phosphorylated (signal to noise ratios were determined as a ratio of reactivity with the phospho-peptide to reactivity with the corresponding non-phospho-peptide). This antibody does not recognize other phospho-threonine/serine containing motifs. (FIG. 7) indicates that in mammalian cells there are many phosphoproteins recognized by this antibody.

A second context-independent antibody that recognizes the Akt substrate consensus motif, RXRXXT* was produced by synthesizing the following biased degenerate peptide library: CXXXRXRTXT*FGXXX (SEQ ID NO: 88), where T* is phosphothreonine and bold indicates invariant motif residues, X represents any amino acid excluding cysteine (C) and tryptophan (W), and underlined residues, T, F, and G=degenerate positions at which the representation of amino acids is biased to 50% of the underlined residue (threonine (T), phenylalanine (F), or glycine (G), respectively) and 50% of all other amino acids excluding cysteine and tryptophan. Bias towards these particular residues at the given degenerate positions was chosen based upon the prior determination of flanking residues (in peptide substrates) favored by Akt kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (T, F, or G, respectively) and the other 50% comprised a mixture of all amino acids, substantially as described in Example 1, excluding C and W.

This biased degenerate peptide library was coupled to KLH and injected into rabbits as described above in Example 1. Antisera from the most promising rabbit was purified over protein A and adsorbed over an unmodified (nonphospho) Akt consensus substrate motif peptide library column. The flow-through of this column was applied to a modified (phospho)-Akt consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies (as with those produced with an unbiased peptide library) are highly specific for the phosphorylated form of all or part of the Akt consensus substrate motif, and will specifically recognize a plurality of different proteins within a genome that contain this motif.

Example VII

Phosphoantibody to the Substrate Consensus Sequence for PKA: RRXT* cAMP-dependent Protein Kinase A (PKA) is an important kinase for regulating a striking number of physiologic processes, including intermediary metabolism, cellular proliferation and neuronal signaling, by altering basic patterns of gene expression (M. Montminy Annual Rev. Biochem. 66:807-822 (1997)). Studies with synthetic peptide substrates have established a consensus phosphorylation site for PKA, namely serine or threonine with arginine at the −2 and −3 positions (Songyang et al., supra.).

To identify and study new in vivo substrates of PKA, an antibody was developed that specifically recognizes the phosphorylated form of the PKA substrate consensus sequence RRXT*. The following synthetic phospho-peptide peptide antigen was used, where X represents a position in the peptide synthesis where a mixture of all twenty amino acids (except cysteine) were used, and Thr* represents phospho-threonine: Cys-X—X—X—X—X-Arg-Arg-X-Thr*X—X—X—X (SEQ ID NO: 46). The synthetic phospho-peptide was conjugated KLH (keyhole limpet hemocyanin) and injected into rabbits. Test bleeds were collected and characterized by ELISA on phospho and non-phospho versions of the peptide antigen.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Protein A eluate was first incubated with non-phospho-peptide resin by rotation in a sealed column at room temperature for one hour, in order to remove antibodies reactive with the non-phospho version of the protein antigen. This resin was then drained and the flow-through then incubated with phospho-peptide resin. This column was drained, washed twice with PBS, phospho-specific antibody eluted with 0.1M Glycine, pH 2.7 and pooled fractions neutralized with 1M Tris-HCl, pH 9.5 (~1-2% of fraction volume). The eluted phospho-specific antibody was then dialyzed overnight in PBS at 4° C.

Figure 8:
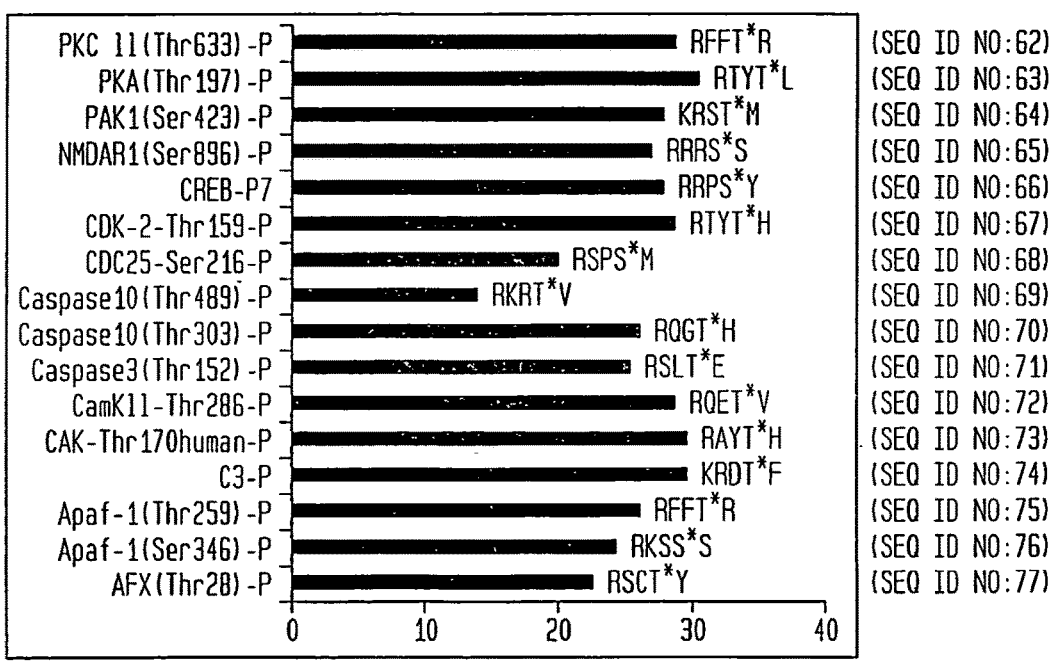
FIG. 8 shows the signal to noise ratio of ELISA reading using phospho-PKA substrates antibody against peptides have arginine or lysine at −3 position (SEQ ID NOs: 62-77).
Figure 9:
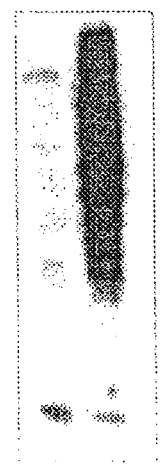
FIG. 9 is a Western analysis of calyculin A-treated A431 cells using phospho-PKA substrates antibody.
Figure 10:
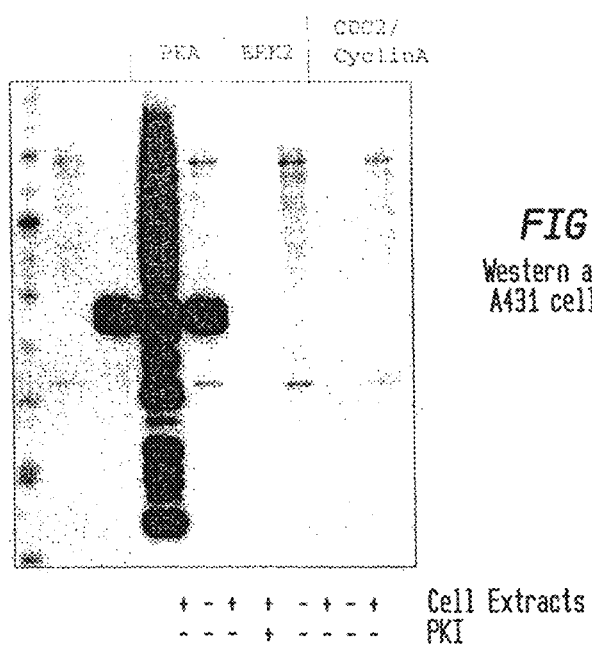
FIG. 10 is a Western analysis of A431 cell extracts phosphorylated by protein kinase A, ERK2 and CDC2/cyclinA in vitro using phospho-PKA substrate antibody.

FIG. 8 shows that the resulting antibody is highly specific for peptides or proteins containing phospho-threonine with arginine at the −3 position. The antibody also recognizes some proteins containing phospho-serine with arginine at the −2 and −3 position. It does not recognize the non-phosphorylated version of these motifs (as shown by the signal to noise ratios in FIG. 8 which were determined as a ratio of reactivity with the phospho-peptide to reactivity with the corresponding non-phospho-peptide); nor does the antibody recognize other phospho-serine/threonine containing motifs. FIG. 9 indicates that in mammalian cells there are many phosphoproteins recognized by this antibody, while FIG. 10 shows that this antibody specifically detects many PKA protein substrates in a cell but will not recognize substrates of the ERK2 or CDC2 kinases, which have different substrate specificities.

Example VIII

Phosphoantibody to the Substrate Consensus Sequence for Bulky Ring-Directed Kinases/PDK1 Docking Motif: [F/Y][T/S]* or [S/T]*F Some important classes of protein kinases are regulated by phosphorylation of a specific serine or threonine flanked by either phenylalanine or tyrosine. For example, Akt, which plays a central role in regulating cell survival, is activated by phosphorylation at Ser473, a site flanked by phenylalanine and tyrosine (D. R. Alessi et al. EMBO J. 15:6541-6551 (1996)). RSK1 (Ser381) and the PKC's also contain this consensus site, phosphorylation of which is required for their activity (K. N. Dalby et al. J. Biol. Chem. 273:1496-1505 (1998); L. M. Keranen et al. Curr. Biol. 5:1395-1403 (1995)).

To help study signaling pathways regulated by phosphorylation at these key regulatory sites we developed an antibody that detects phospho-serine and phospho-threonine only when preceded by tyrosine, tryptophan or phenylalanine or when followed by phenylalanine (the "bulky-ring kinase"/PDK1 consensus docking motif. This antibody was raised against the following synthetic peptide antigen, where X represents a position in the peptide synthesis where a mixture of all twenty amino acids (except cysteine) were used, and Ser* or Thr* represents phospho-serine or phospho-threonine: X—X—X—X—F—X—X—F—[S*/T*]-[F/Y]-X—X—X—X—C(SEQ ID NO: 47). This synthetic phospho-peptide was conjugated to KLH and injected into rabbits. Test bleeds were collected and characterized by ELISA on phospho and non-phospho versions of the peptide antigen.

Once rabbits stared to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Two rounds of subtractive purification were performed using the non-phospho-peptide resin: Protein A eluate was incubated with non-phospho-peptide resin by rotation in a sealed column at room temperature for one hour, in order to remove antibodies reactive with the non-phospho version of the protein antigen. The column was drained and the flow-through (containing the desired antibody) incubated with fresh non-phospho-peptide resin. The flow-through from this second subtractive step was finally positively purified by incubation with phospho-peptide resin. After the phospho-peptide column was drained and washed twice with PBS, phospho-specific antibody (bound to the resin) was eluted with 0.1M Glycine, pH 2.7 and pooled fractions were neutralized with 1M Tris-HCl, pH 9.5 (~1-2% of fraction volume). The eluted phospho-specific antibody was then dialyzed overnight in PBS at 4° C.

Figure 11:
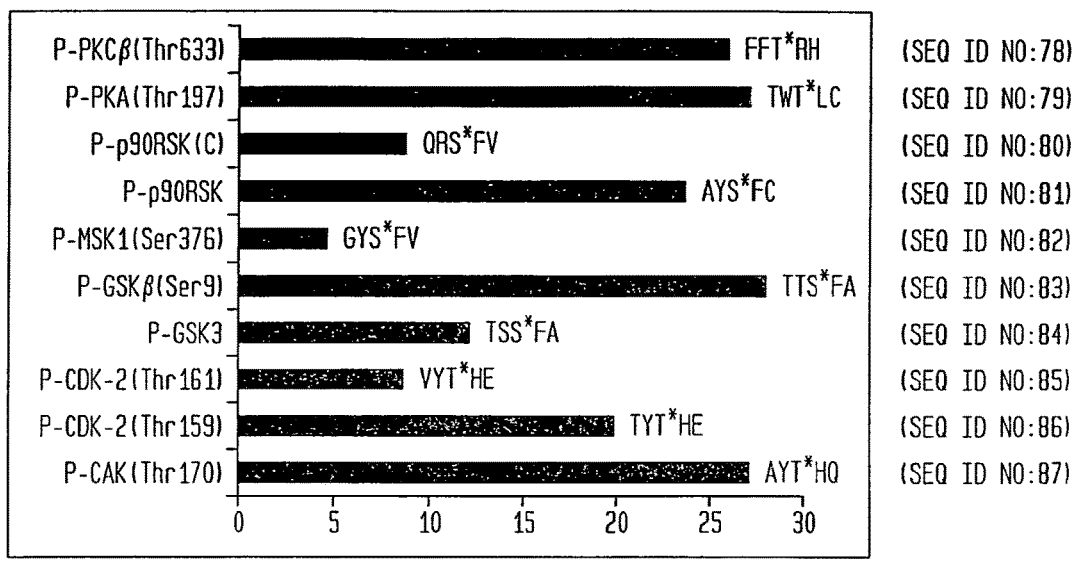
FIG. 11 shows the signal to noise ratio of ELISA reading using phospho-serine/threonine phenylalanine antibody against the peptides containing phenylalanine, tyrosine or tryptophan (SEQ ID NOs: 78-87).
Figure 12:
FIG. 12 is a Western analysis of calyculin A-treated A431 cells using phospho-serinine/phenylalanine substrates antibody.

The resulting antibody is highly specific for phosphorylated [F/Y][T/S]- or [S/T]F-containing peptides (FIG. 11). It does not recognize non-phosphorylated [F/Y][T/S] or [S/T]F motifs or other phospho-serine/threonine containing proteins and peptides (signal to noise ratios were determined as a ratio of reactivity with the phospho-peptide to reactivity with the corresponding non-phospho-peptide). This antibody does not recognize other phospho-threonine/serine containing motifs. FIG. 12 indicates that in mammalian cells there are many phosphoproteins recognized by this antibody.

A second, monoclonal, motif-specific, context-independent antibody that recognizes the bulky ring/PDK1 consensus docking motif was also produced, as described in Example XIV(b), below.

Example IX

Context-Independent Antibody Specific for the PKC Consensus Substrate Motif:
(K/R)S*(F/L/V)(K/R)(K/R)

Although Protein Kinase C (PKC) family members are involved in a number of cellular signal transduction processes including secretion, gene expression, proliferation and muscle contraction (K. Nishikawa et al. (1997) J. Biol. Chem. 272:952-960; R. B. Pearson and B. E. Kemp (1991) Methods Enzymol. 200:62-81), many of its substrates remain unidentified. Isozymes of PKC are subdivided into conventional PKCs (cPKC), novel PKCs (nPKC) and atypical PKCs (aPKC). PKCalpha, beta I, beta II, and gamma isoforms belong to cPKC (K. Nishikawa et al. (1997) J. Biol. Chem. 272:952-960). When activated, cPKC isozymes phosphorylate substrates containing serine or threonine, with arginine or lysine at the −3, −2 and +2 position, and hydrophobic amino acids at position +1 (K. Nishikawa et al. (1997) J. Biol. Chem. 272:952-960; R. B. Pearson and B. E. Kemp (1991) Methods Enzymol. 200:62-81; T. Obata et al. (2000) J. Biol. Chem. 275:36108-36115).

To assay PKC activity and identify and characterize new in vivo substrates of PKC, a context-independent antibody was produced that specifically recognizes the phosphorylated form of the PKC substrate consensus sequence (K/R)(K/R)S*(F/L/V)(K/R)(K/R). The following synthetic degenerate peptide library was constructed, substantially as described in Example 1, where invariant residues of the motif are indicated in bold (K/R means lysine or arginine must be present at that position; F/L/V means phenylalanine, leucine, or valine must be present), X represents any amino acid except W, C, or Y (further excluded in this example because of its size), and S* is phosphoserine: CXXX(K/R)(K/R)S*(F/L/V)(K/R)(K/R)XXX (SEQ ID NO: 89) The synthetic phospho-peptide was conjugated to KLH (keyhole limpet hemocyanin) and injected into rabbits, substantially as described in Example 1.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptides coupled to SulfoLink resin from Pierce (#20401; coupling directions according to manufacturer). Both phospho-peptide-containing resin and the corresponding non-phospho-peptide resin were prepared. Two rounds of subtractive purification were performed using the non-phospho-peptide resin: Protein A eluate was incubated with non-phospho-peptide resin by rotation in a sealed column at room temperature for one hour, in order to remove antibodies reactive with the non-phospho version of the protein antigen. The column was drained and the flow-through (containing the desired antibody) incubated with fresh non-phospho-peptide resin. The flow-through from this second subtractive step was finally positively purified by incubation with phospho-peptide resin. After the phospho-peptide column was drained and washed twice with PBS, phospho-specific antibody (bound to the resin) was eluted with 0.1M Glycine, pH 2.7 and pooled fractions were neutralized with 1M Tris-HCl, pH 9.5 (~1-2% of fraction volume). The eluted phospho-specific antibody was then dialyzed overnight in PBS at 4° C.

Figure 13:
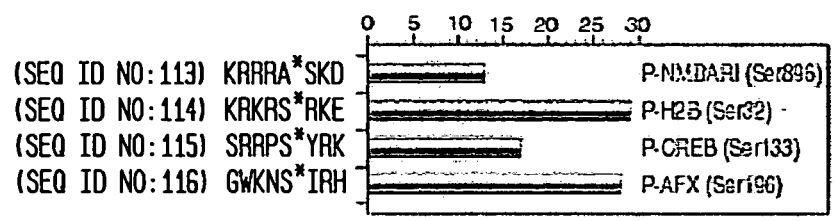
FIG. 13 shows signal to noise ratio of ELISA reading, using a motif-specific, context-independent antibody specific for the phospho-PKC consensus substrate motif, with phospho-PKC substrate containing peptides and nonphospho peptides (SEQ ID NOs: 113-116).
Figure 14:
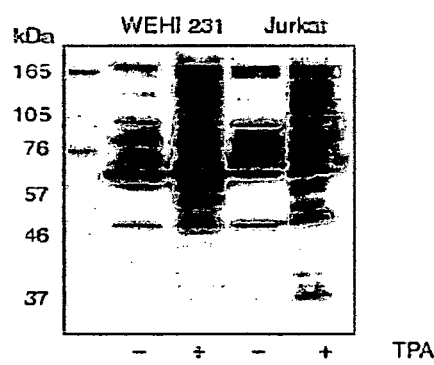
FIG. 14 is a Western blot analysis of WEHI 231 cells or Jurkat cells untreated (−) or treated (+) with TPA, probed with a motif-specific, context-independent antibody specific for the phospho-PKC consensus substrate motif.
Figure 15:
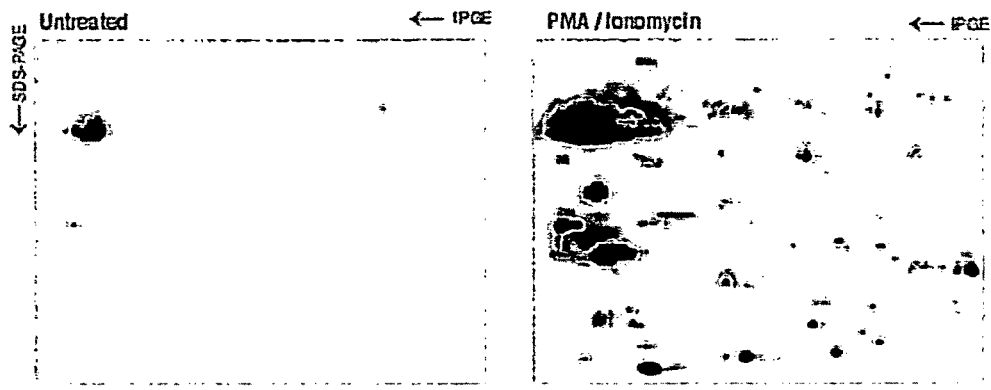
FIG. 15 is a Western blot analysis of whole cell lysates of Jurkat cells untreated and treated with PMA (50 ng/ml) and ionomycin (1 µM) for 20 minutes prior to lysis, using a motif-specific, context-independent antibody specific for the phospho-PKC consensus substrate motif. Proteins were separated by 2D electrophoresis prior to blotting.

The resulting antibody was characterized by ELISA on phospho and non-phospho versions of the peptide antigen. By ELISA Phospho-(Ser) PKC Substrate Antibody detects phosphorylated serine residue in a number of peptide sequences with Arg or Lys at the −2 and +2 position and a hydrophobic residue at the +1 position relative to phospho-serine (FIG. 13). Western blot analysis with the antibody shows that it recognizes a plurality of different proteins within a genome in response to TPA treatment (known to stimulate PKC signaling; FIG. 14). FIG. 15 resolves these TPA-stimulated epitopes better by performing 2-dimensional electrophoresis prior to western blotting.

Example X

Context-Independent Antibody Specific for a Single Nitrotyrosine Motif

Nitric oxide (NO) is implicated in carcinogenesis (B. G. Bentz et al. (2000) Head Neck 22:64-70), chronic infection, inflammation (M. Jaiswal et al. (2000) Cancer Res. 60:184-190) and neurodegeneration (R. Olivenza et al. (2000) J. Neurochem. 74:785-791). High levels of both superoxide and nitric oxide in these tissues interact to form peroxynitrite, a potent oxidant that can modify Tyr residues in proteins to form 3-nitrotyrosine (L. A. MacMillan-Crow et al. (1996) Proc. Natl. Acad. Sci. USA 93:11853-11858). Tyrosine nitration of mitochondrial manganese superoxide dismutase results in loss of enzymatic activity (L. A. MacMillan-Crow et al. (1996) Proc. Natl. Acad. Sci. USA 93:11853-11858). The nitration of p53 at Tyr residues abolishes its capacity for binding to its DNA consensus sequence (L. Chazotte-Aubert et al. (2000) Biochem. Biophys. Res. Commun. 267:609-613).

To study known nitro-tyrosine-containing proteins and identify new ones, a context-independent antibody was developed that specifically recognizes a motif consisting of a single nitrated tyrosine ($YNO_2$). The following synthetic degenerate peptide library was constructed, substantially as described in Example 1, where bold indicates the invariant residue of the motif, X represents a degenerate flanking position where any amino acid except cysteine may occur, and $YNO_2$ represents nitrated tyrosine: CXXXXXX($YNO_2$)XXXXXXX. The degenerate peptide library was conjugated to KLH (keyhole limpet hemocyanin) and injected into rabbits, substantially as described in Example 1.

Once rabbits started to show high nitro-tyrosine-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptides coupled to SulfoLink resin from Pierce (#20401; coupling directions according to manufacturer). Both nitro-tyrosine-peptide resin and the corresponding non-nitrotyrosine peptide resin were prepared. Two rounds of subtractive purification were performed using the non-nitro-tyrosine peptide resin: Protein A eluate was incubated with non-nitro-tyrosine peptide resin by rotation in a sealed column at room temperature for one hour, in order to remove antibodies reactive with the non-nitrated version of the protein antigen. The column was drained and the flow-through (containing the desired antibody) incubated with fresh non-nitro-tyrosine peptide resin. The flow-through from this second subtractive step was finally positively purified by incubation with nitro-tyrosine peptide resin. After the nitro-tyrosine peptide column was drained and washed twice with PBS, nitro-tyrosine-specific antibody (bound to the resin) was eluted with 0.1M Glycine, pH 2.7 and pooled fractions were neutralized with 1M Tris-HCl, pH 9.5 (~1-2% of fraction volume). The eluted nitro-tyrosine-specific antibody was then dialyzed overnight in PBS at 4° C.

Figure 16:
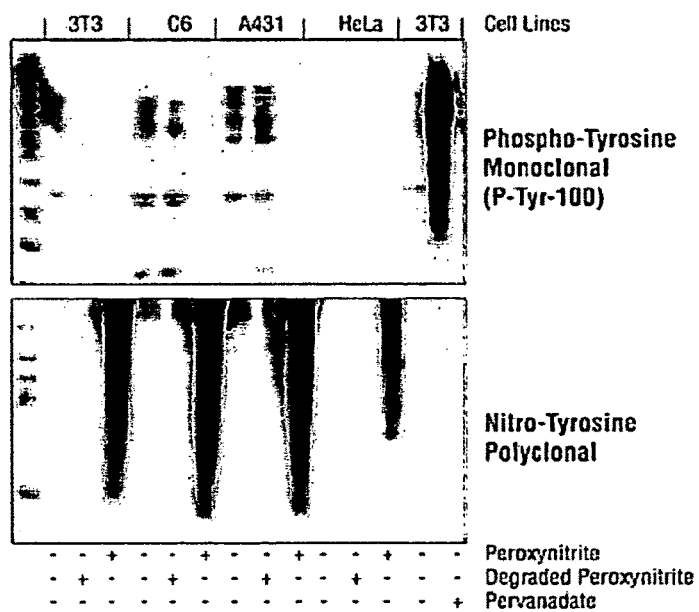
FIG. 16 is a Western analysis of whole cell lysates of different cells untreated or treated with peroxynitrite, degraded peroxynitrite or pervanadate using a context-independent antibodies specific for phosphotyrosine (upper), and a polyclonal context-independent antibody specific for nitrotyrosine (lower).
Figure 17:
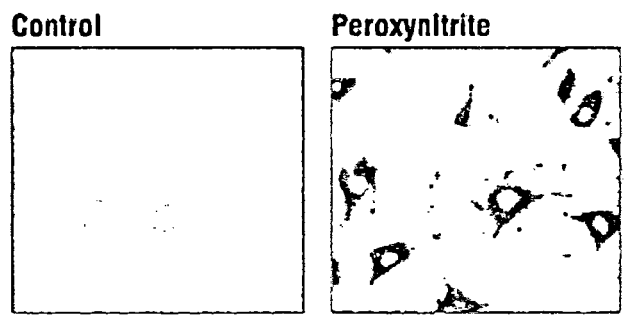
FIG. 17 shows immunocytochemical staining of NIH/3T3 cells treated with degraded peroxynitrite (control) or peroxynitrite using a polyclonal context-independent antibody specific for nitrotyrosine (brown).

The resulting antibody was characterized by ELISA on nitrated and non-nitrated versions of the peptide antigen. The nitrotyrosine polyclonal antibody is highly specific for nitrated tyrosine, in a manner substantially independent of surrounding amino acid sequence. It does not recognize unmodified tyrosine residues or tyrosine modified by phosphorylation. Reactivity with in vivo epitopes is shown in FIG. 16, where extracts of cells treated with Peroxynitrite show enhanced western blot signal, indicating reactivity with a plurality of different nitrotyrosine-containing proteins, but cells treated with degraded peroxynitrite (which will not cause tyrosine nitration) or with pervanadate (which causes tyrosine phoshporylation but not nitration) do not show increased immunoreactivity by western blot, as expected. FIG. 17 shows a similar result, increased immunoreactivity in peroxynitrite-treated cells, this time using the antibody for immunocytochemistry.

Example XI

Context-Independent Antibody Specific for the Phosphothreonine-X-Arginine Motif

Some important signaling proteins can be regulated by phosphorylation at a specific threonine followed by arginine or lysine at the +2 position. For example, conventional PKC isozymes phosphorylate substrates containing serine or threonine with arginine or lysine at the −3, −2 and +2 position (K. Nishikawa et al. (1997) J. Biol. Chem. 272: 952-960; R. B. Pearson and B. E. Kemp (1991) Methods Enzymol. 200:62-81). c-Raf, a mitogen-activated protein kinase and the main effector recruited by GTP-bound Ras, is phosphorylated at threonine 481 and 491 followed by lysine at the +2 position (B. Zhang, and K. Guan (2000) EMBO J. 19:5429-5439). APP1 and ERF also contain a phosphorylated threonine followed by arginine or lysine at the +2 position. Phosphorylation of these sites is important for the regulation of the activity of these proteins.

To assay the activity of basic-directed kinases, study their substrates and identify new substrates, a context-independent antibody was developed that specifically recognizes the phosphothreonine-X-arginine (T*XR) motif. The following degenerate peptide library was constructed, substantially as described in Example 1, where bold indicates invariant residues of the motif, X represents degenerate flanking positions in the peptide synthesis where a mixture of all 20 amino acids excluding cysteine was used, and T* represents phosphothreonine: CXXXXXX**T*X**RXXXX. The degenerate peptide library was conjugated to KLH (keyhole limpet hemocyanin) and injected into rabbits.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Two rounds of subtractive purification were performed using the non-phospho-peptide resin: Protein A eluate was incubated with non-phospho-peptide resin by rotation in a sealed column at room temperature for one hour, in order to remove antibodies reactive with the non-phospho version of the protein antigen. The column was drained and the flow-through (containing the desired antibody) incubated with fresh non-phospho-peptide resin. The flow-through from this second subtractive step was finally positively purified by incubation with phospho-peptide resin. After the phospho-peptide column was drained and washed twice with PBS, phospho-specific antibody (bound to the resin) was eluted with 0.1M Glycine, pH 2.7 and pooled fractions were neutralized with 1M Tris-HCl, pH 9.5 (~1-2% of fraction volume). The eluted phospho-specific antibody was then dialyzed overnight in PBS at 4° C.

Figure 18:
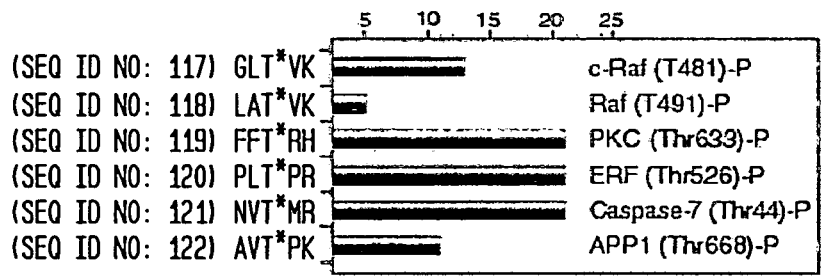
FIG. 18 depicts phosphothreonine-X-arginine motif-specific antibody ELISAs: Signal to noise ratio of phospho versus nonphospho peptides containing the phospho-threonine-X-arginine motif. (T* denotes phosphorylated threonine) (SEQ ID NOs: 117-122).
Figure 19:
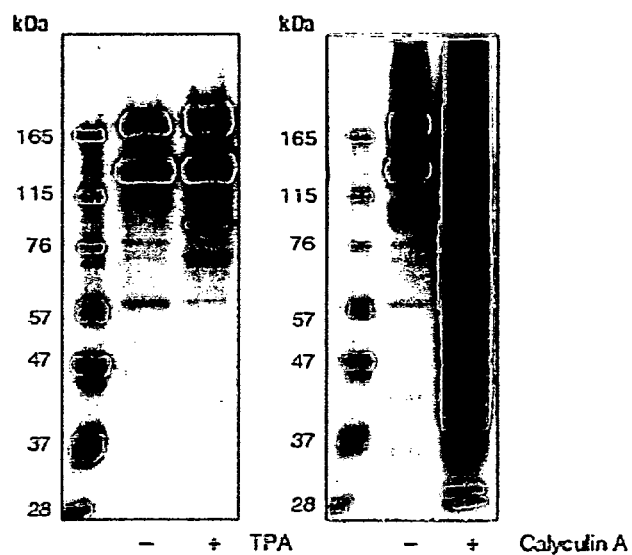
FIG. 19 is a Western blot analysis of Jurkat cell extracts untreated (−) and treated (+) with TPA or Calyculin A, using a motif-specific, context-independent antibody specific for the phosphothreonine-X-arginine motif.
Figure 20:
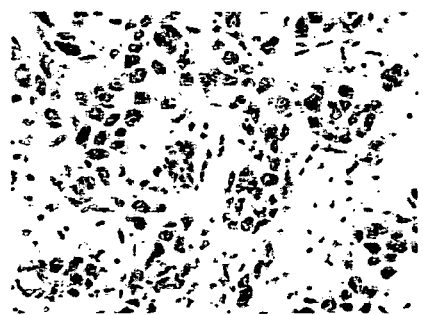
FIG. 20 shows immunohistochemical staining of proteins containing phosphorylated threonine-X-arginine motifs in paraffin-embedded human breast carcinoma, using a context-independent antibody specific for the motif.

The resulting antibody was characterized by ELISA on phospho and non-phospho versions of the peptide antigen (FIG. 18). Phosphothreonine-X-Arginine antibody detects phosphorylated threonine followed by arginine or lysine at the +2 position, though its reactivity for lysine at the +2 position is somewhat lower than for arginine. The antibody does not cross-react with non-phosphothreonine or with phospho-serine in the same motif. It recognizes phospho-threonine in the FFT*R motif in PKC beta II, but does not recognize phospho-threonine in other motifs that lack lysine or arginine at +2. Calyculin A treatment of cells in FIG. 19, inhibiting phosphatases and thereby enhancing protein phosphorylation, shows the antibody recognizes a plurality of different proteins containing the same motif. FIG. 20 shows immunostaining of a breast cancer tissue section using this antibody, indicating the relevance of this epitope in signaling in tumor tissue.

Example XII

Context-Independent Antibody Specific for 14-3-3 Binding Motif #2: RX(F/Y)XS*

The 14-3-3 proteins are a highly conserved family of proteins involved in the regulation of cell survival, apoptosis, proliferation and checkpoint control (A. Aitken (1995) Trends Biochem. Sci. 20: 95-97; J. Zha et al. (1996) Cell 87:619-628; H. Piwnica-Worms (1999) Nature 401:535-537; G. Tzivion et al. (1998) Nature 394:88-92; Xing, H. (2000) EMBO J. 19:349-358). Binding of 14-3-3 is phospho-serine-dependant (Yaffe et al., supra.). Two different phospho-serine containing motifs are found using a degenerate phospho-serine-oriented peptide library technique, RSXS*XP (SEQ ID NO: 313) and RX(Y/F)XS*XP (SEQ ID NO: 90) (Yaffe et al., supra.). Motif 2 (RX(Y/F)XS*XP) (SEQ ID NO: 90) is found in critical regulatory proteins including cdc25a, cdc25b, PKCg, IRS-1 and BCR (Yaffe et al., supra.).

To identify and characterize proteins that contain motif #2 and potentially bind 14-3-3, a context-independent antibody was developed that specifically recognizes the 14-3-3 motif #2, RX(F/Y)XS*X, without the requirement for proline +2 to the phosphoserine. The following degenerate peptide library was constructed, substantially as described in Example 1, where bold indicates invariant residues of the motif, X represents any amino acid except cysteine, and S* represents phosphoserine: XXXRX(F/Y)XS*XPXXXC (SEQ ID NO: 91). The degenerate peptide library was conjugated to KLH (keyhole limpet hemocyanin) and injected into rabbits, as described in Example 1.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Two rounds of subtractive purification were performed using the non-phospho-peptide resin: Protein A eluate was incubated with non-phospho-peptide resin by rotation in a sealed column at room temperature for one hour, in order to remove antibodies reactive with the non-phospho version of the protein antigen. The column was drained and the flow-through (containing the desired antibody) incubated with fresh non-phospho-peptide resin. The flow-through from this second subtractive step was finally positively purified by incubation with phospho-peptide resin. After the phospho-peptide column was drained and washed twice with PBS, phospho-specific antibody (bound to the resin) was eluted with 0.1M Glycine, pH 2.7 and pooled fractions were neutralized with 1M Tris-HCl, pH 9.5 (~1-2% of fraction volume). The eluted phospho-specific antibody was then dialyzed overnight in PBS at 4° C.

The resulting Arg-X-(Tyr/Phe)-X-Ser* motif-specific, context-independent antibody recognizes the 14-3-3 binding motif #2, although the recognition does not absolutely require proline in the +2 position. Thus, the antibody recognizes a large part of the target motif including the phosphorylated residue. The antibody provides a powerful new tool for the discovery and characterization of potential 14-3-3 binding motif #2-containing proteins or other proteins with the RX(F/Y)XS* motif. Calyculin A treatment of cells in FIG. 21, inhibiting phosphatases and thereby enhancing protein phosphorylation, shows that this antibody is substantially context-independent, recognizing a plurality of different proteins, in vivo, that contain the same motif.

Example XIII

Context-Independent Antibody Specific for ATM Consensus Substrate Motif: L(T*/S*)Q(D/E)

ATM (ataxia telangiectasia mutated kinase) and ATR (ataxia telangiectasia and rad3-related kinase) are related kinases that regulate cell-cycle checkpoints and DNA repair (M. B. Kastan and D. S. Lim (2000) Nature Reviews Mol. Cell. Biol. 1:179-186.) The identified substrates for ATM are p53, p95/NBS1, MDM2, Chk2, BRCA1, CtIP, 4E-BP1 and Chk1 (M. B. Kastan and D. S. Lim (2000) Nature Reviews Mol. Cell. Biol. 1:179-186; H. Zhao and H. Piwnica-Worms (2001) Mol. Cell. Biol. 21:4129-4139). The essential consensus sequence for the substrates of ATM/ATR is (S/T)Q. Hydrophobic amino acids and negatively charged amino acids immediately N-terminal to serine or threonine are positive determinants and positively charged amino acids in the region are negative determinants. The complex phenytype of AT cells suggests that it must have other cellular substrates as well (S. T. Kim et al. (1999) J. Biol. Chem. 274:37538-37543).

To assay ATM activity and identify and characterize new ATM and ATR substrates, a context-independent antibody was produced that specifically recognizes a plurality of different proteins within a genome containing the phosphorylated substrate motif, (S*/T*)Q. The following two degenerate peptide libraries were synthesized, substantially as described in Example 1, where bold indicates invariant residues of the motif, where X represents a degenerate flanking position where a synthesis mixture of all 20 amino acids excluding cysteine was used, and where S* is phosphoserine and T* is phosphothreonine: CXXXXXXLT*Q(D/E)XXXXX and CXXXXXXLS*Q(D/E)XXXXX (SEQ ID NOs: 92 and 93). These two degenerate peptide libraries were separately conjugated to KLH (keyhole limpet hemocyanin) and injected into rabbits, as described in Example 1, and the antisera resulting from each immunization were then mixed.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) AKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Two rounds of subtractive purification were performed using the non-phospho-peptide resin: Protein A eluate was incubated with non-phospho-peptide resin by rotation in a sealed column at room temperature for one hour, in order to remove antibodies reactive with the non-phospho version of the protein antigen. The column was drained and the flow-through (containing the desired antibody) incubated with fresh non-phospho-peptide resin. The flow-through from this second subtractive step was finally positively purified by incubation with phospho-peptide resin. After the phospho-peptide column was drained and washed twice with PBS, phospho-specific antibody (bound to the resin) was eluted with 0.1M Glycine, pH 2.7 and pooled fractions were neutralized with 1M Tris-HCl, pH 9.5 (~1-2% of fraction volume). The eluted phospho-specific antibody was then dialyzed overnight in PBS at 4° C.

The resulting antibody was characterized by ELISA on phospho and non-phospho versions of the peptide antigens (FIG. 22). Phospho-(Ser/Thr) ATM substrate consensus antibody detects various peptide sequences that contain phosphorylated serine or threonine when followed by glutamine at the +1 position and preceded by hydrophobic amino acids at the −1 position. In FIG. 23, extracts of COS cells treated with UV and probed by western blot with this antibody show enhanced protein phosphorylation in cells treated with UV, relative to untreated cells, indicating a plurality of different proteins contain this motif. Similarly, FIG. 24 shows by western blot that this antibody recognizes the motif in a known ATM substrate, Chk2; Chk2 was immunoprecipitated from cells treated with UV (known to stimulate ATM signaling), and by western blotting shows increased immunoreactivity relative to untreated cells.

Example XIV

Monoclonal Motif-Specific, Context-Independent Antibodies Specific for Protein Binding Motifs A. 14-3-3 Binding Motif #1

As described in Example XII above, the 14-3-3 proteins are a highly conserved family of proteins involved in the regulation of cell survival, apoptosis, proliferation and checkpoint control. Two different phospho-Ser-containing motifs are found within nearly all known 14-3-3 binding proteins. Motif #1 (RSXS*XP) (SEQ ID NO: 313) is found in critical regulatory proteins including Bad, cdc25c, FKHRL1, PKC and c-Raf (H. Xing (2000) EMBO J. 19:349-358; Yaffe et al., supra.). The production of a polyclonal motif-specific, context-independent antibody that recognizes a plurality of different proteins within a genome that contain the 14-3-3 motif #1 was described in Example III.

A monoclonal context-independent antibody specific for part of this motif was produced by constructing, substantially as described in Example 1, the following degenerate peptide library (somewhat similar to that described in Example III): CXXXRSXS*XPXXX (SEQ ID NO: 94), where S* is phosphoserine, bold indicates invariant residues of the motif, and X is any amino acid except cysteine. The degenerate peptide library was conjugated to KLH (keyhole limpet hemocyanin) and injected into mice, as described in Example 1. Splenocytes from mice showing phosphospecific responses were selected and fused to produce hybridomas substantially as described in Example IV.

Figure 26:
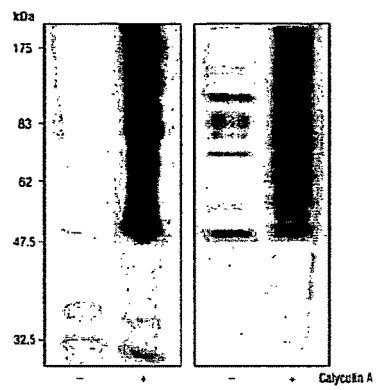
FIG. 26 is a Western blot analysis of calyculin A treated A431 cells, using antibodies specific for phospho-14-3-3 binding motif #1 (left, monoclonal; right, polyclonal).

Clones were screened, as described, and clone 4E2 was selected for further analysis. The resulting antibody produced by clone 4E2 was characterized by ELISA on phospho and non-phospho versions of the peptide antigen (FIG. 25). Phospho-14-3-3 binding motif monoclonal antibody detects phosphorylated serine in various peptides in the context of arginine at the −3 position, and proline at the +2 position. Calyculin A treatment of cells in FIG. 26, inhibiting phosphatases and thereby enhancing protein phosphorylation, shows that this antibody recognizes a plurality of different proteins containing this motif.

Clone 4E2 was deposited in accordance with the terms and conditions of the Budapest Treaty on Oct. 31, 2001 with the American Type Culture Collection (ATCC) and received Patent Accession No. PTA-3823.

B. Bulky-Ring/PDK1 Consensus Docking Motif

As described in Example VIII above, many critical protein kinases can be regulated by phosphorylation at a specific serine or threonine in a hydrophobic motif. RSK2, p70 S6 K and certain PKC isoforms also contain a similar consensus phosphorylation motif, FXXF(S*/T*)(F/Y). Phosphorylation of these motifs is required for binding to 3-phosphoinositide-dependent kinase 1 (PDK1) (M. Frodin et al. (2000) EMBO J. 19:2924-2934; A. Balendran et al. (1999) J. Biol. Chem. 274:37400-37406; A. Balendran et al. (2000) J. Biol. Chem. 275:20806-20813). The production of a polyclonal motif-specific, context-independent antibody that recognizes a plurality of different proteins within a genome that contain the bulky-ring/PDK1 consensus docking motif was described in Example VIII.

A monoclonal context-independent antibody specific for this motif was produced by constructing, substantially as described in Example 1, the following degenerate peptide library (identical to that described in Example VIII): XXXXFXXF(S*/T*)(F/Y)XXXXC, where S* is phosphoserine and T* is phosphothreonine, bold indicates invariant residues of the motif, and X is any amino acid except cysteine. The degenerate peptide library was conjugated to KLH (keyhole limpet hemocyanin) and injected into mice, as described in Example 1. Splenocytes from mice showing phosphospecific responses were selected and fused to produce hybridomas substantially as described in Example IV.

Figure 27:
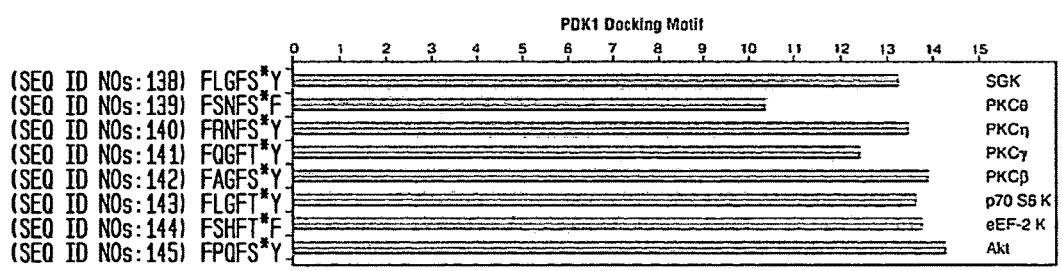
FIG. 27 depicts phospho-PDK1 docking motif-specific, context-independent monoclonal antibody ELISAs: Signal to noise ratio of phospho versus non-phospho peptides corresponding to potential PDK1 docking motifs. (T* and S* denote phosphorylated threonine and serine) (SEQ ID NOs: 138-145).
Figure 28:
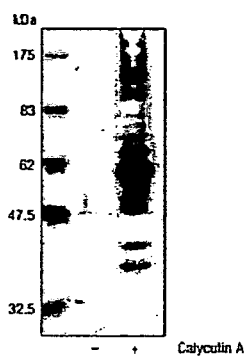
FIG. 28 is a Western blot analysis of extracts from A431 cells untreated or treated with 0.1 μM calyculin A for 30 minutes prior to lysis, using a monoclonal context-independent antibody specific for the phospho-PDK1 docking motif.
Figure 29:
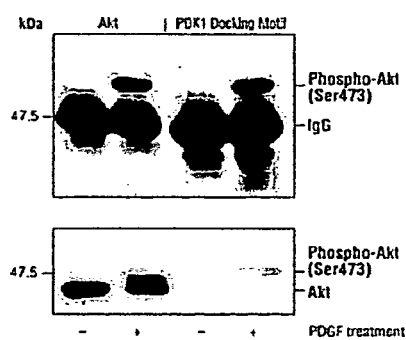
FIG. 29 shows immunoprecipitation of extracts from NIH/3T3 cells untreated or treated with 100 ng/ml of PDGF for 20 minutes prior to lysis, using a monoclonal context-independent antibody specific for phospho-PDK1 docking motif and an Akt antibody, then probed with the PDK1 docking motif monoclonal antibody (upper) and the Akt antibody (lower).

Clones were screened, as described, and clone 18A2 was selected for further analysis. The resulting antibody produced by clone 18A2 was characterized by ELISA on phospho and non-phospho versions of the peptide antigen (FIG. 27). This phospho-PDK1 docking motif monoclonal antibody detects phosphorylated serine or threonine that is surrounded by tyrosine or phenylalanine at the −1 and +1 position and phenylalanine or lysine at the −4 position. Calyculin A treatment of cells in FIG. 28, inhibiting phosphatases and thereby enhancing protein phosphorylation, shows that this motif-specific, context-independent antibody recognizes a plurality of different proteins within a genome that containing this motif. FIG. 29 shows that this antibody works for immunoprecipitation, namely that it will recognize the phospho-PDK1 docking motif within Akt following Akt phosphorylation in response to PDGF treatment (a treatment know to stimulate Akt signaling).

Clone 18A2 was deposited in accordance with the terms and conditions of the Budapest Treaty on Oct. 31, 2001 with the American Type Culture Collection (ATCC) and received Patent Accession No. PTA-3824.

Example XV

Context-Independent Antibodies Specific for Other Motifs

A. PKC Zeta Consensus Substrate Motif

PKC Zeta (protein kinase C zeta) is a kinase that phosphorylates its substrates at a short consensus motif, FXRXXT*FF (SEQ ID NO: 95). Context-independent antibodies specific for the PKC Zeta consensus substrate motif, FXRXXT*FF, were produced by synthesizing the following biased degenerate peptide library: CXRRFKRQGT*FF YFFXX (SEQ ID NO: 96), where T* is phosphothreonine and bold indicates invariant motif residues, X represents any amino acid excluding cysteine (C) and tryptophan, and underlined residues, R, K, Q, G, Y, and F=degenerate positions at which the representation of amino acids is biased to 50% of the underlined residue (arginine (R), lysine (K), glutamine (Q), glycine (G), tyrosine (Y), or phenylalanine (F), respectively) and 50% of all other amino acids excluding cysteine and tryptophan. Bias towards these particular residues at the given degenerate positions was chosen based upon the prior determination of flanking residues (in peptide substrates) favored by PKC Zeta kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (R, K, Q, G, Y, or F, respectively) and the other 50% comprised a mixture of all amino acids, substantially as described in Example 1, excluding C and W.

The PKC Zeta motif degenerate peptide library was coupled to KLH and injected into rabbits as described above in Example 1. Antisera from the most promising rabbit was purified over protein A and adsorbed over an unmodified (nonphospho) PKC Zeta consensus motif peptide library column. The flow-through of this column was applied to a modified (phospho)-PKC Zeta consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the PKC Zeta consensus substrate motif, and will specifically recognize a plurality of different proteins within a genome that contain this motif.

B. ABL Consensus Substrate Motif

ABL (Abelson protein tyrosine kinase) is a kinase that phosphorylates its substrates at a short consensus motif, VIY*AXP (SEQ ID NO: 97). Context-independent antibodies specific for the ABL kinase consensus substrate motif, VIY*AXP (SEQ ID NO: 97), were produced by synthesizing the following biased degenerate peptide library: CXX AXVIY*AAPFXXX (SEQ ID NO: 98), where Y* is phosphotyrosine and bold indicates invariant motif residues, X represents any amino acid excluding cysteine (C) and tryptophan (W), and underlined residues, A, and F=degenerate positions at which the representation of amino acids is biased to 50% of the underlined residue (alanine (A) or phenylalanine (F), respectively) and 50% of all other amino acids excluding cysteine and tryptophan. Bias towards these particular residues at the given degenerate positions was chosen based upon the prior determination of flanking residues (in peptide substrates) favored by ABL kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (A or F, respectively) and the other 50% comprised a mixture of all amino acids, substantially as described in Example 1, excluding C and W.

The ABL kinase consensus motif degenerate peptide library was coupled to KLH and injected into rabbits as described above in Example 1. Antisera from the most promising rabbit was purified over protein A and adsorbed over an unmodified (nonphospho) ABL kinase consensus motif peptide library column. The flow-through of this column was applied to a modified (phospho)-ABL kinase consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the all or part of the phosphorylated form of the ABL consensus substrate motif, and will specifically recognize a plurality of different proteins within a genome that contain this motif.

C. CDK5 Consensus Substrate Motif

CDK5 (cyclin dependent kinase 5) is a kinase that phosphorylates its substrates at a short consensus motif, KXXXT*PXHR (SEQ ID NO: 99). Context-independent antibodies specific for the CDK5 consensus substrate motif, KXXXT*PXHR (SEQ ID NO: 99), were produced by synthesizing the following biased degenerate peptide library: CXXKHHKT*PKHRXX (SEQ ID NO: 100), where T* is phosphothreonine and bold indicates invariant motif residues, X represents any amino acid excluding cysteine (C) and tryptophan, and underlined residues, H, and K=degenerate positions at which the representation of amino acids is biased to 50% of the underlined residue (histidine (H) or lysine (K), respectively) and 50% of all other amino acids excluding cysteine and tryptophan. Bias towards these particular residues at the given degenerate positions was chosen based upon the prior determination of flanking residues (in peptide substrates) favored by CDK5 kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (H or K, respectively) and the other 50% comprised a mixture of all amino acids, substantially as described in Example 1, excluding C and W.

The CDK5 consensus substrate motif degenerate peptide library was coupled to KLH and injected into rabbits as described above in Example 1. Antisera from the most promising rabbit was purified over protein A and adsorbed over an unmodified (nonphospho) CDK5 consensus motif peptide library column. The flow-through of this column was applied to a modified (phospho)-CDK5 kinase consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the PKC Zeta consensus substrate motif, and will specifically recognize a plurality of different proteins within a genome that contain this motif.

D. Insulin Receptor Consensus Substrate Motif

Insulin binding to the α subunits of the insulin receptor (IR) activates its tyrosine kinase activity in 1 subunits. Insulin receptor kinase phosphorylates its substrates at a short consensus motif, Y*MXM. Context-independent antibodies specific for the IR consensus substrate motif, Y*MXM, were produced by synthesizing the following biased degenerate peptide library: CXXX(E/D)(E/D)(E/D)Y*MMMFXX (SEQ ID NO: 101), where Y* is phosphotyrosine and bold indicates invariant motif residues, X represents any amino acid excluding cysteine (C) and tryptophan (W), and underlined residues, E/D, M, and F=degenerate positions at which the representation of amino acids is biased to 50% of the underlined residue(s) (glutamic acid/aspartic acid (E/D), methionine (M) or phenylalanine (F), respectively, where E/D means the 50% bias at that position is to E and D collectively) and 50% of all other amino acids excluding cysteine and tryptophan. Bias towards these particular residues at the given degenerate positions was chosen based upon the prior determination of flanking residues (in peptide substrates) favored by insulin receptor kinases, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (M or F, respectively, or in the case of E/D, 50% of the coupling mixture comprised E and D collectively (i.e. 25% bias for each of E and D) and the other 50% comprised a mixture of all amino acids, substantially as described in Example 1, excluding C and W.

The IR consensus substrate motif degenerate peptide library was coupled to KLH and injected into rabbits as described above in Example 1. Antisera from the most promising rabbit was purified over protein A and adsorbed over an unmodified (nonphospho) IR consensus substrate motif peptide library column. The flow-through of this column was applied to a modified (phospho)-IR consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the all or part of the IR consensus substrate motif, and will specifically recognize a plurality of different proteins within a genome that contain this motif.

E. PI3K P85 Binding Motif

PI3K (phosphoinositide-3 kinase) is a heterodimer consisting of a P85 adaptor subunit a P110 catalytic subunit. PI3K is important to signaling by protein-tyrosine kinase receptors. PI3K uses $SH_2$ domains within the p85 subunit to bind the tyrosine phosphorylated motif, Y*MXM. Context-independent antibodies specific for the PI3K P85 consensus substrate motif, Y*MXM (SEQ ID NO: 102), were produced by synthesizing the following degenerate peptide library: CXXXXXXEY*MXMXXX (SEQ ID NO: 103), where Y* is phosphotyrosine and bold indicates invariant motif residues, X represents any amino acid excluding cysteine (C) and tryptophan (W), and the underlined residue, E, is a degenerate position at which the representation of amino acids is biased to 50% of E, and) and 50% of all other amino acids excluding cysteine and tryptophan. Bias towards this particular residue at the given degenerate position was chosen based upon the prior determination of flanking residues (in peptide substrates) favored by PI3K P85 binding, substantially as described above.

The degenerate peptide library was synthesized by standard F-Moc solid phase peptide synthesis using an ABI peptide synthesizer and amino acid mixtures (further excluding tryptophan (W)) for coupling reactions, substantially as described in Example I.

The PI3K P85 binding motif degenerate peptide library was coupled to KLH and injected into rabbits as described above in Example 1. Antisera from the most promising rabbit was purified over protein A and adsorbed over an unmodified (nonphospho) PI3K P85 binding motif peptide library column. The flow-through of this column was applied to a modified (phospho)-PI3K P85 binding motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the PI3K P85 binding motif, and will specifically recognize a plurality of different proteins within a genome that contain this motif.

F. CaMKII Consensus Substrate Motif

CaMKII (calcium/calmodulin-dependent kinase II) is a kinase that phosphorylates its substrates at a short consensus motif, RQXT*FD (SEQ ID NO: 104). Context-independent antibodies specific for the CaMKII consensus substrate motif, RQXT*FD (SEQ ID NO: 104), were produced by synthesizing the following biased degenerate peptide library: CXXKRQQT*FDLFXXX (SEQ ID NO: 105), where T* is phosphothreonine and bold indicates invariant motif residues, X represents any amino acid excluding cysteine (C) and tryptophan, and underlined residues, K, Q, L, and F=degenerate positions at which the representation of amino acids is biased to 50% of the underlined residue(s) (lysine (L), glutamine (Q), leucine (L), or phenylalanine (F), respectively) and 50% of all other amino acids excluding cysteine and tryptophan. Bias towards these particular residues at the given degenerate positions was chosen based upon the prior determination of flanking residues (in peptide substrates) favored by CaMKII kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (K, Q, L, or F, respectively) and the other 50% comprised a mixture of all amino acids, substantially as described in Example 1, excluding C and W.

The CaMKII consensus substrate motif degenerate peptide library was coupled to KLH and injected into rabbits as described above in Example 1. Antisera from the most promising rabbit was purified over protein A and adsorbed over an unmodified (nonphospho) CaMKII consensus motif peptide library column. The flow-through of this column was applied to a modified (phospho)-CaMKII consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of all or part of the CaMKII consensus substrate motif, and will specifically recognize a plurality of different proteins within a genome that contain this motif.

G. Src Consensus Substrate Motif

Src is a kinase that phosphorylates its substrates at a short consensus motif, EXIY*GEF (SEQ ID NO: 106). Context-independent antibodies specific for the SRC consensus substrate motif, EXIY*GEF, were produced by synthesizing the following biased degenerate peptide library: CXXXEE EIY*GEFXXXX (SEQ ID NO: 107), where Y* is phosphotyrosine and bold indicates invariant motif residues, X represents any amino acid excluding cysteine (C) and tryptophan, and underlined residues, E,=degenerate positions at which the representation of amino acids is biased to 50% of the underlined residue(s) (glutamic acid (E)) and 50% of all other amino acids excluding cysteine and tryptophan. Bias towards these particular residues at the given degenerate positions was chosen based upon the prior determination of flanking residues (in peptide substrates) favored by SRC kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (E) and the other 50% comprised a mixture of all amino acids, substantially as described in Example 1, excluding C and W.

The SRC consensus substrate motif degenerate peptide library was coupled to KLH and injected into rabbits as described above in Example 1. Antisera from the most promising rabbit was purified over protein A and adsorbed over an unmodified (nonphospho) SRC consensus motif peptide library column. The flow-through of this column was applied to a modified (phospho)-SRC consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the SRC consensus substrate motif, and will specifically recognize a plurality of different proteins within a genome that contain this motif.

H. CDC2/CDK2 Consensus Substrate Motif

CDC2/CDK2 (cell division cycle protein 2/cyclin dependent kinase 2) is a kinase that phosphorylates its substrates at a short consensus motif, S*PR(K/R) (SEQ ID NO: 108). Context-independent antibodies specific for the CDC2/CDK2 consensus substrate motif, S*PR(K/R), were produced by synthesizing the following biased degenerate peptide library: CXXXHHH(K/R)S*PR(K/R)RXXX (SEQ ID NO: 109), where S* is phosphoserine and bold indicates invariant motif residues (K/R indicating either K or R must be present at that position), X represents any amino acid excluding cysteine (C) and tryptophan, and underlined residues, H, K/R, and R=degenerate positions at which the representation of amino acids is biased to 50% of the underlined residue(s) (histidine (H), lysine/arginine (K/R), or arginine (R), respectively, where K/R means the 50% bias at that position is to K and R collectively) and 50% of all other amino acids excluding cysteine and tryptophan. Bias towards these particular residues at the given degenerate positions was chosen based upon the prior determination of flanking residues (in peptide substrates) favored by CDC2/CDK2 kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (H or R, respectively, or in the case of K/R, 50% of the coupling mixture comprised K and R collectively (i.e. 25% bias for each of K and R) and the other 50% comprised a mixture of all amino acids, substantially as described in Example 1, excluding C and W.

The CDC2/CDK2 consensus substrate motif degenerate peptide library was coupled to KLH and injected into rabbits as described above in Example 1. Antisera from the most promising rabbit was purified over protein A and adsorbed over an unmodified (nonphospho) CDC2/CDK2 consensus motif peptide library column. The flow-through of this column was applied to a modified (phospho)-CDC2/CDK2 consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of all or part of the CDC2/CDK2 consensus substrate motif, and will specifically recognize a plurality of different proteins within a genome that contain this motif.

I. GSK3 Consensus Substrate Motif

GSK3 (glycogen synthase kinase-3) is a kinase that phosphorylates its substrates at a short consensus motif, T*PXXS*P (SEQ ID NO: 110). Context-independent antibodies specific for the GSK3 consensus substrate motif, T*PXXS*P (SEQ ID NO: 110), were produced by synthesizing the following biased degenerate peptide library: CX(P/F)X(P/L)(P/L)PT*PP(P/L)S*PXXXXX (SEQ ID NO: 111), where T* is phosphothreonine, S* is phosphoserine and bold indicates invariant motif residues, X represents any amino acid excluding cysteine (C) and tryptophan, and underlined residues, P/F, P/L, and P=degenerate positions at which the representation of amino acids is biased to 50% of the underlined residue(s) (proline/phenylalanine (P/F), proline/leucine (P/L), or proline (P), respectively, where P/F and P/L mean the 50% bias at that position is to P and F, or P and L, collectively) and 50% of all other amino acids excluding cysteine and tryptophan. Bias towards these particular residues at the given degenerate positions was chosen based upon the prior determination of flanking residues (in peptide substrates) favored by GSK3 kinase, substantially as described above.

The degenerate peptide library was synthesized by standard F-Moc solid phase peptide synthesis using an ABI peptide synthesizer and amino acid mixtures (further excluding tryptophan (W)), substantially as described in Example I. However, for the biased degenerate positions indicated, the mixtures of amino acids used during degenerate coupling reactions were as follows: 50% of the coupling mixture comprised the biased flanking residue (P, or in the case of P/F and P/L, 50% of the coupling mixture comprised P and F, or P and L, collectively (i.e. 25% bias for each of P and F or L) and the other 50% comprised a mixture of all amino acids, substantially as described in Example 1, excluding C and W.

The GSK3 consensus substrate motif degenerate peptide library was coupled to KLH and injected into rabbits as described above in Example 1. Antisera from the most promising rabbit was purified over protein A and adsorbed over an unmodified (nonphospho)GSK3 consensus motif peptide library column. The flow-through of this column was applied to a modified (phospho)-GSK3 consensus motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the GSK3 consensus substrate motif, and will specifically recognize a plurality of different proteins within a genome that contain this motif.

J. Proline-Phosphoserine-Proline Motif

Some important signaling proteins can be regulated by phosphorylation at a serine between two adjacent prolines. For example, GSK3 phosphorylates its substrates at T*P or S*P preceded preferentially by proline. P53 and L-myc also contain a phosphorylated serine between two prolines. Context-independent antibodies specific for this motif, PS*P, were produced by synthesizing the following degenerate peptide library: CXXXXXPS*PXXXXXX (SEQ ID NO: 112), where S* is phosphoserine and bold indicates invariant motif residues, and X represents any amino acid excluding cysteine (C) and tryptophan. No bias was introduced at any of the degenerate residues flanking the motif.

The degenerate peptide library was synthesized by standard F-Moc solid phase peptide synthesis using an ABI peptide synthesizer and amino acid mixtures (further excluding tryptophan (W)) for coupling reactions, substantially as described in Example I.

The PS*P motif degenerate peptide library was coupled to KLH and injected into rabbits as described above in Example 1. Antisera from the most promising rabbit was purified over protein A and adsorbed over an unmodified (nonphospho) serine peptide library column. The flow-through of this column was applied to a modified (phospho)-PS*P binding motif column eluted at low pH, dialyzed and tested for phosphospecificity. Initial results indicate these antibodies are phospho-specific (data not shown), and it is anticipated that further specificity testing by ELISA, as outlined in Example 1, will indicate these motif-specific, context-independent antibodies are highly specific for the phosphorylated form of the PS*P motif, and will specifically recognize a plurality of different proteins within a genome that contain this motif.

Example XVI

Context-Independent Antibodies Specific for Other Motifs

A. Methyl-Arginine Motif rGG

Methyltransferases are a class of enzymes that methylate their substrates at short consensus motifs comprising arginine and/or lysine. One such motif is rGG (r=di-methylarginine). Context-independent antibodies specific for this substrate motif may be produced by synthesizing the following biased degenerate peptide library: CXXXXXrGGXXXXX (SEQ ID NO: 315), where r=is di-methylarginine and bold indicates invariant motif residues, X represents any amino acid excluding cysteine (C) and tryptophan.

The degenerate peptide library is synthesized by standard F-Moc solid phase peptide synthesis using an ABI peptide synthesizer and amino acid mixtures, substantially as described in Example I. The rGG motif degenerate peptide library is coupled to KLH and injected into rabbits as described above in Example 1. Antisera from the most promising rabbit are purified over protein A and adsorbed over an unmodified (nonmethyl) rGG consensus motif peptide library column. The flow-through of this column is then applied to a modified (methyl) rGG consensus motif column eluted at low pH, dialyzed and tested for methyl-specificity. Initial results will indicate if these antibodies are methyl-specific, and it is anticipated that further specificity testing by ELISA, as outlined in Example 1, will indicate these motif-specific, context-independent antibodies are highly specific for the methylated form of the rGG substrate motif, and will specifically recognize a plurality of different proteins within a genome that contain this motif.

B. Acetyl-Lysine Motif (XXkXXXK)

Acetyltransferases are a class of enzymes that acetylate their substrates at short consensus motifs comprising at least one lysine. Context-independent antibodies specific for the XXkXXXK substrate motif may be produced by synthesizing the following biased degenerate peptide library: CXXXXkXXXKXXXX, where k=acetyl-lysine and bold indicates invariant motif residues, X represents any amino acid excluding cysteine (C) and tryptophan (W).

The degenerate peptide library is synthesized by standard F-Moc solid phase peptide synthesis using an ABI peptide synthesizer and amino acid mixtures substantially as described in Example I. The XXkXXXK consensus motif degenerate peptide library is coupled to KLH and injected into rabbits as described above in Example 1. Antisera from the most promising rabbit was purified over protein A and adsorbed over an unmodified (nonacetyl) XXkXXXK consensus motif peptide library column. The flow-through of this column is applied to a modified (acetyl) XXkXXXK consensus motif column eluted at low pH, dialyzed and tested for acetylspecificity. Initial results will indicate if these antibodies are phospho-specific (data not shown), and it is anticipated that further specificity testing by ELISA, as outlined in Example 1, will indicate these motif-specific, context-independent antibodies are highly specific for the all or part of the acetylated form of the XXkXXXK consensus substrate motif, and will specifically recognize a plurality of different proteins within a genome that contain this motif.

What is claimed is:

1. A motif-specific, context-independent antibody that specifically binds a modified motif, which is recurring in a plurality of non-homologous peptides or proteins within an organism, consisting of (i) two to six invariant amino acids including at least one phosphorylated, acetylated, or methylated amino acid, and, optionally, (ii) one or more degenerate amino acid position(s), said antibody specifically binding said motif in a plurality of non-homologous peptides or proteins within an organism in which it recurs.

2. The antibody of claim 1, wherein said motif is selected from the group consisting of methylarginine-G-G, methylarginine-G-G-methylarginine-G-G (SEQ ID NO:317), methylarginine-X-methylarginine, methylarginine-G, and G-methylarginine-G.

3. The antibody of claim 1, wherein said motif is selected from the group consisting of XXkXXXXK, XXGkXX, XXkXE, XXKkXX, XXEkXX, XXkLXX, and XXkX-EXKXX, wherein k=acetyl-lysine.

4. The antibody of claim 1, wherein said motif is a phosphorylated kinase consensus substrate motif selected from the group consisting of XX[s/t]PX, X[S/T]X[s/t]XX, XX[s/t]XXX[S/T]X, XX[s/t]X[D/E]X, X[S/T]XX[s/t]XX, XX[s/t]XXX[E/D]X, XX[s/t]XXXXPX, XX[s/t][L/I]X, XD[s/t]XX, XX[s/t]DX, XX[s/t]QX, X[V/L/I]Yxx, X[D/E]XXyXX, XyXX[V/L]X, X[D/E]XyXX, XXyXX[I/M]X, XXyXNX, XNXyXX, XYyXX, XHyXX, XXyXXCX, XyXXXXCX, and XyXXXWX, wherein s=phosphoserine, t=phosphothreonine, and y=phosphotyrosine.

5. The antibody of claim 1, wherein said motif is a phosphorylated kinase consensus substrate motif selected from the group consisting of an AGC kinase consensus substrate motif, an Akt kinase consensus substrate motif, an AMPK kinase consensus substrate motif, an ATM/ATR kinase consensus substrate motif, a CaMK kinase consensus substrate motif, a Cdc2 kinase consensus substrate motif, a CDK kinase consensus substrate motif, a Chk1 kinase consensus substrate motif, a CK kinase consensus substrate motif, a CLK kinase consensus substrate motif, a DAPK3 kinase consensus substrate motif, a DCAMKL1 kinase consensus substrate motif, a DMPK kinase consensus substrate motif, a Dual specificity JNK kinase consensus substrate motif, a Dual specificity MAPK kinase consensus substrate motif, a Dual specificity p38 kinase consensus substrate motif, and a DYRK1A kinase consensus substrate motif.

6. The antibody of claim 1, wherein said motif is a phosphorylated kinase consensus substrate motif selected from the group consisting of an ERK1 kinase consensus substrate motif, a GSK3 kinase consensus substrate motif, a Histone H kinase consensus substrate motif, a KSR kinase consensus substrate motif, a LKB1 kinase consensus substrate motif, a MAPKAPK-2 kinase consensus substrate motif, a MAPKKK kinase consensus substrate motif, a Nek1 kinase consensus substrate motif, a PAK kinase consensus substrate motif, a PDK1 kinase consensus substrate motif, a Phosphorylase kinase consensus substrate motif, a Pim1 kinase consensus substrate motif, a PKA kinase consensus substrate motif, a PKC kinase consensus substrate motif, a PKG kinase consensus substrate motif, a Proline-directed kinase consensus substrate motif, a SLK1 kinase consensus substrate motif and a TGF-beta kinase consensus substrate motif.

7. The antibody of claim 1, wherein said motif is a phosphorylated protein binding motif selected from the group consisting of a MDC1 binding motif, a CDC4/WD40 binding motif, a BRCA1 binding motif, a Chk2/FHA binding motif, a 14-3-3 binding motif, a BRCT binding motif, a BARD1 binding motif, a WW binding motif, a RAD9 binding motif, a SCF-Beta/TROP binding motif, a Plk1/Polobox binding motif, a PP1 binding motif, and a FHA binding motif.

8. The antibody of claim 1, wherein said motif is a phosphorylated phosphatase consensus substrate motif selected from the group consisting of a PP2C delta consensus substrate motif, a MKP1 consensus substrate motif, a MKP3 consensus substrate motif, and a Calcinuerin consensus substrate motif.

9. The antibody of any one of claims 1-8 produced by a method comprising the steps of:
(a) constructing a degenerate peptide library comprising (i) a fixed target motif comprising two to six invariant amino adds including at least one modified amino add, and, optionally, one or more degenerate amino add position(s), and (ii) a plurality of degenerate amino adds flanking said motif;
(b) immunizing a host with said peptide library to raise a context-independent antibody specific for all or part of said target motif; and
(c) isolating antisera from said host, and purifying the motif-specific, context-independent antibody of step (b) from said antisera, said antibody specifically binding said motif in a plurality of peptides or proteins within an organism in which it recurs.

10. The method of claim 9, further comprising the step of utilizing spleen cells from the host of step (b) to generate at least one monoclonal; motif-specific, context-independent antibody.

11. The method of claim 9, wherein said peptide library is from 6 to 20 amino adds long.

12. The method of claim 9, wherein said peptide library is from 6 to 14 amino adds long.

* * * * *